US008143226B2

(12) United States Patent
Goldfine et al.

(10) Patent No.: US 8,143,226 B2
(45) Date of Patent: Mar. 27, 2012

(54) TYROSINE KINASE RECEPTOR ANTAGONISTS AND METHODS OF TREATMENT FOR BREAST CANCER

(75) Inventors: Ira Goldfine, San Francisco, CA (US); John Kerner, San Francisco, CA (US); Betty A. Maddux, San Francisco, CA (US); Michael Campbell, Woodside, CA (US); Jack F. Youngren, San Francisco, CA (US); Peter Kushner, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 110 days.

(21) Appl. No.: 11/552,686

(22) Filed: Oct. 25, 2006

(65) Prior Publication Data

US 2007/0099847 A1      May 3, 2007

Related U.S. Application Data

(60) Provisional application No. 60/731,384, filed on Oct. 28, 2005, provisional application No. 60/825,663, filed on Sep. 14, 2006, provisional application No. 60/828,937, filed on Oct. 10, 2006.

(51) Int. Cl.
*A61K 31/70* (2006.01)
*A61K 31/404* (2006.01)

(52) U.S. Cl. .................................. 514/23; 514/414

(58) Field of Classification Search ................ 514/23, 514/414, 23.414
See application file for complete search history.

(56) References Cited

U.S. PATENT DOCUMENTS

| | | | |
|---|---|---|---|
| 2,644,822 A | 7/1953 | Pearl et al. | |
| 5,861,268 A | 1/1999 | Tang et al. | |
| 6,191,169 B1 | 2/2001 | Nadler et al. | |
| 6,437,105 B1 * | 8/2002 | Priebe et al. | 536/6.4 |

OTHER PUBLICATIONS

Osborne et al, Cancer Research, 1992, 52, 3636-41.*
Robins et al, Anti-Cancer Drug Design, 2001, 16, 261-70.*
Rozengurt et al, The Journal of Biological Chemistry, 1994, 269(11), 8260-67.*
Robertson et al, Endocrine Related Cancer, Mar. 12, 2005, S135-S144.*
Seufferlein et al, British Journal of Cancer, 2002, 86, 1188-96.*
Trisha Gura, Science, Nov. 1997, 278(5340), 1041-42.*
Doctors Guide, Sep. 28, 1998, pp. 1-3.*
Scheithauer et al, Breast Cancer Research and Treatment, 1985, 6, 89-93.*
Blum et al., "Development of New Insulin-like Growth Factor-1 Receptor Kinase Inhibitors Using Catechol Mimics" The Journal of Biological Chemistry, 278(42):40442-40454 (2003).
Blum et al., "Substrate Competitive Inhibitors of IGF-1 Receptor Kinase" Biochemistry, 39:15705-15712 (2000).
Seufferlein et al., "Mechanisms of nordihydroguaiaretic acid-induced growth inhibition and apoptosis in human cancer cells" British Journal of Cancer, 86:1188-1196 (2002).
Youngren, et al., "Novel Small Molecule Inhibitors of the IGF-1R Receptor Inhibit Breast Cancer Growth" Growth Hormone & IGF Research, 14:102-103 (2004).
Ryan et al., "A pilot dose-escalation study of effects of nordihydroguaiaretic acid on hormone and prostate specific antigen levels in patients with relapsed prostate cancer" Journal Compilation, BJU International, 101:436-439 (2008).
Earashi et al., "Effects of Eicosanoid Synthesis Inhibitors on the in vitro Growth and Prostaglandin E and Leukotriene B. Secretion of a Human Breast Cancer Cell Line" Oncology, 52:150-155 (1995).
Greco et al., "The Search for Syngergy: A Critical Review from a Response Surface Perspective," Pharmacological Reviews 47(2):331-385 (1995).
Kano et al., "Effects of CPT-11 in Combination with Other Anti-Cancer Agents in Culture," Int J Cancer 50:604-610 (1992).
McDonald et al., "Synthesis and anticancer activity of nordihydroguaiaretic acid (NDGA) and analogues," Anti-Cancer Drug Design 16:261-270 (2001).
Steel et al., "Exploitable Mechanisms in Combined Radiotherapy-Chemotherapy: The Concept of Additivity," Int J Radiation Oncology Biol Phys 5:85-91 (1979).

* cited by examiner

*Primary Examiner* — Shaojia Anna Jiang
*Assistant Examiner* — Ganapathy Krishnan
(74) *Attorney, Agent, or Firm* — Wilson, Sonsini, Goodrich & Rosati

(57) ABSTRACT

A method of treatment is disclosed whereby cancer cells are brought into contact with a formulation comprising an inhibitor of tyrosine kinase receptors. The formulation may be comprised of an injectable carrier and two or more tyrosine kinase receptor inhibitors which may be nordihydroguaiaretic acid (NDGA) and doxorubicin.

12 Claims, 31 Drawing Sheets

NORDIHYDROGUAIARETIC ACID (NDGA)

Effect of NDGA on PC-3 prostate cancer cell growth. Cells were plated at $10^5$ per well in the absence and presence of NDGA for 4 days. Results are the mean ± SD for triplicates determinations.

WB: α-pY

NDGA (μM)   0   0.01   0.1   1   10   100

○ -- control, no drug

▲ -- 37.5 mg/Kg 3 times per week

■ -- 100 mg/Kg 3 times per week

Basal 3 nM IGF-1

NDGA (μM)　　0　　10　　30

TYROSINE KINASE RECEPTOR ANTAGONISTS AND METHODS OF TREATMENT FOR BREAST CANCER

CROSS-REFERENCE

This application claims the benefit of U.S. Provisional Application Nos. 60/731,384 filed Oct. 28, 2005; 60/825,663 filed Sep. 14, 2006; and 60/828,937 filed Oct. 10, 2006, which applications are incorporated herein by reference.

BACKGROUND OF THE INVENTION

Many tumor cells depend on the activity of tyrosine kinases, which act, among other functions, to depress apoptosis in the cell. The tyrosine kinases are usually overproduced in malignant cells, which contributes to the cell's ability to resist apoptosis. Modulating the activity of these proteins provides an effective means of treating cancer while not unduly damaging normal tissues. For example, about 25% of breast tumors express unusually high levels of the Her2 protein, a tyrosine kinase receptor that normally plays a part in the development of the mammary epithelium. Herceptin® (Trastuzumab) is a humanized antibody that is currently used to treat breast cancer by targeting and blocking the function of the Her2 protein. Other treatments focus on interfering with the receptors to overexpressed tyrosine kinase proteins. Receptors include HER2/neu and IGF-1R. See, Meric et al. (April 2002) *J. Am. Coll. Surg.* 194(4):488-501.

The major lignin in chaparral, known as nordihydroguaiaretic acid (NDGA) is a potent antioxidant and was originally used in commercial food products as a preservative. See, U.S. Pat. No. 2,644,822. Later, it was discovered that NDGA is useful in the treatment of diabetes. Hsu et al. (2001) *Cell Transplant.* 10(3):255-262. More recently, NDGA was investigated as a treatment for cancer because it inhibits the platelet derived growth factor receptor and the protein kinase C intracellular signalling family, which both play an important role in proliferation and survival of cancers. Moreover, NDGA induces apoptosis in tumor xenografts. Although it is likely to have several targets of action, NDGA is well tolerated in animals. However, high concentrations of NDGA are required for efficacy and it has been suggested that more potent analogs may be required. See, McDonald et al. (2001) *Anticancer Drug Des.* 16(6):261-270.

Other cancer drugs include doxorubicin hydrochloride (DOX), which is used alone or in combination with other drugs for treatment of malignant lymphomas and leukemias. DOX is believed to bind DNA and inhibit nucleic acid synthesis. Examples of tumors amenable to treatment with DOX are acute lymphoblastic leukemia, acute myeloblastic leukemia, Wilm's tumor, soft tissue and bone sarcomas, breast carcinoma and ovarian carcinoma. The dosage needs to be closely monitored because it can cause irreversible cardiac damage. A typical dose for adults, when given intravenously is 60-75 mg/m2 once in 21 days, or 30 mg/m2 daily for 3 days every four weeks, where the total cumulative dose should not exceed 550 mg/m2 without monitoring for cardiac function.

It is well established that breast cancer is regulated by receptors for the female sex steroids, estrogen and progesterone. It is now appreciated that receptor tyrosine kinases (RTKs) are also very important for breast cancer growth (Arteaga CL, Moulder SL, Yakes FM: HER (erbB) tyrosine kinase inhibitors in the treatment of breast cancer. Semin Oncol 29:4-10, 2002; Averbuch S, Kcenler M, Molis C, Wakeling A: Therapeutic potential of tyrosine kinase inhibitors in breast cancer. Cancer Invest 21:782-791, 2003; Baserga R: The IGF-I receptor in cancer research. Exp Cell Res 253:1-6, 1999; Dickson RB, Lippman ME: Growth factors in breast cancer. Endocr Rev 16:559-589, 1995; Gross JM, Yee D: The type-1 insulin-like growth factor receptor tyrosine kinase and breast cancer: biology and therapeutic relevance. Cancer Metastasis Rev 22:327-336, 2003; and Nahta R, Hortobagyi GN, Esteva FJ: Growth factor receptors in breast cancer: potential for therapeutic intervention. Oncologist 8:5-17, 2003).

Accordingly, RTKs are targets for anti-tumor therapy. RTKs are transmembrane proteins that typically contain an extracellular ligand binding domain, activated by peptide hormones, and an intracellular tyrosine kinase domain. Two RTKs of demonstrated importance in breast and other cancers are the insulin-like growth factor receptor (IGF-1R) (Heinemann V: Present and future treatment of pancreatic cancer. Semin Oncol 29:23-31, 2002) and c-erbB2/HER2/neu (HER2/neu) (Morin MJ: From oncogene to drug: development of small molecule tyrosine kinase inhibitors as anti-tumor and anti-angiogenic agents. Oncogene 19:6574-6583, 2000). Based on their major role in regulating cancer cell growth and survival, inhibitors of these RTKs are undergoing drug development (Morin MJ: From oncogene to drug: development of small molecule tyrosine kinase inhibitors as anti-tumor and anti-angiogenic agents. Oncogene 19:6574-6583, 2000; Bruns CJ, Solorzano CC, Harbison MT, Ozawa S, Tsan R. Fan D, Abbruzzese J, Traxler P, Buchdunger E, Radinsky R, Fidler IJ: Blockade of the epidermal growth factor receptor signaling by a novel tyrosine kinase inhibitor leads to apoptosis of endothelial cells and therapy of human pancreatic carcinoma. Cancer Res 60:2926-2935, 2000; Bruns CJ, Harbison MT, Davis DW, Portera CA, Tsan R, McConkey DJ, Evans DB, Abbruzzese JL, Hicklin DJ, Radinsky R: Epidermal growth factor receptor blockade with C225 plus gemcitabine results in regression of human pancreatic carcinoma growing orthotopically in nude mice by antiangiogenic mechanisms. Clin Cancer Res 6:1936-1948, 2000; Blum G, Gazit A, Levitzki A: Substrate competitive inhibitors of IGF-1 receptor kinase. Biochemistry 39:15705-15712, 2000).

Signaling via the IGF-1R is important for normal cell growth and differentiation. In addition, the IGF-1R stimulates mitogenesis and suppresses apoptosis of cancer cells (Lowe WL: Biological actions of the insulin-like growth factors. In LeRoith D (ed): Insulin-like growth factors: molecular and cellular aspects. Boca Raton, CRC Press, 1991). Following binding of the ligand to the IGF-1R, a conformational change induces trans-autophosphorylation of the β-subunits on select tyrosine residues, and subsequent activation of tyrosine kinase activity (Lowe WL: Biological actions of the insulin-like growth factors. In LeRoith D (ed): Insulin-like growth factors: molecular and cellular aspects. Boca Raton, CRC Press, 1991). Phosphorylation of several target substrates activates divergent signaling cascades, though the anti-apoptotic effects of the IGF-1R are primarily mediated via the Akt/PKB pathway (Kulik G, Klippel A, Weber MJ: Antiapoptotic signalling by the insulin-like growth factor I receptor, phosphatidylinositol 3-kinase, and Akt. Mol Cell Biol 17:1595-1606, 1997).

Tyrosine phosphorylation of the insulin receptor substrate (IRS) family of proteins by the IGF-1R allows binding of the regulatory subunit of phosphatidylinositol 3-kinase (PI3K) to the IRS proteins via SH2 domains. Activated PI3K serine phosphorylates and activates the serine kinase Akt (Alessi DR, Andjelkovic M, Caudwell B, Cron P, Morrice N, Cohen P, Hemmings BA: Mechanism of activation of protein kinase B by insulin and IGF-1. EMBO J 15:6541-6551, 1996). Akt can phosphorylate the protein BAD, which prevents BAD from forming a pro-apoptotic complex with Bcl-2 proteins (Virdee K, Parone PA, Tolkovsky AM: Phosphorylation of the pro-apoptotic protein BAD on serine 155, a novel site, contributes to cell survival. Curr. Biol 10:1151-1154. 2000).

Interruption of the IGF-1R signaling system, either by reducing effective IGF-1 levels or targeting the receptor., can block growth and proliferation of cancer cells (Kahan Z. Varga JL, Schally AV, Rekasi Z, Armatis P, Chatzistamou L, Czompoly T, Halmos G: Antagonists of growth hormone-releasing hormone arrest the growth of MDA-MB-468 estrogen-independent human breast cancers in nude mice. Breast Cancer Res Treat 60:71-79, 2000: Neuenschwander S, Roberts CT, Jr., LeRoith D: Growth inhibition of MCF-7 breast cancer cells by stable expression of an insulin-like growth factor I receptor antisense ribonucleic acid. Endocrinology 136:4298-4303, 1995: Prager D, Li HL. Asa S, Melmed S: Dominant negative inhibition of tumorigenesis in vivo by human insulin-like growth factor I receptor mutant. Proc Natl Acad Sci USA 91:2181-2185, 1994; Weckbecker G, Tolcsvai L, Liu R, Bruns C: Preclinical studies on the anticancer activity of the somatostatin analogue octreotide (SMS 201-995). Metabolism 41:99-103, 1992; and Yee D, Jackson JG, Kozelsky TW, Figueroa JA: Insulin-like growth factor binding protein 1 expression inhibits insulin-like growth factor I action in MCF-7 breast cancer cells. Cell Growth Differ 5:73-77. 1994). While overexpression of the IGF-1R can drive transformation and mitogenesis, it is the requirement for its constitutive presence in cancer cells (Rubin R, Baserga R: Insulin-like growth factor-I receptor. Its role in cell proliferation, apoptosis, and tumorigenicity. Lab Invest 73:311-331, 1995) that makes this RTK an attractive target for anti-tumor therapies.

The HER2/neu (c-erbB-2) protooncogene encodes a 1,255 amino acid, 185 kDa member of the class I RTK family. HER2/neu is overexpressed in 20-30% of breast cancers, most commonly via gene amplification, and overexpression is associated with poor prognosis in these patients (Slamon DJ, Godolphin W. Jones LA, Holt JA, Wong SG, Keith DE, Levin WJ, Stuart SG, Udove J. Ullrich A,.: Studies of the HER-2/neu proto-oncogene in human breast and ovarian cancer. Science 244:707-712, 1989; Slamon DJ, Clark GM, Wong SG, Levin WJ, Ullrich A, McGuire WL: Human breast cancer: correlation of relapse and survival with amplification of the HER-2/neu oncogene. Science 235:177-182, 1987). Evidence from transgenic animal studies indicates that HER2/neu overexpression directly contributes to transformation and tumor progression (Bol D, Kiguchi K, Beltran L, Rupp T, Moats S, Gimenez-Conti I, Jorcano J, DiGiovanni J: Severe follicular hyperplasia and spontaneous papilloma formation in transgenic mice expressing the neu oncogene under the control of the bovine keratin 5 promoter. Mol Carcinog 21:2-12, 1998; Bouchard L, Lamarre L, Tremblay PJ, Jolicoeur P: Stochastic appearance of mammary tumors in transgenic mice carrying the MMTV/c-neu oncogene. Cell 57:931-936, 1989; and Lucchini F, Sacco MG, Hu N, Villa A, Brown J, Cesano L, Mangiarini L, Rindi G, Kindl S, Sessa F,.: Early and multifocal tumors in breast, salivary, harderian and epididymal tissues developed in MMTY-Neu transgenic mice. Cancer Lett 64:203-209, 1992), and suggests that its prognostic significance arises from the particularly aggressive phenotype it confers (Hynes NE, Stern DF: The biology of erbB-2/neu/HER-2 and its role in cancer. Biochim Biophys Acta 1198:165-184, 1994). The efficacy of targeting HER2/neu in anti-cancer therapy has been demonstrated by the clinical use of an antibody to HER2/neu to treat certain patients with breast cancer (Albanell J, Baselga J: Trastuzumab, a humanized anti-HER2 monoclonal antibody, for the treatment of breast cancer. Drugs Today (Barc) 35:931-946, 1999).

Nordihydroguaiaretic acid (NDGA) is a phenolic compound that was identified as a major component of a tea made from resinous extracts of the creosote bush *Larrea divaricatta*. It has been used for centuries by Native North Americans as a remedy for diverse illnesses, including tumors (Duisberg PC: Desert Plant Utilization. Texas J Sci 4:269, 1952: Hawthorn P: Medicinal uses of plants of Nevada used by Indians. Contr Flora Nevada 45:1-139, 1957). NDGA has been reported to inhibit the growth of various tumors both in vitro and in animals (Wilson DE, DiGianfilippo A, Ondrey FG, Anderson KM, Harris JE: Effect of nordihydroguaiaretic acid on cultured rat and human glioma cell proliferation. J Neurosurg 71:551-557, 1989; Avis IM, Jett M, Boyle T, Vos MD, Moody T, Treston AM, Martinez A, Mulshine JL: Growth control of lung cancer by interruption of 5-lipoxygenase-mediated growth factor signaling. J Clin Invest 97:806-813, 1996; Rose DP, Connolly JM: Effects of fatty acids and inhibitors of eicosanoid synthesis on the growth of a human breast cancer cell line in culture. Cancer Res 50:7139-7144, 1990: and Shimakura S, Boland CR: Eicosanoid production by the human gastric cancer cell line AGS and its relation to cell growth. Cancer Res 52:1744-1749, 1992). NDGA also has been reported to induce apoptosis in a variety of cell lines (Ding XZ, Kuszynski CA, El Metwally TH, Adrian TE: Lipoxygenase inhibition induced apoptosis, morphological changes, and carbonic anhydrase expression in human pancreatic cancer cells. Biochem Biophys Res Commun 266: 392-399, 1999: La E, Kern JC, Atarod EB, Kehrer JP: Fatty acid release and oxidation are factors in lipoxygenase inhibitor-induced apoptosis. Toxicol Lett 138:193-203, 2003; Seufferlein T, Seckl MJ, Schwarz E, Beil M, Wichert G, Baust H, Luhrs H, Schmid RM, Adler G: Mechanisms of nordihydroguaiaretic acid-induced growth inhibition and apoptosis in human cancer cells. Br J Cancer 86:1188-1196, 2002; Tong WG, Ding XZ, Witt RC, Adrian TE: Lipoxygenase inhibitors attenuate growth of human pancreatic cancer xenografts and induce apoptosis through the mitochondrial pathway. Mol Cancer Ther 1:929-935, 2002; and Tong WG, Ding XZ, Adrian TE: The mechanisms of lipoxygenase inhibitor-induced apoptosis in human breast cancer cells. Biochem Biophys Res Commun 296:942-948, 2002). Still, the mechanism of this anti-cancer effect of NDGA is not well understood. It has been reported that NDGA inhibits the tyrosine kinase activity of the platelet-derived growth factor receptor (PDGFR), but not the epidermal growth factor receptor (EGFR), in cells and in vitro (Domin J, Higgins T, Rozengurt E: Preferential inhibition of platelet-derived growth factor-stimulated DNA synthesis and protein tyrosine phosphorylation by nordihydroguaiaretic acid. J Biol Chem 269:8260-8267, 1994). While one report suggests that NDGA is inactive against the IGF-1R (Seufferlein T, Seckl MJ, Schwarz E, Beil M, Wichert G, Baust H. Luhrs H, Schmid RM, Adler G: Mechanisms of nordihydroguaiaretic acid-induced growth inhibition and apoptosis in human cancer cells. Br J Cancer 86:1188-1196, 2002), a compound with a very high degree of structural homology to NDGA has been described as a potent inhibitor of this receptor(Blum G. Gazit A, Levitzki A: Substrate competitive inhibitors of IGF-1 receptor kinase. Biochemistry 39:15705-15712, 2000: Blum G. Gazit A, Levitzki A: Development of new insulin-like growth factor-1 receptor kinase inhibitors using catechol mimics. J Biol Chem 278: 40442-40454, 2003). The effects of NDGA on the HER2/neu receptor, which also plays a critical role in breast cancer, have not been explored. We have now found that NDGA antagonizes the activation of both the IGF-1 and HER2/neu receptors inhibits the cellular anti-apoptotic signaling pathway of the IGF-1R, and inhibits the growth of breast cancer cells both in vitro and in vivo.

There is a need for therapeutic cancer treatments that block the tyrosine kinase receptors with lower dosages of these powerful drugs to reduce side effects. The present invention addresses this and other related needs.

SUMMARY OF THE INVENTION

Treatments for breast and pancreatic cancer are disclosed. The malignant cells are brought into contact with NDGA and diarylurea 21834, either singly or in combination with other compounds, such as doxorubicin and Herceptin.

Nordihydroguaiaretic acid (NDGA) is a phenolic compound isolated from the creosote bush *Larrea divaricatta* that has anti-cancer activities both in vitro and in vivo. These anti-cancer properties in breast cancer cells are created by the ability of NDGA to directly inhibit the function of two receptor tyrosine kinases (RTKs), the insulin-like growth factor receptor (IGF-1R) and the c-erbB2/HER2/neu (HER2/neu) receptor. In MCF-7 human breast cancer cells, low micromolar concentrations of NDGA inhibited activation of the IGF-1R, and downstream phosphorylation of both the Akt/PKB serine kinase and the pro-apoptotic protein BAD.

In mouse MCNeuA cells, NDGA also inhibited ligand independent phosphorylation of HER2/neu. This inhibitory effect in cells is due to a direct action on these receptors. The IGF-1-stimulated tyrosine kinase activity of isolated IGF-1R is inhibited by NDGA at 10 µM or less. A composition of NDGA is also effective at inhibiting autophosphorylation of isolated HER2/neu receptor at similar concentrations. In addition, NDGA inhibits IGF-1 specific growth of cultured breast cancer cells with an IC50 of approximately 30 µM. Treatment with NDGA (intraperitoneal injection 3 times per week) also decreases the activity of the IGF-1R and the HER2/neu receptor in MCNeuA cells implanted into mice. Inhibition of RTK activity is associated with decreased growth rates of MCNeuA cells in vivo. Accordingly, the anti-breast cancer properties of NDGA are related to the inhibition of two important RTKs and as such formulations of RTK inhibitors provide a means of treating breast cancer.

One aspect of the invention comprises methods for using NDGA in the treatment of breast cancer.

A further aspect of the invention is methods for treating breast cancer with a combination of NDGA and Doxorubicin. This formulation provides an unexpected synergistic effect in combination at low concentrations compared to individual dosages. When given in combination, lower dosages may be used to achieve a greater effect, which has the additional benefit of decreasing side-effects compared to the individual drugs given at higher dosages.

Another aspect of the invention is methods for using Diarylurea 21834 (DAU) alone or in various combinations with other compounds for the treatment of breast cancer.

One aspect of the invention comprises methods for using NDGA in the treatment of pancreatic cancer.

A further aspect of the invention is methods for treating pancreatic cancer with a combination of NDGA and Doxorubicin. This formulation provides an unexpected synergistic effect in combination at low concentrations compared to individual dosages. When given in combination, lower dosages may be used to achieve a greater effect, which has the additional benefit of decreasing side-effects compared to the individual drugs given at higher dosages.

Another aspect of the invention is methods for using Diarylurea 21834 (DAU) alone or in various combinations with other compounds for the treatment of pancreatic.

As aspect of the invention is treating a breast cancer patient by administering tamoxifen to the patient: determining that the patient is not sufficiently responsive to tamoxifen; and treating the patient with a combination of tamoxifen and NDGA.

Another aspect of the invention is diagnosing a cancer patient as having estrogen receptor (ER) positive MCF-7 cells that overexpress HER2 (MCF-7/HER2-18) and administering to the patient a therapeutically effective amount of a combination of tamoxifen and NDGA.

Another aspect of the invention is a formulation manufactured for the treatment of breast cancer specifically where the cancer has been shown to be resistant to tamoxifen, wherein the formulation comprises a therapeutically effective amount of a combination of tamoxifen and NDGA.

Another aspect of the invention is a method of treatment wherein a patient is treated with tamoxifen and found to be insufficiently responsive which treatment is followed by administration of both tamoxifen and NDGA.

Still yet another aspect of the invention is a kit comprised of tamoxifen. NDGA, and instructions with respect to the treatment of patients having estrogen receptor (ER) positive MCF-7 cells that overexpress HER2 (MCF-7/HER2-18).

These and other aspects of the invention will become apparent to those persons skilled in the art upon reading the details of the formulations and methods as more fully described below.

13B is a bar graph of results showing results wherein such cells were incubated in serum or a concentration of 10 nM IGF-1.

Figure 14:
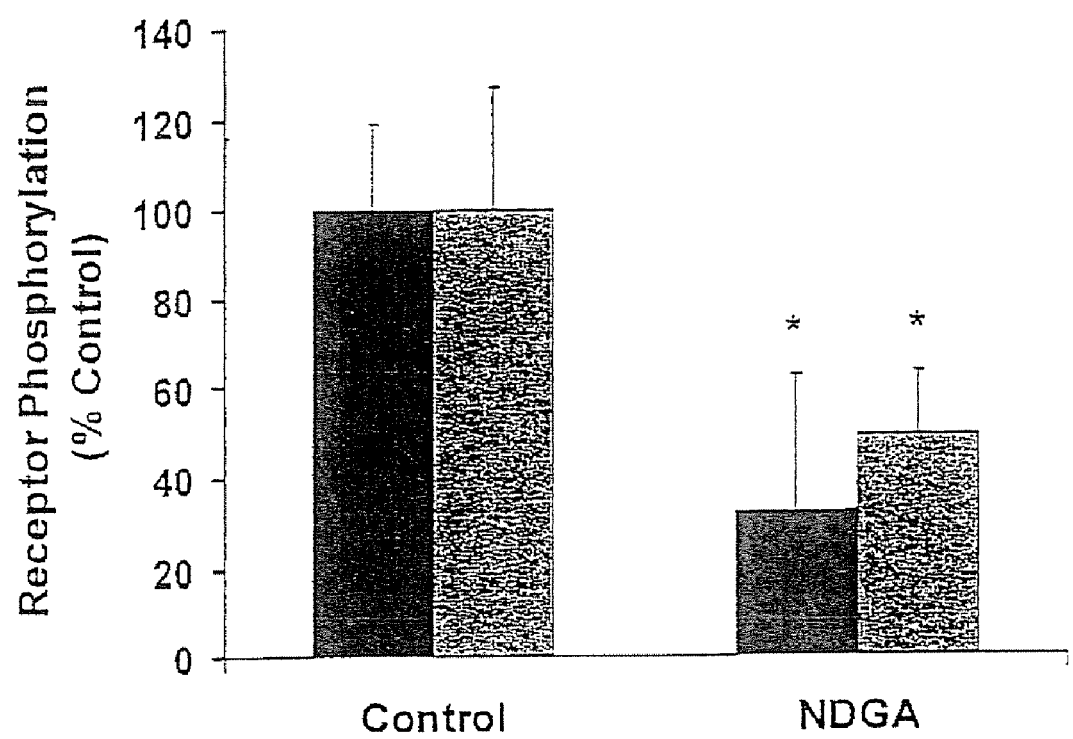

FIG. 14 is a bar graph showing results wherein NDGA was administered over a period of 21 days in vivo to MCNeuA tumors.

Figure 15:
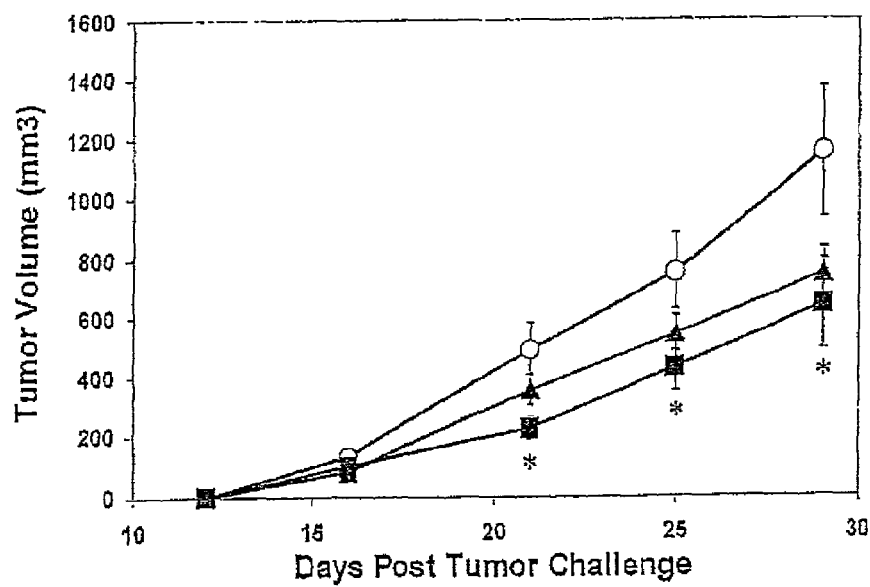

FIG. 15 is a graph showing the results of MDNeuA cells of a tumor being treated over a period of days with NDGA.

Figures 16A, 16B:
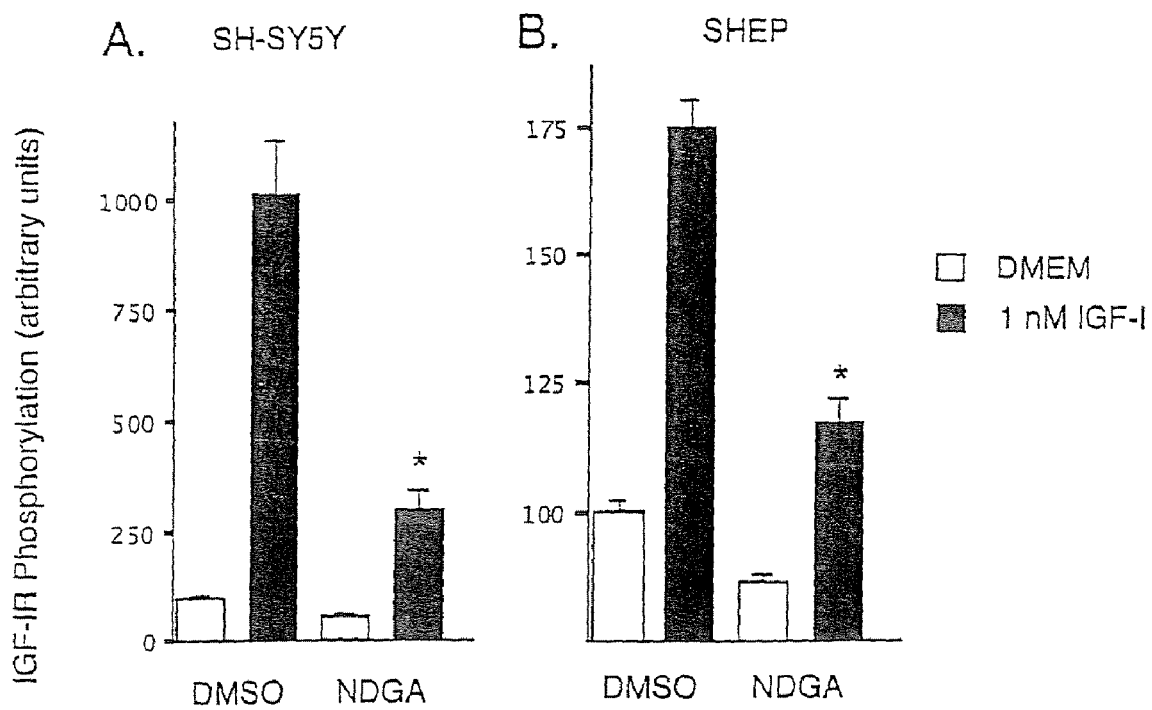

FIGS. 16A and 16B are each bar graphs showing the affect of DMSO and NDGA on neuroblastoma cells.

Figure 17A:
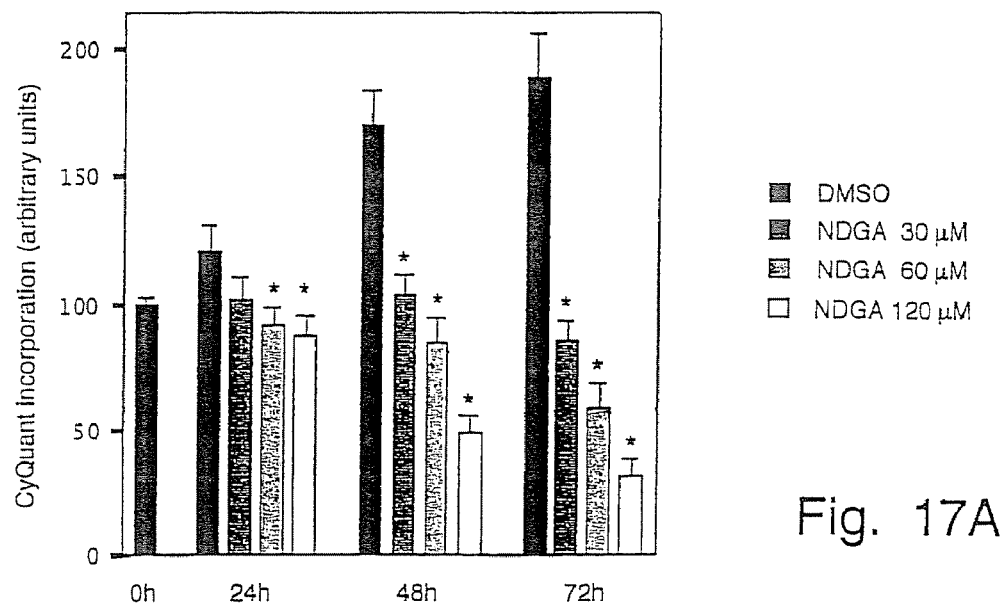
Figure 17B:
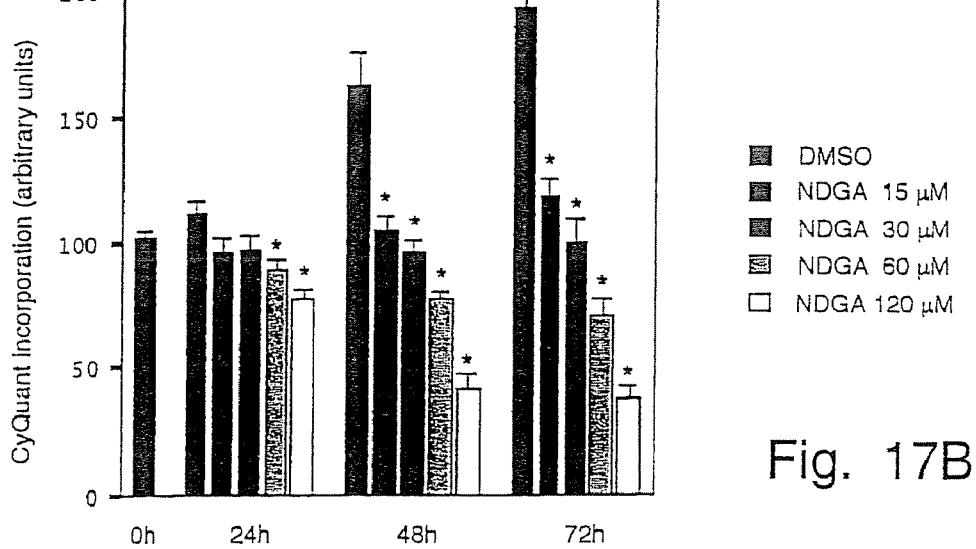

FIGS. 17A and 17B are each bar graphs showing the affect of DMSO and four different concentrations of NDGA on neuroblastoma cells.

Figure 18A:
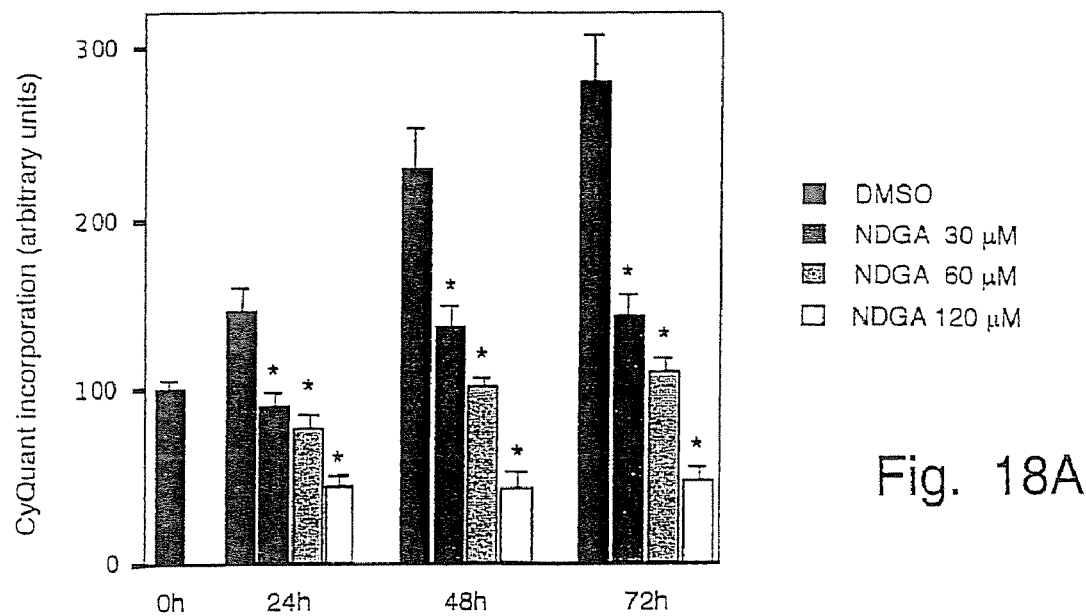
Figure 18B:
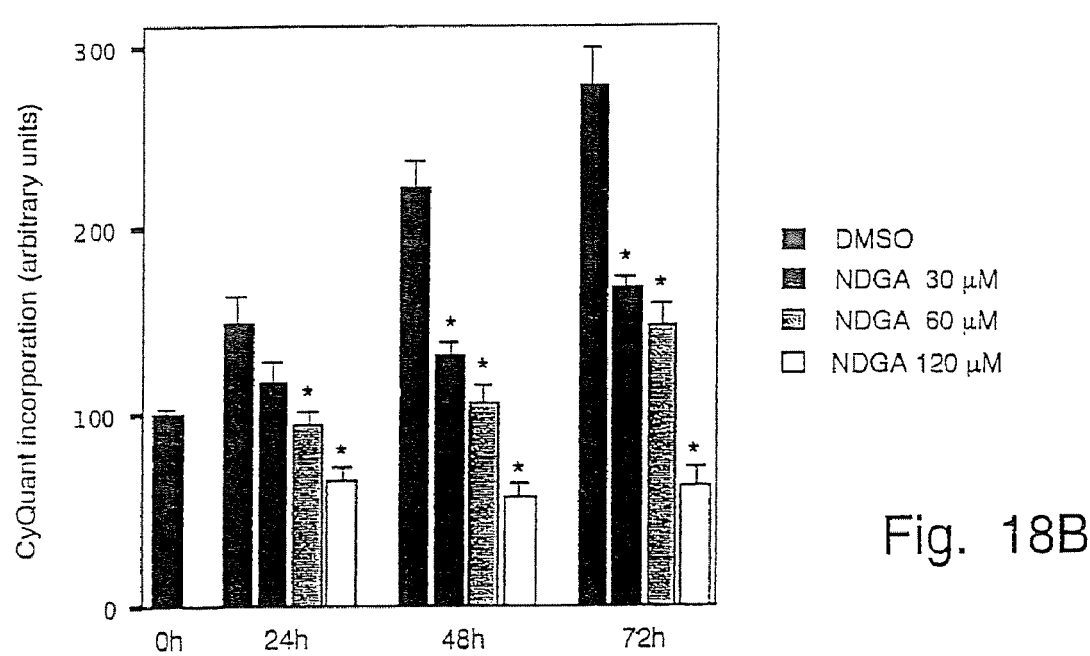

FIGS. 18A and 18B are each bar graphs showing the affect of DMSO and three different concentrations of NDGA on neuroblastoma cells.

Figure 19A:
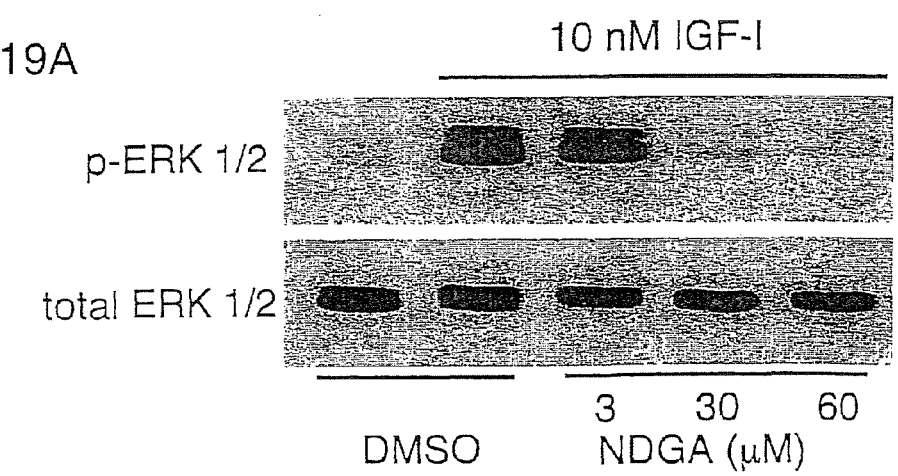
Figure 19B:
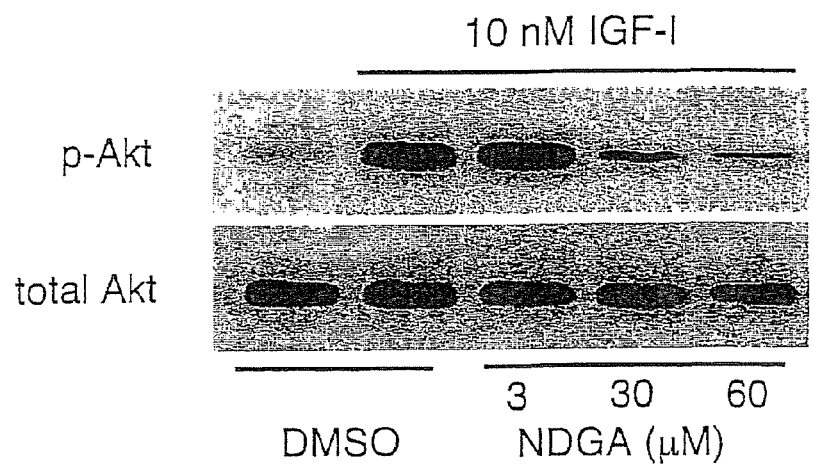

FIGS. 19A and 19B are each images of Western Blot analysis showing results obtained with DMSO and three different concentrations of NDGA.

Figure 20A:
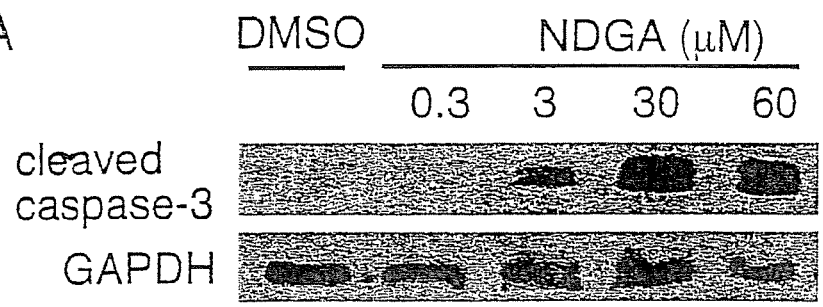
Figure 20B:
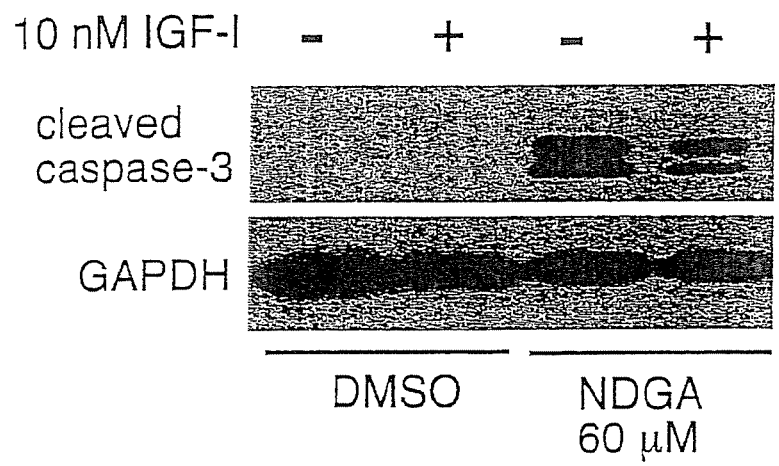
Figure 20C:
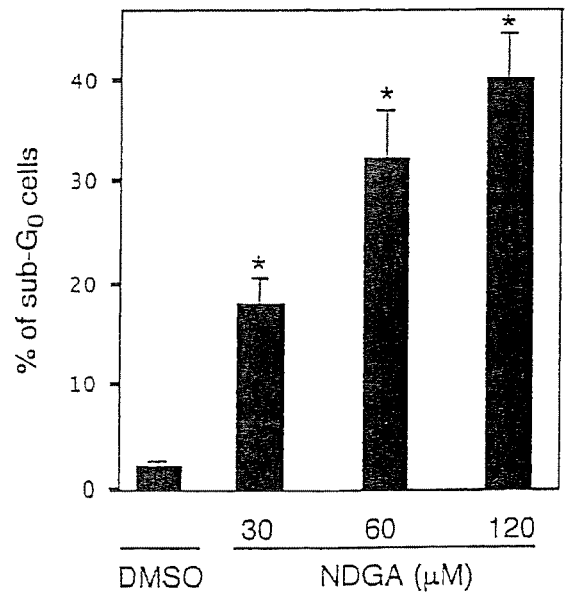

FIG. 20A is an image of a Western Blot showing the affects of DMSO and three different concentrations of NDGA. FIG. 20B is an image of a Western Blot showing the affects of DMSO and NDGA. FIG. 20C is a bar graph showing the results obtained using DMSO and NDGA in three different concentrations.

Figures 21A, 21B:
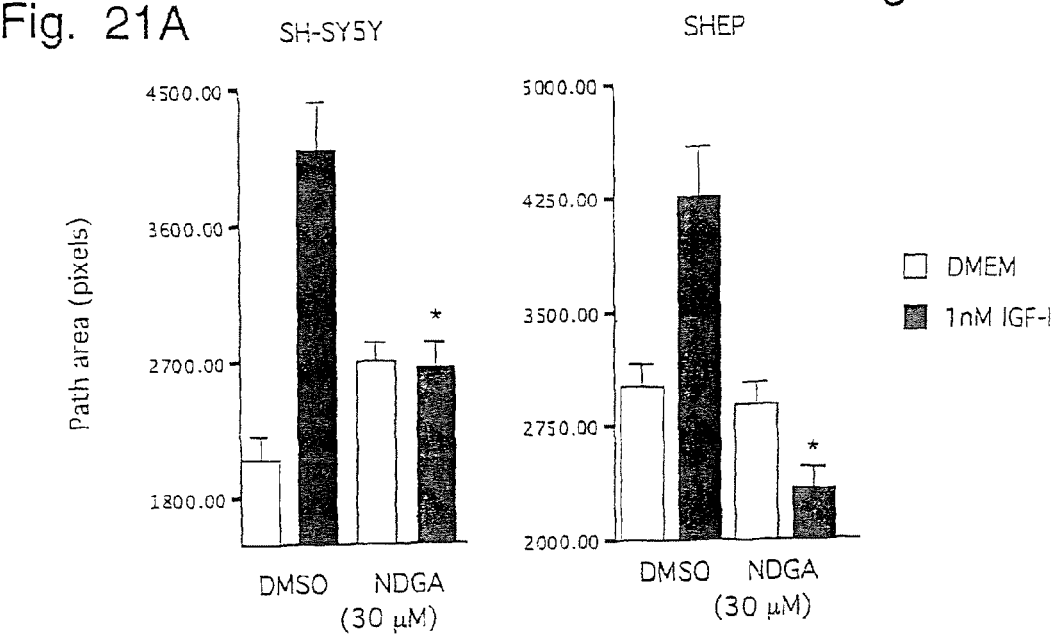
Figure 21C:
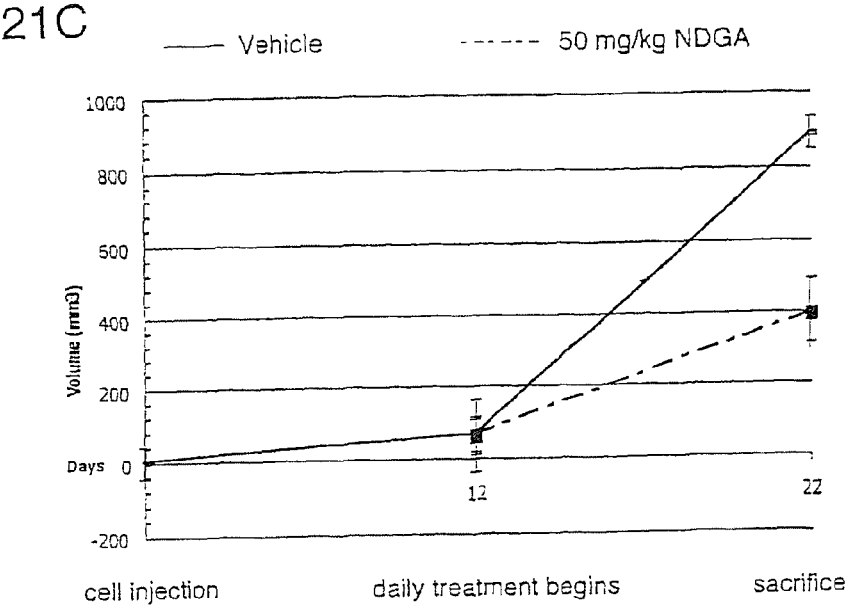

FIGS. 21A and 21B are each bar graphs showing the affects of DMSO and NDGA. FIG. 21C shows the affects of DMSO and NDGA used to treat mice by injection.

Figure 22:
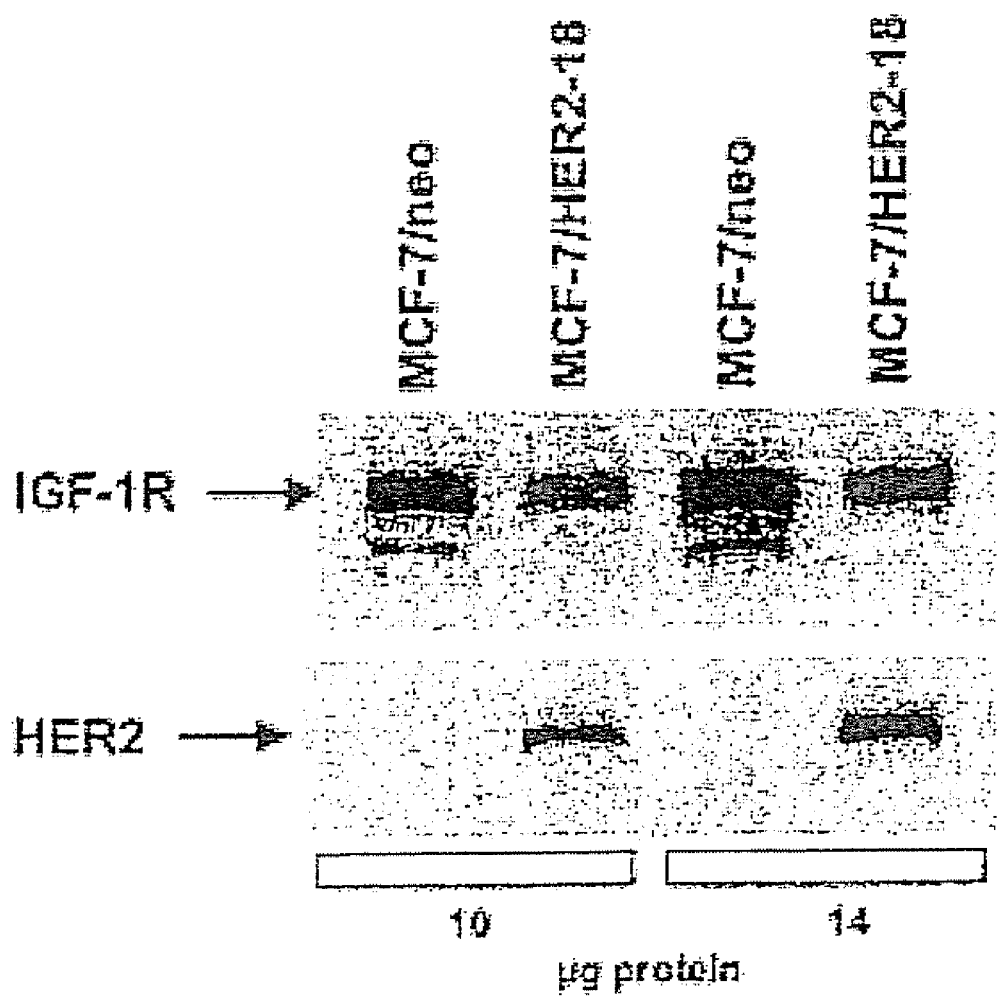

FIG. 22 shows gel images which show the expression of IGF-1R and HER2 in MCF-7/neo and MCF-7/HER2-18 cells. The gels were created using cell lysates which were separated by SDS-PAGE, transferred to nitrocellulose membranes, and probed with antibodies specific for IGF-1R and HER2. Two concentrations of total protein 10 μg and 14 μg were analyzed to confirm the linearity of the assay.

Figure 23A:
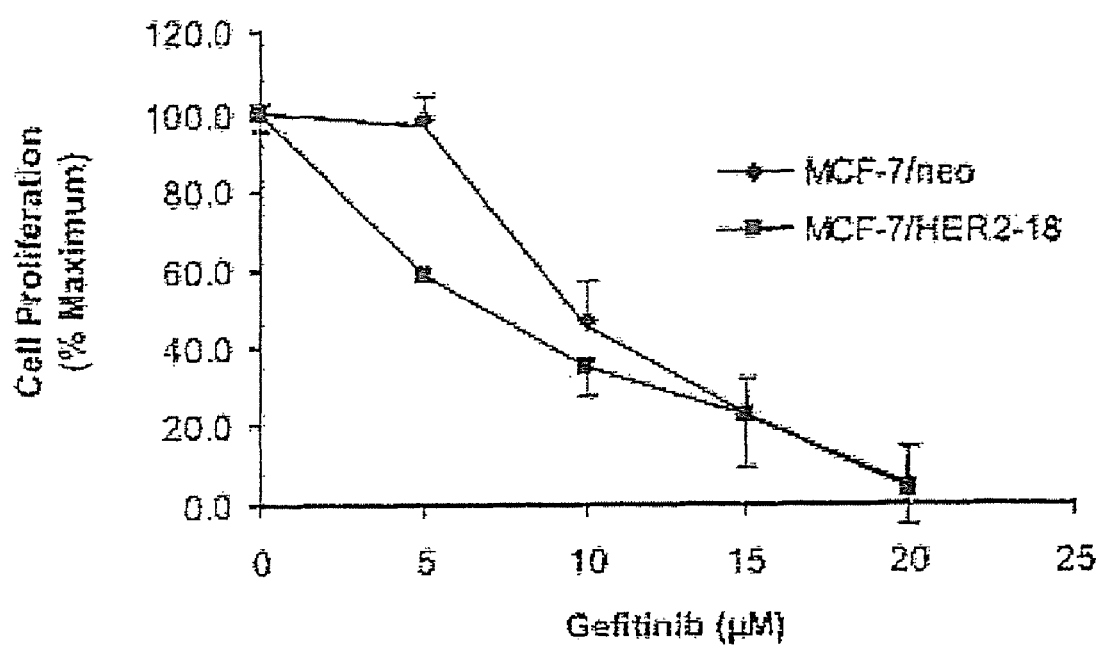
Figure 23B:
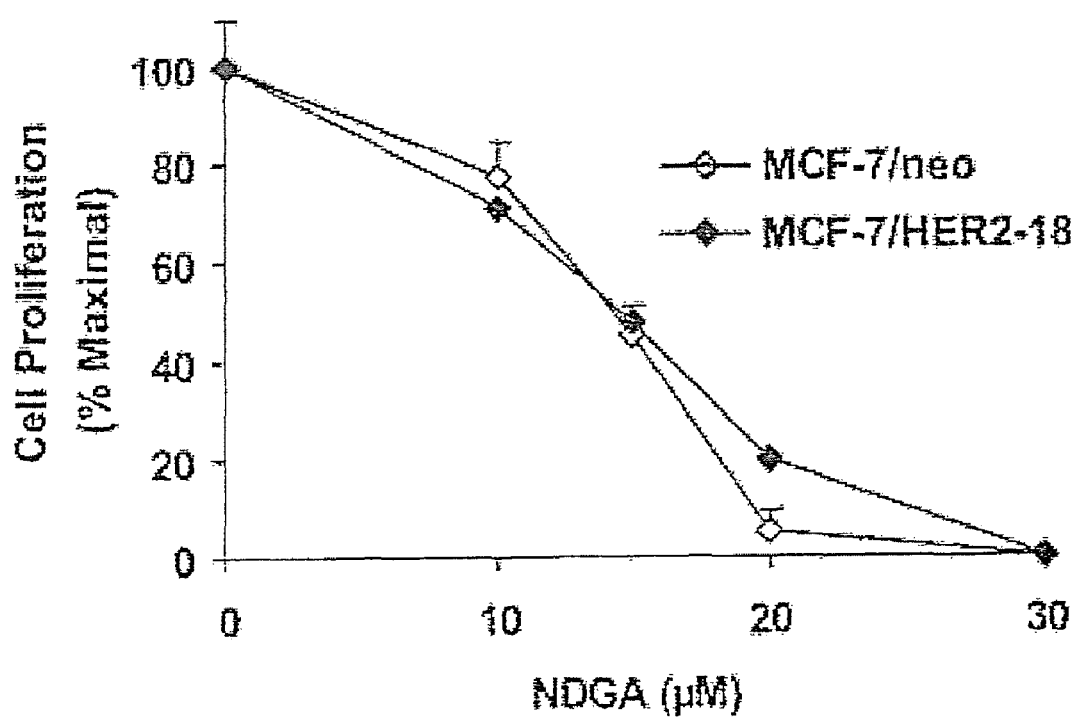

FIGS. 23A and 23B are each graphs which show the effects of gefitinib and NDGA on the growth of MCF-7/neo and MCF-7/HER2-18 cells. Cells were grown in the presence of various concentrations of gefitinib (23A) or NDGA (23B) for 6 days. Cell growth was assessed with a CyQuant cell proliferation assay. The results are expressed as mean±SEM of triplicate wells and are representative of three separate experiments.

Figure 24A:
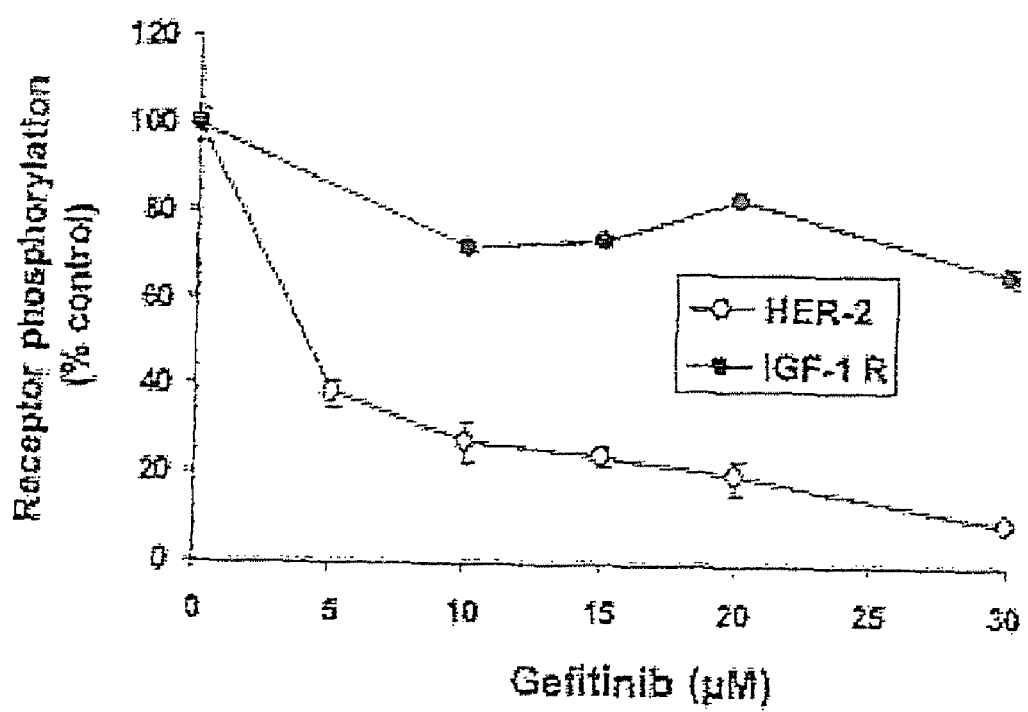
Figure 24B:
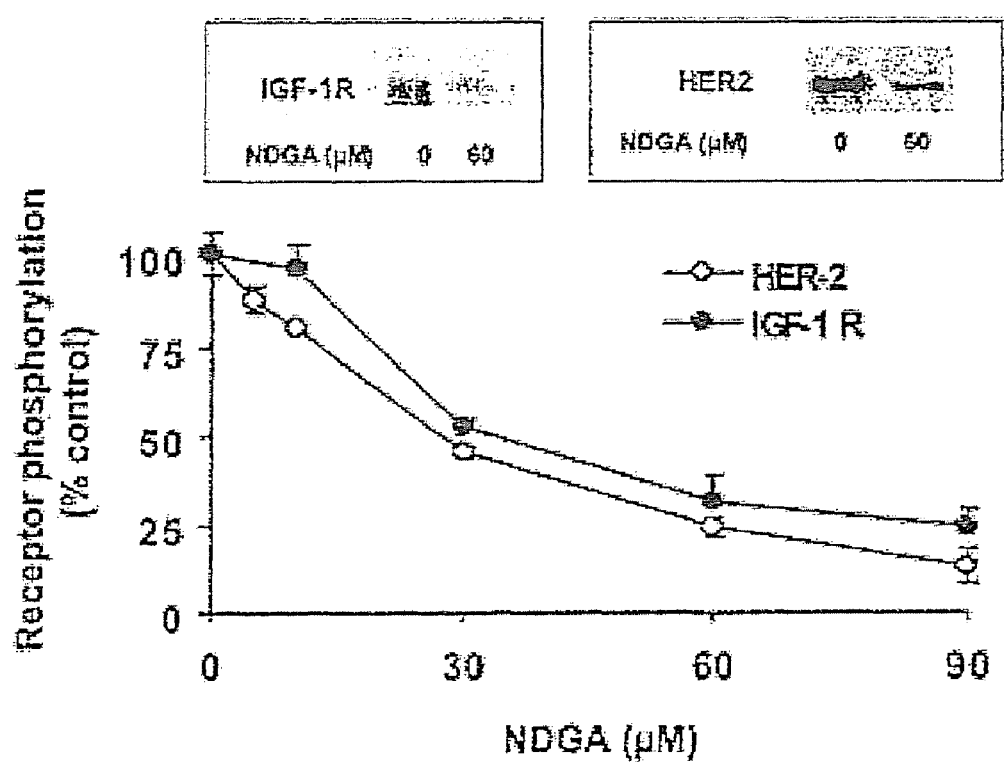

FIGS. 24A and 24B are each graphs which show the effects of gefitinib and NDGA on IGF-IR and HER2 phosphorylation in MCF-7/HER2-18 cells. Cells treated with various concentrations of gefitinib (A) or NDGA (B) were lysed and assayed for IGF-1R and HER2 phosphorylation by ELISA. For the IGF-1R ELISA, cells were stimulated with 3 nM IGF-I for 10 min. For the HER2 ELISA, cells were not stimulated. The results are expressed as mean±SEM of triplicate wells and are representative of three separate experiments. The effects of NDGA were confirmed by Western blot (panel B, inset) where phosphorylated IGF-IR and HER2 were detected with phospho-specific antibodies to pIGF-IR and pHER2, respectively.

Figure 25:
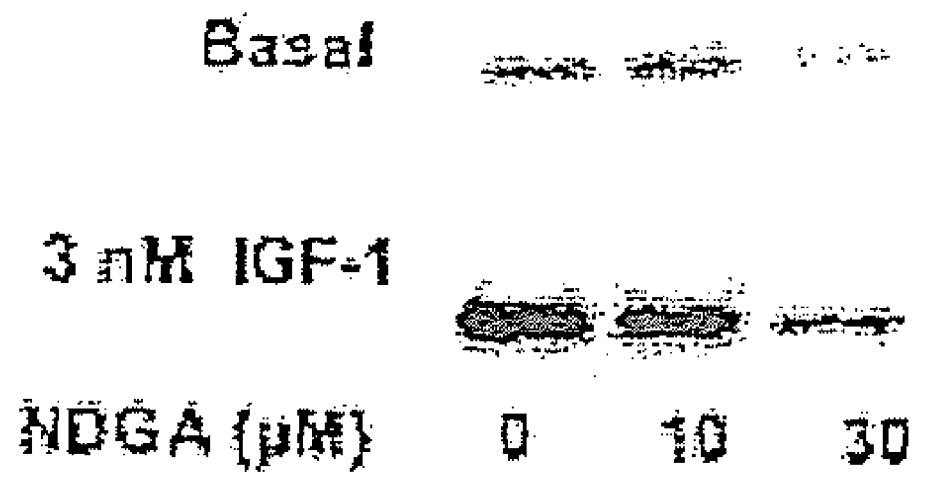

FIGS. 25 shows gel images which show the effect of NDGA on Akt/PKB phosphorylation. MCF-7/HER2-18 cells were incubated in the presence or absence of 3 nM IGF-1 for 10 min, with or without NDGA treatment. Cells lysates were prepared and separated by SDS-PAGE, transferred to nitrocellulose membranes, and probed with an anti-pAkt antibody.

FIGS. 26A, 26B, 26C and 26D are graphs which show the effects of combined treatment with tamoxifen and NDGA on the growth of MCF-7/neo and MCF-7/HER2-18 cells. MCF-7/neo (panels 26A and 26C) and MCF-7/HER2-18 (panels 26B and 26D) cells were incubated for 6 days with 100 nM tamoxifen, in the presence or absence of various concentrations of NDGA and cell growth was assessed with a CyQuant assay. Cell proliferation was expressed as a percentage of untreated control cells (mean±SEM) (panels 26A and 26B). Panels 26C and 26D express the results as percent growth inhibition.

Figure 27:
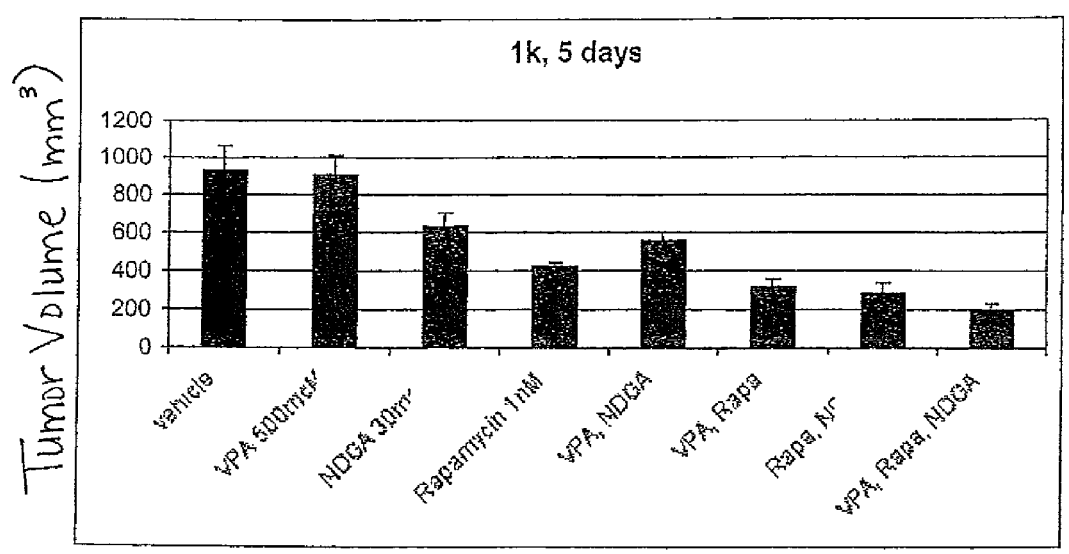

FIG. 27 is a graph which shows results where human breast cancer MCF-7 cells were grown for 5 days with medium plus 10% fetal calf serum and treated with the indicated concentrations of valproic acid (VAPA), nordihydroguaiaretic acid (NDGA), or rapamycin (RAPA). At the end of 5 days the cultures (in a 96 well plate) were assayed for total nucleic acid with a CyQuant dye based assay. Shown is the OD in this assay.

DETAILED DESCRIPTION OF THE INVENTION

Before the present compositions for and methods of treating cancer are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, potential and preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cancer cell" includes a plurality of such cancer cells and reference to "the methods of administration" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Figure 1:
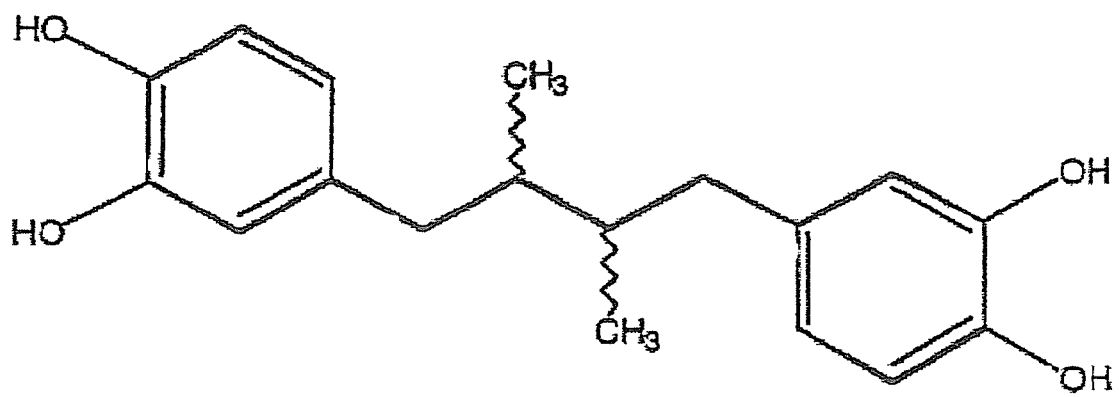
FIG. 1 shows the chemical structure of nordihydroguaiaretic acid (NDGA).

The term "nordihydroguaiaretic acid" is also referred to as "NDGA" and is the compound shown within the structure of FIG. 1 and see U.S. Pat. No. 2,644,822 incorporated here to disclosed NDGA as well as related compounds and their method of manufacture. It is pointed out that pharmaceutically acceptable salts and amines of the acid may be formed during use and are considered to be encompassed by the term unless specifically indicated otherwise.

The term tyrosine kinase receptor blocker and inhibitor of tyrosine kinase are used interchangeably to describe compounds which selectively and specifically bind to tyrosine kinase receptors. The binding preferably has an antagonist effect. Such compounds include compounds such as Her2 inhibitors, doxorubicin and Herceptin™.

The terms "treatment," "treating," and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. In general, methods of the invention involve treating diseases referred to as cancer and may be applied to a variety of different types of cancer by utilizing combinations of compounds such as tyrosine kinase receptor inhibitors which are known to bind to the receptor site. "Treatment" as used herein covers any treatment of such a disease in a mammal, particularly a human, and includes:

(a) preventing and/or diagnosing the disease in a subject which may be predisposed to the disease which has not yet been diagnosed as having it:

(b) inhibiting the disease, i.e. arresting its development; and/or (c) relieving the disease, i.e. causing regression of the disease.

The invention is directed towards treating patients with cancer and is particular directed towards treating particular types of cancer which are not generally treatable with normal surgical methods. More specifically, "treatment" is intended, in preferred circumstances, to mean providing a therapeutically detectable and beneficial effect on a patient suffering from cancer.

Formulations and Methods

Formulations of the invention combine compounds and excipients to obtain desirable results with respect to the biochemical inhibition of certain receptors. The compound such as nordihydroguaiaretic acid (NDGA), IGF-1 inhibitors and recombinant Her2 inhibitors as well as doxorubicin and Herceptin™ can be used in a pharmaceutically acceptable excipient carrier in various combinations. The combinations of the invention obtain a synergistic effect. This synergistic effect is specifically defined in connection with the present invention. Those skilled in the art will understand that the use of compound A to inhibit receptor X cannot be increased beyond certain points simply by adding more of compound A. At some point the effect of compound A is not increased by adding the amount or the increase is not practical in view of the toxic effects. Thus, the combination of "compound A" and "compound B" may be synergistic in blocking receptor "X" even when the combination of "A" and "B" is not additive in terms of blocking receptor "X". Obtaining a modest increase in the blockage of receptors without an increase in adverse effects or even with an acceptable level of adverse effects may be all that is necessary to effectively treat a given cancer.

Figure 3:
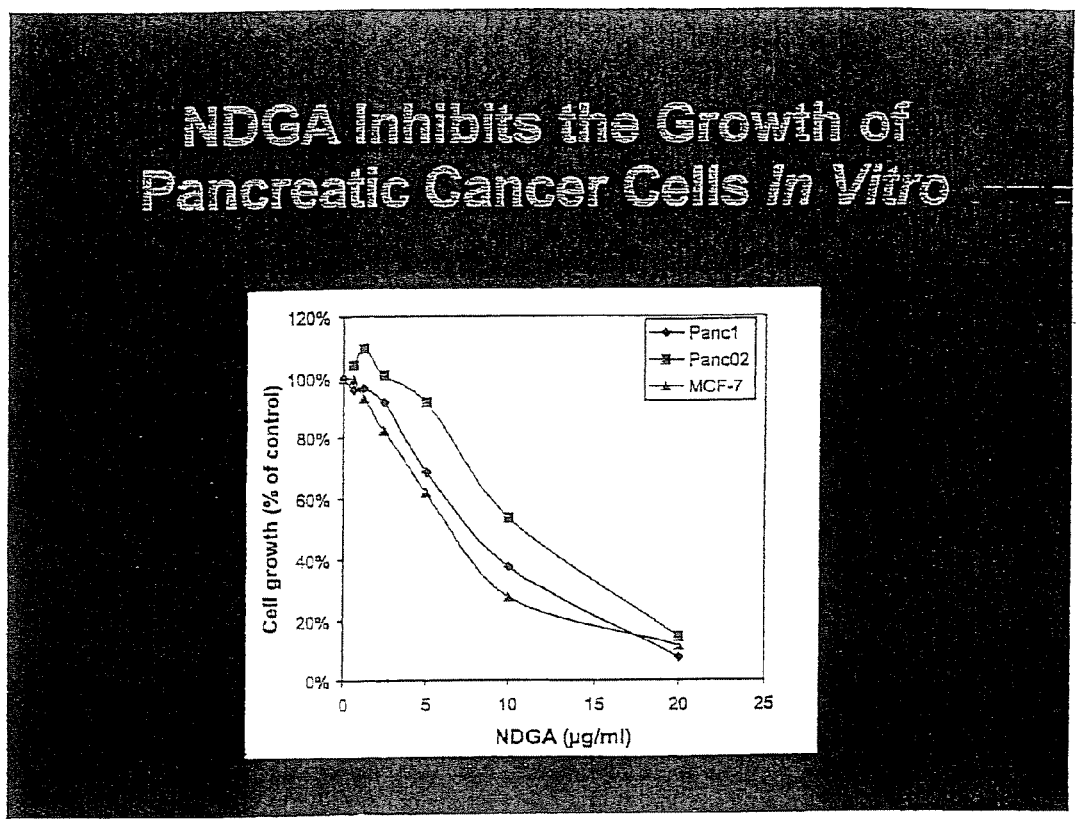
FIG. 3 is a graph showing the results of using NDGA to inhibit the growth of pancreatic cancer cells in vitro.
Figure 4A:
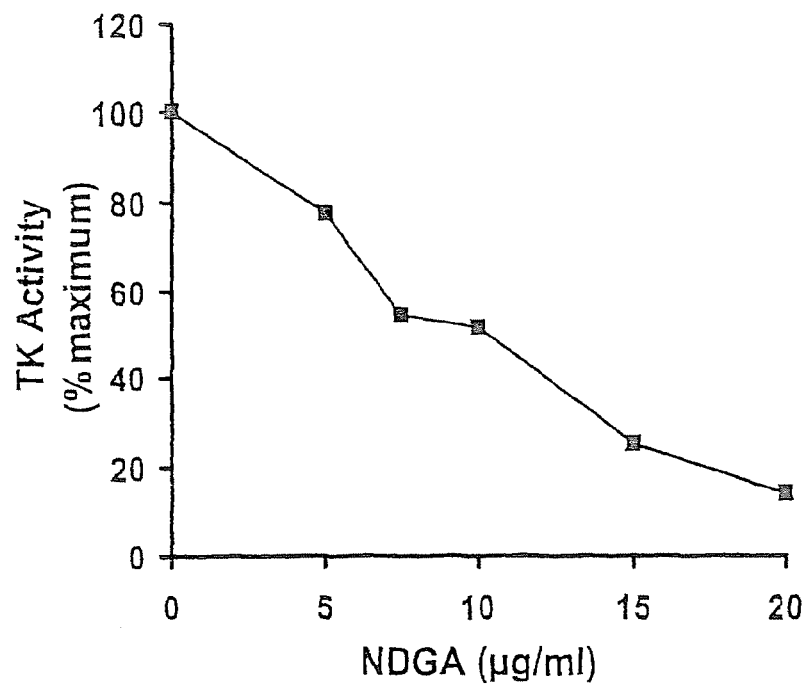
FIG. 4A is a graph showing the effectiveness of NDGA in inhibiting IGF-1 activation in pancreatic cancer cells.
Figure 4B:
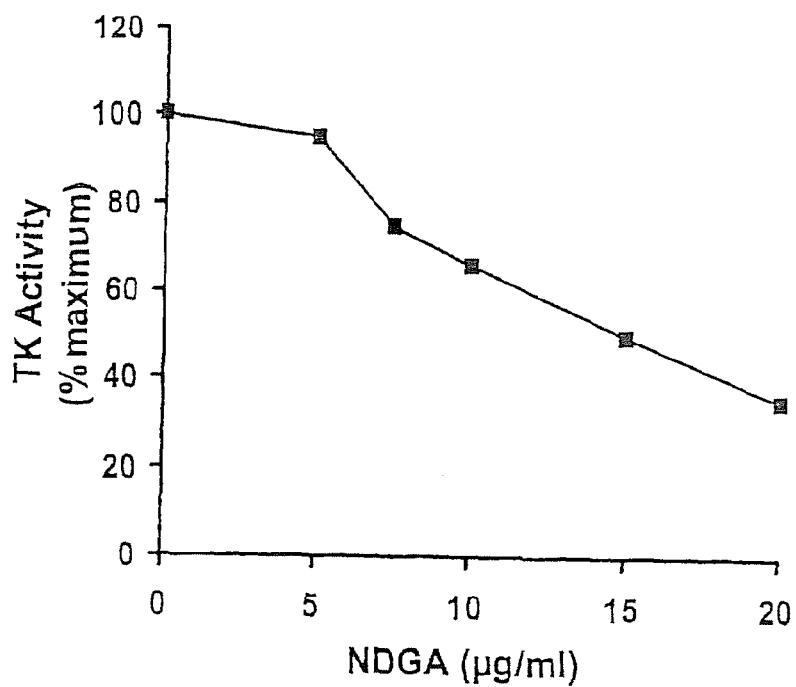
FIG. 4B is a graph showing the effectiveness of NDGA in inhibiting Her2/neu activation in pancreatic cancer cells.

Certain compounds may be used by themselves in particular dosage amounts and treatment regimes. For example, NDGA may be used in the treatment of pancreatic cancer. FIG. 3 shows the results of NDGA inhibiting the growth of pancreatic cancer cells in vitro. FIGS. 4A and 4B show the effectiveness of NDGA in inhibiting certain receptors. Specifically, FIG. 4A shows NDGA in micrograms per milliliter inhibiting Her2/NEU activation in pancreatic cancer cells. FIG. 4B shows NDGA being used in micrograms per milliliter inhibiting IGF-1 activation in pancreatic cancer cells.

Figure 5:
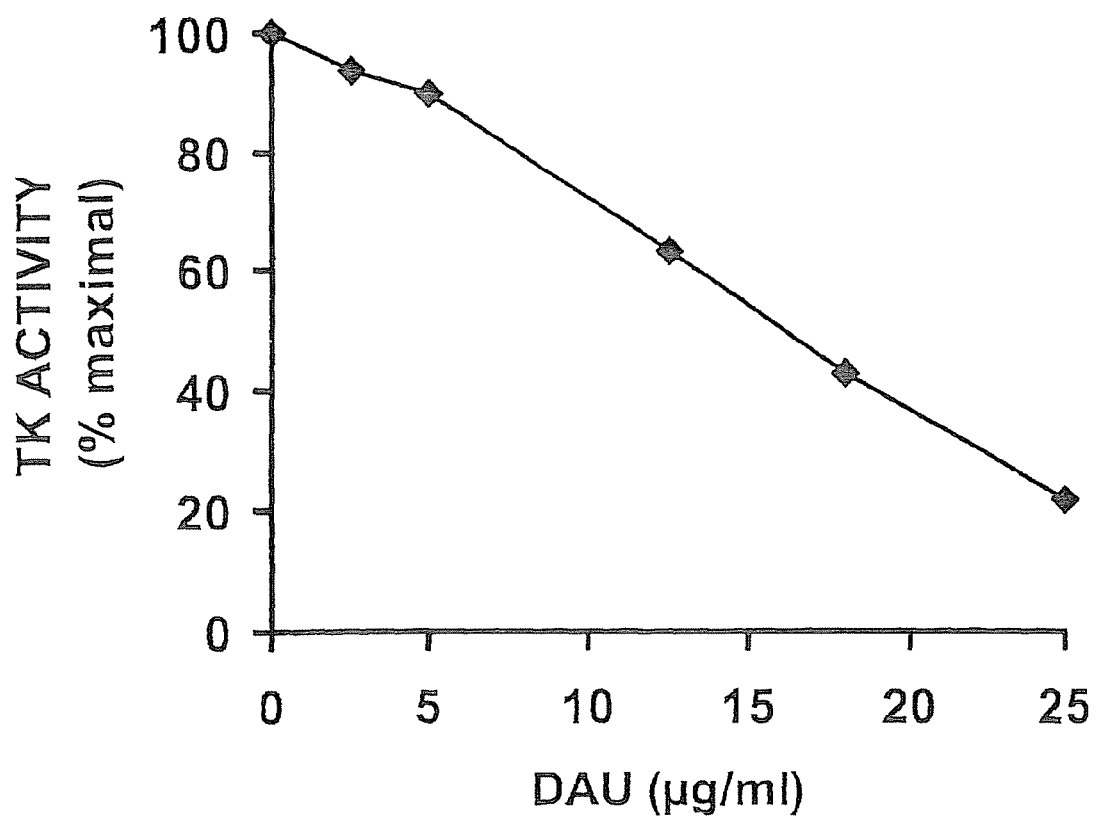
FIG. 5 is a graph showing that DAU inhibits tyrosine kinase activation in Panel pancreatic cancer cells.

FIG. 5 is a graph showing that DAU inhibits tyrosine kinase activation in Panc1 pancreatic cancer cells.

Figure 6A:
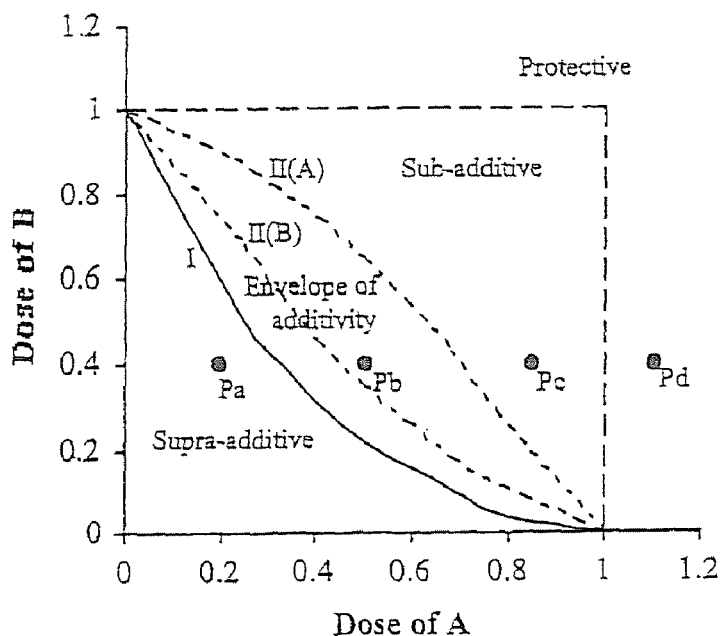
FIG. 6A is a schematic representation of an isobologram and FIG. 6B is a schematic representation of an isobologram analysis for DOX and NDGA on SKBR-3 cells.
Figure 6B:
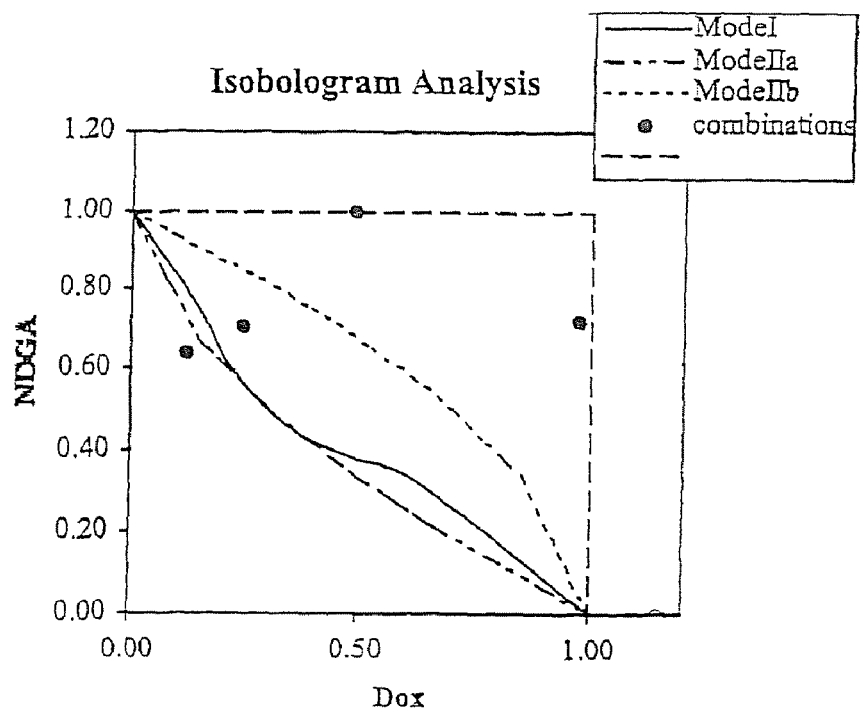

FIG. 6A is a schematic representation of an isobologram. The envelope of additivity, surrounded by Mode I (solid line) and Mode II (dotted lines) isobologram lines, is constructed from the dose-response curves of two drugs (A and B). The data points Pa, Pb, Pc and Pd, obtained from the combination dose-response curves of A and B, would classify the two-drug interactions as supra-additive (synergistic), additive, sub-additive and mutually protective, respectively. FIG. 6B is an isobologram analysis for DOX and NDGA on SKBR-3 cells. At low concentrations, the two compounds act synergistically.

When the combinations of drugs are used in accordance with the invention improved results of some manner are expected with respect to inhibiting the growth of cancer cells. FIG. 6A is a graph which schematically represents a basic concept behind an aspect of the invention. FIG. 6A shows an envelope of additivity for two drugs "A" and "B". As indicated in the graph the amount of drug:"B" increases in an upward direction along the "X" axis and the amount of drug "A" increases to the right along the "Y" axis. Using less drug is generally more desirable when the same amount of the drug can obtain the desired effect. Thus, the solid line and the area below the solid line represents a supra-additive effect.

Figure 7:
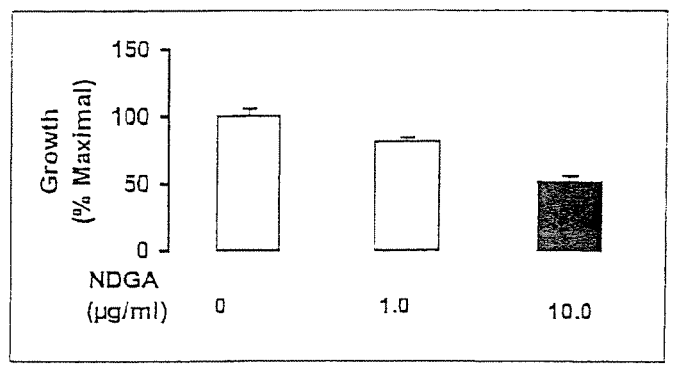
FIG. 7 is a bar graph showing the affect of different concentrations of NDGA on prostate cancer cells.

FIG. 7 is a bar graph showing the affect of NDGA on PC3 prostate cancer cell growth wherein the cells were plated at $10^5$ per well in the absence and presence of NDGA for four days with the results shown as the mean±SD4 triplicate determinations.

The present invention shows that NDGA is a direct inhibitor of both the IGF-1R and the HER2/neu receptor in isolated receptor preparations, cultured breast cancer cells, and tumors in vivo. Inhibition of these RTKs was accompanied by a reduction in cell growth both in cell culture and in vivo. The present invention demonstrates studies indicate that inhibition of RTKs has an important anti-tumor effect of NDGA.

The IGF-1R is an essential component of the transformation process and an attractive target for anti-cancer agents (Gross JM, Yee D: The type-1 insulin-like growth factor receptor tyrosine kinase and breast cancer: biology and therapeutic relevance. Cancer Metastasis Rev 22:327-336, 2003). Cells in tissue culture that lack the IGF-1R can not be transformed (Baserga R: Oncogenes and the strategy of growth factors. Cell 79:927-930, 1994). Following transformation, overexpression of IGF-1R is observed in many cell types (Rubin R. Baserga R: Insulin-like growth factor-I receptor. Its role in cell proliferation, apoptosis, and tumorigenicity. Lab Invest 73:311-331, 1995). In vivo, in primary breast tumors, the IGF-1R is overexpressed and hyperphosphorylated (Arteaga CL, Kitten LJ, Coronado EB, Jacobs S, Kull FC, Jr., Allred DC, Osborne CK: Blockade of the type I somatomedin receptor inhibits growth of human breast cancer cells in athymic mice. J Clin Invest 84:1418-1423, 1989). In vitro, in a variety of breast cancer cell lines, we have found that the IGF-1R is overexpressed (Sciacca L, Costantino A, Pandini G, Mineo R, Frasca F, Scalia P, Sbraccia P, Goldfine ID, Vigneri R, Belfiore A: Insulin receptor activation by IGF-II in breast cancers: evidence for a new autocrine/paracrine mechanism. Oncogene 18:2471-2479, 1999). In addition, there is strong evidence linking hyperactivation of the IGF- 1R with the early stages of breast cancer (Baserga R: The IGF-I receptor in cancer research. Exp Cell Res 253:1-6, 1999; Khandwala HM, McCutcheon IE, Flyvbjerg A, Friend KE: The effects of insulin-like growth factors on tumorigenesis and neoplastic growth. Endocr Rev 21:215-244, 2000; and Surmacz E: Function of the IGF-I receptor in breast cancer. J Mammary Gland Biol Neoplasia 5:95-105, 2000). Anti-proliferative effects against cultured breast cancer cells have been observed by employing antisense IGF-1R (Neuenschwander S, Roberts CT, Jr., LeRoith D: Growth inhibition of MCF-7 breast cancer cells by stable expression of an insulin-like growth factor I receptor antisense ribonucleic acid. Endocrinology 136:4298-4303, 1995), monoclonal antibodies (Sachdev D, Li SL, Hartell JS, Fujita-Yamaguchi Y, Miller JS, Yee D: A chimeric humanized single-chain antibody against the type I insulin-like growth factor (IGF) receptor renders breast cancer cells refractory to the mitogenic effects of IGF-I. Cancer Res 63:627-635, 2003; Arteaga CL, Osborne CK: Growth inhibition of human breast cancer cells in vitro with an antibody against the type I somatomedin receptor. Cancer Res 49:6237-6241, 1989), transfection with a dominant negative IGF-1R (Prager D, Li HL, Asa S. Melmed S: Dominant negative inhibition of tumorigenesis in vivo by human insulin-like growth factor I receptor mutant. Proc Natl Acad Sci USA 91:2181-2185, 1994), or small-molecule catechol mimics (Blum G, Gazit A, Levitzki A: Development of new insulin-like growth factor-1 receptor kinase inhibitors using catechol mimics. J Biol Chem 278: 40442-40454, 2003). Expressing dominant negative IGF-1R in breast cancer cells also inhibits tumor growth in vivo (Prager D, Li HL, Asa S, Melmed S: Dominant negative inhibition of tumorigenesis in vivo by human insulin-like growth factor I receptor mutant. Proc Natl Acad Sci USA 91:2181-2185, 1994).

HER2/neu has also emerged as an important target in breast cancer therapeutics. HER2/neu overexpression occurs in approximately half of DCIS cases, and 85-100% of high-grade, comedo-type DCIS, the lesions associated with the highest risk of progression (Wu Y, Tewari M, Cui S, Rubin R: Activation of the insulin-like growth factor-I receptor inhibits tumor necrosis factor-induced cell death. J Cell Physiol 168: 499-509, 1996; Prisco M, Hongo A, Rizzo MG, Sacchi A, Baserga R: The insulin-like growth factor I receptor as a physiologically relevant target of p53 in apoptosis caused by interleukin-3 withdrawal. Mol Cell Biol 17:1084-1092, 1997; and Tanno S, Tanno S, Mitsuuchi Y, Altomare DA, Xiao GH, Testa JR: AKT activation up-regulates insulin-like growth factor I receptor expression and promotes invasiveness of human pancreatic cancer cells. Cancer Res 61:589-593, 2001). The effectiveness of a monoclonal antibody that inhibits HER2/neu indicates the potential of this RTK as an anti-cancer target, although no small-molecule compounds specifically targeting HER2/neu with efficacy in vivo have been reported.

NDGA has previously been shown to reduce growth and induce apoptosis in a wide variety of cell lines including breast, lung, pancreas cancers (Moody TW, Leyton J. Martinez A, Hong S, Malkinson A, Mulshine JL: Lipoxygenase inhibitors prevent lung carcinogenesis and inhibit non-small cell lung cancer growth. Exp Lung Res 24:617-628, 1998; Chen X, Li N, Wang S, Hong J, Fang M, Yousselfson J., Yang P, Newman RA, Lubet RA, Yang CS: Aberrant arachidonic acid metabolism in esophageal adenocarcinogenesis, and the effects of sulindac, nordihydroguaiaretic acid, and alpha-difluoromethylornithine on tumorigenesis in a rat surgical model. Carcinogenesis 23:2095-2102, 2002; Hausott B, Greger H, Marian B: Naturally occurring lignans efficiently induce apoptosis in colorectal tumor cells. J Cancer Res Clin Oncol 129:569-576, 2003; Wagenknecht B, Schulz JB, Gulbins E, Weller M: Crm-A, bcl-2 and NDGA inhibit CD95L-induced apoptosis of malignant glioma cells at the level of caspase 8 processing. Cell Death Differ 5:894-900, 1998; Schultze-Mosgau MH, Dale IL, Gant TW, Chipman JK, Kerr DJ, Gescher A: Regulation of c-fos transcription by chemopreventive isoflavonoids and lignans in MDA-MB-468 breast cancer cells. Eur J Cancer 34:1425-1431, 1998), but its anti-tumor action has not been defined. The principal finding of the present study is therefore the attribution of the described anti-cancer actions to the ability of NDGA to inhibit cellular RTK activity. The ability of NDGA to inhibit growth in normal culture conditions is consistent with studies employing specific inhibition of IGF-1R signaling by antibody or molecular techniques (Neuenschwander S, Roberts CT, Jr., LeRoith D: Growth inhibition of MCF-7 breast cancer cells by stable expression of an insulin-like growth factor I receptor antisense ribonucleic acid. Endocrinology 136:4298-4303, 1995; Arteaga CL, Osborne CK: Growth inhibition of human breast cancer cells in vitro with an antibody against the type I somatomedin receptor. Cancer Res 49:6237-6241, 1989). In addition, we have demonstrated that NDGA was more effective at inhibiting growth stimulated solely by IGF-1 than at inhibiting growth stimulated by the complex milieu provided by fetal calf serum, or growth in the absence of all exogenous growth factors. These results suggest that inhibition of the IGF-1R comprises a major component of the anti-mitogenic effects of NDGA in cell culture. The findings that NDGA inhibition of the IGF-1R produces a subsequent reduction in phosphorylation of the serine kinase Akt/PKB, and of the pro-apoptotic protein BAD, provide evidence that the described apoptotic effects of NDGA treatment result directly from an inhibition of the cell survival pathway regulated by the IGF-1R.

We also found that NDGA was able to reduce phosphorylation of the IGF-1R and HER2/neu in tumors in vivo. This action against these RTKs was associated with significant reductions in tumor cell growth. While other studies have demonstrated the effectiveness of NDGA against xenograft models of pancreatic and non-small cell lung cancer (Tong WG, Ding XZ, Witt RC, Adrian TE: Lipoxygenase inhibitors attenuate growth of human pancreatic cancer xenografts and induce apoptosis through the mitochondrial pathway. Mol Cancer Ther 1:929-935, 2002; Moody TW, Leyton J, Martinez A, Hong S, Malkinson A, Mulshine JL: Lipoxygenase inhibitors prevent lung carcinogenesis and inhibit non-small cell lung cancer growth. Exp Lung Res 24:617-628, 1998), in the present study we were able to demonstrate that chronic treatment of tumor-bearing mice resulted in a reduction in the normal, physiological activation state of both IGF-1 and c-erbB2/HER2/neu receptors. This effect was observed 16 hours after treatment, and is unlikely to be the result of an acute effect of the previous injection. Thus, we believe that the RTK-inhibitory actions of NDGA contribute greatly to its in vivo anti-cancer properties as well.

The terminal half-life for a single injection of NDGA is reported to be 135 minutes (Lambert JD, Meyers RO, Timmermann BN, Dorr RT: Pharmacokinetic analysis by high-performance liquid chromatography of intravenous nordihydroguaiaretic acid in the mouse. J Chromatogr B Biomed Sci Appl 754:85-90, 2001), although the half-life in tissues as well as the potency of potential metabolites of NDGA are unknown. Although extracts of the creosote bush have demonstrated toxic effects (Arteaga S, Andrade-Cetto A, Cardenas R: *Larrea tridentata* (Creosote bush), an abundant plant of Mexican and US-American deserts and its metabolite nordihydroguaiaretic acid. J Ethnopharmacol 98:231-239, 2005), Pure NDGA itself has minimal toxicity, has passed FDA approved pre-clinical trials and is available for administration to humans (G. Kelly, Insmed Inc., Glen Allen, Va., personal communication).

The mechanism whereby NDGA inhibits RTK activity has not yet been elucidated. Most small-molecule RTK inhibitors are competitive inhibitors of ATP binding (Morin MJ: From oncogene to drug: development of small molecule tyrosine kinase inhibitors as anti-tumor and anti-angiogenic agents. Oncogene 19:6574-6583, 2000), as is a recently reported IGF-1R-specific inhibitor (Mitsiades CS, Mitsiades NS, McMullan CJ, Poulaki V, Shringarpure R, Akiyama M, Hideshima T, Chauhan D, Joseph M, Libermann TA, Garcia-Echeverria C, Pearson MA, Hofmann F, Anderson KC, Kung AL: Inhibition of the insulin-like growth factor receptor-1 tyrosine kinase activity as a therapeutic strategy for multiple myeloma, other hematologic malignancies, and solid tumors. Cancer Cell 5:291-230, 2004: Garcia-Echeverria C, Pearson MA, Marti A, Meyer T, Mestan J, Zimmermann J, Gao J, Brueggen J, Capraro HG, Cozens R, Evans DB, Fabbro D, Furet P, Porta DG, Liebetanz J. Martiny-Baron G, Ruetz S, Hofmann F: In vivo antitumor activity of NVP-AEW541-A novel, potent, and selective inhibitor of the IGF-IR kinase. Cancer Cell 5:231-239, 2004). However, NDGA does not share general structural homology with ATP analogs. Interestingly, Blum et al. (Blum G. Gazit A, Levitzki A: Substrate competitive inhibitors of IGF-1 receptor kinase. Biochemistry 39:15705-15712, 2000; Blum G, Gazit A, Levitzki A: Development of new insulin-like growth factor-1 receptor kinase inhibitors using catechol mimics. J Biol Chem 278: 40442-40454, 2003) have investigated a compound that appears to inhibit IGF-1R signaling by competing with the autophosphorylation sites on the β-subunit of the IGF-1R. This compound was effective in inhibiting the growth of breast cancer cells in culture. Interestingly, the di-catechol structure investigated by this group shares considerable structural homology with NDGA, differing only in length of the carbon chain linking the two catechol rings. Modeling data generated by these investigators with the closely related IR suggest that their lead compound competes for binding with the tyrosine substrates at the kinase active site (Blum G, Gazit A. Levitzki A: Substrate competitive inhibitors of IGF-1 receptor kinase. Biochemistry 39:15705-15712, 2000). It is unclear however whether NDGA interacts with a homologous site on either IGF-1R or HER2/neu. The ability of NDGA to inhibit autophosphorylation of intrinsically active HER2/neu suggests that this compound acts directly on the enzymatic components of the receptors and not by interfering with either ligand binding or binding-dependent conformational changes. Thus, NDGA may represent a potential new class of agents for the treatment of breast and other cancers where the IGF-1R and/or HER2/neu play a role in the oncogenic process.

Treating Neuroblastoma

Neuroblastoma is a common pediatric malignancy that metastasizes to the liver, bone, and other organs, and is often resistant to available treatments. Insulin-like growth factors (IGFs) stimulate neuroblastoma growth, survival, and motility, and are expressed by neuroblastoma cells and the tissues they invade. Administration of formulations of the invention disrupt the effects of IGFs on neuroblastoma tumorigenesis and thereby slow disease progression. Nordihydroguaiaretic acid (NDGA), a phenolic compound isolated from the creosote bush (Larrea divaricatta), has anti-tumor properties against a number of malignancies. NDGA inhibits the phosphorylation and activation of the Her2/neu and IGF-I receptors (IGF-IR). The present invention shows that NDGA inhibits IGF-I-mediated activation of the IGF-IR in human neuroblastoma cell lines. NDGA inhibits neuroblastoma growth and disrupts activation of ERK and Akt signaling pathways induced by IGF-I. NDGA induces apoptosis at higher doses, causing IGF-I-resistant activation of caspase-3 and a large increase in the fraction of sub-$G_0$ cells. NDGA inhibits the growth of xenografted human neuroblastoma tumors in nude mice by 50%. The results provided show that small molecules that prevent activation of the IGF-1R, such as NDGA, are useful in the treatment of neuroblastoma.

Neuroblastoma affects an estimated 1 in 7000 children under age 15 (Carlsen NL. Neuroblastoma: epidemiology and pattern of regression. Problems in interpreting results of mass screening. Am J Pediatr Hematol Oncol 1992;14:103-110), making it the second most common solid tumor in children. Neuroblastoma tumors are believed to arise from neural crest cells in the adrenal gland and spinal ganglia. Neuroblastoma often regresses spontaneously in children under 1 year of age, but neuroblastoma in older children is difficult to treat with conventional radiation and chemical therapies (Philip T. Overview of current treatment of neuroblastoma. Am J Pediatr Hematol Oncol 1992;14:97-102). Metastasis to bone, meninges, the liver, and other organs contributes to the difficulty in eliminating the disease.

The development of effective treatments for neuroblastoma is hampered by an incomplete understanding of the factors that lead to neuroblastoma tumorigenesis, although several key abnormalities are associated with a significant subset of aggressive tumors. Although several chromosomal abnormalities have been described, amplification of MYCN is still the best understood genetic abnormality and is associated with advanced disease.

While a primary defect in growth factor signaling has not been observed in neuroblastoma, growth factor responsiveness is believed to support tumor growth, survival, and invasiveness. Thus, therapeutic approaches that disrupt growth factor signaling may have an impact on disease progression. Recently, nordihydroguaiaretic acid (NDGA), a naturally occuring compound isolated from creosote (Larrea divaricata), was found to inhibit the activation of partially purified insulin-like growth factor I (IGF-I) and her2/neu receptor tyrosine kinases.

NDGA has been extensively studied as an inhibitor of arachidonic acid metablolism, where it blocks lipoxygenase activity, but its ability to inhibit receptor tyrosine kinase activation was previously unappreciated. In breast cancer cells, NDGA inhibited ligand activation of the IGF-I and her2/neu receptors and subsequent activation of signaling intermediates downstream of these receptors. Both the in vitro and in vivo growth of breast cancer cells is inhibited by NDGA, potentially via its ability to suppress responsiveness to growth factors.

IGF-I and II are peptide growth factors that regulate cell mitogenesis and survival. IGFs bind to the tyrosine kinase IGF-I receptor (IGF-1R), causing receptor autophosphorylation that initiates the mitogen activated protein kinase (MAPK) and phosphatidylinositol 3-kinase (PI-3K) signaling pathways. MAPK regulates mitogenesis (De Meyts P, Wallach B, Christoffersen CT, et al. The insulin-like growth factor-I receptor. Structure, ligand-binding mechanism and signal transduction. Horm Res 1994;42:152-169), while PI-3K activates targets that impact apoptosis, such as Akt (Fresno Vara JA, Casado E, de Castro J, Cejas P, Belda-Iniesta and Gonzalez-Baron M. PI3K/Akt signaling pathway and cancer. Cancer Treat Rev 2004;30:193-204).

IGFs promote neuroblastoma tumorigencity by stimulating proliferation, inhibiting apoptosis, and stimulating motility. IGFs are expressed in all neuroblastoma tumor stages and in neuroblastoma tumor lines (Martin DM, Yee D, Carlson RO and Feldman EL. Gene expression of the insulin-like growth factors and their receptors in human neuroblastoma cell lines. Brain Res Mol Brain Res 1992;15:241-246), and can act as either autocrine or paracrine mitogens (Martin DM and Feldman EL. Regulation of insulin-like growth factor-II expression and its role in autocrine growth of human neuroblastoma cells. J Cell Physiol 1993;155:290-300). IGF-I and IGF-IR expression prevent neuroblastoma cells from undergoing apoptosis (Singleton JR, Dixit VM and Feldman EL. Type I insulin-like growth factor receptor activation regulates apoptotic proteins. J Biol Chem 1996;271:31791-31794) by regulating the activity of caspases and Bcl proteins. IGFs also regulate the metastatic capabilities of neuroblastoma cells by stimulating actin polymerization, lamellipodium extension, and motility.

The present invention is based, in part, on an understanding of the ability of NDGA to inhibit growth and IGF-IR-related signaling events in breast cancer. The present invention shows the anti-tumor effects of NDGA in three human neuroblastoma cell lines. Results provided here quantify IGF-I- and serum-dependent growth of neuroblastoma cells treated with NDGA, and characterize IGF-I-dependent phosphorylation of IGF-IR, extracellular regulated kinases (ERKs), and Akt in the presence of NDGA. Results provided here show that IGF-IR blockade mediated by NDGA resulted in decreased proliferation, increased apoptosis, decreased motility, and decreased tumor growth in xenograft models. Further, the results provided here show that NDGA is a potent inhibitor of neuroblastoma growth and survival, and of IGF-I-stimulated signaling events associated with tumorigenesis in neuroblastoma.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Breast Cancer

Materials and Methods

Materials.

NDGA and IGF-1 were gifts from Insmed Inc. (Glen Allen, Va.). IGF-1R kinase domain peptide was obtained from Upstate, USA (Charlottesville, Va.). Antibodies against the IGF-1R (C-20), HER2/neu (C-18), and phosphospecific antibodies recognizing phosphotyrosine (PY20), phosphoBAD (ser136), and pNeu (Tyr1248), and HRP-conjugated antiphosphotyrosine antibody (PY20HRP) were obtained from Santa Cruz Biotechnology (Santa Cruz, Calif.). αIR3, a monoclonal antibody against the IGF-1R, was obtained from CalBiochem (San Diego, Calif.), and the phosphospecific antibody pAkt(ser473) was obtained from Cell Signaling (Beverly, Mass.). All other reagents were from Sigma (St. Louis. Mo.), except as indicated below.

IGF-1R Peptide Autophosphorylation.

1 µg of IGF-1R kinase domain peptide was incubated +/- varying concentrations of NDGA in 2% DMSO in 40 mM Tris, pH 7.4, 80 µM EGTA, 0.25% 2-mercaptoethanol, 80 µM $Na_3VO_4$, 10 mM $MgCl_2$, and 2 mM $MnCl_2$ for 20 min. ATP was then added at a final concentration of 20 µM. Autophosphorylation of peptide was allowed to occur for 20 min at 22° C. The reaction was stopped by the addition of SDS-reducing buffer, and the samples were run on SDS-PAGE. Following transfer to nitrocellulose membrane, peptide autophosphorylation was determined by western blotting employing an antibody against phosphotyrosine diluted to 0.5 µg/ml in phosphate buffered saline (PBS) containing 3% milk. The membrane was incubated with the antibody overnight at 4 C. Next, blots were washed 3 times with PBS, then incubated with HRP conjugated sheep anti-rabbit IgG (Amersham, Piscataway, N.J.) diluted 1:50,000 in PBS with 3% milk for 90 minutes at room temperature. After washing, blots were incubated with Super-Signal (Pierce, Rockford, Ill.), and exposed to film. Values were determined by scanning densitometry.

Preparation of Partially Purified RTKs by Wheat Germ Agglutin (WGA)-Chromatography.

IGF-1 and HER2/neu receptors were partially purified by WGA chromatography of cells overexpressing the protein of interest. To isolate IGF-1R, CHO cells transfected with and overexpressing the human IGF-1R (CHOIGF-1R) were plated in T-150 flasks and grown in DMEM supplemented with 10% fetal calf serum (FCS) until 80% confluent. Cells were harvested in the basal state and solubilized in 50 mM HEPES, 10% glycerol, 1% Triton X-100, 150 mM NaCl, 5 µM EGTA, 0.24 mg/ml aminoethyl-benzensulfonyl fluoride (AEBSF), 10 µg/ml aprotinin, 25 mM benzamidine, 10 µg soybean trypsin inhibitor, and 5 µg/ml leuptin for one hour at 4° C. Samples were centrifuged for 60 minutes at 100,000 g and solubilized extract collected. Rodent HER2/neu receptors were collected from MCNeuA cells crown under identical conditions and processed similarly. Lysates from both cell lines were loaded onto a 1 ml wheat germ agglutin (WGA) column (Pharmacia, Piscataway, N.J.), washed with WGA buffer (50 mM HEPES pH 7.6, 150 mM NaCl, 0.1% Triton X-100, 1 mg/ml bacitracin, and 1 mM PMSF). Receptors were then eluted with WGA buffer supplemented with 0.3 N N-Acetyl-D-glucosamine. WGA fractions containing RTK of interest were determined by SDS page and a western blot that employed antibodies against either the IGF-1R or HER2/neu as appropriate.

Determination of the Effects of NDGA on the Tyrosine Kinase Activity of Partially Purified IGF-1R.

The effects of NDGA on the ability of the IGF-1R to phosphorylate exogenous substrates were determined by ELISA. Tyrosine kinase substrate poly Glu4:Tyr1 (PGT) was coated on Nunc-Immuno 96-well plate at 500 ng/well over night at 4 C. The plate was washed and blocked with Superblock (Pierce, Rockford, Ill.) for 30 min. WGA preparations enriched in IGF-1R from CHO-IGFR cells were then incubated with or without NDGA in the presence of 10 uM ATP plus or minus 10 nM IGF-1 in Kinase Buffer (50 mM, pH 7.4. 150 mM NaCl. 0.1% Triton X-100, 0.1% gelatin. 5 mM MnCl2, 8 mM MgCl2, and 1 mM PMSF). This reaction mixture was then added to the substrate-coated wells to interact with PGT for 30 min at RT. Plates were washed five times, then incubated with HRP-conjugated anti-phosphotyrosine antibody (0.3 µg/ml), diluted in Solution B (50 mM HEPES, pH 7.6, 150 mM NaCl, 0.05% Tween-20, 1 mM PMSF, 2 mM vanadate and 1 mg/ml bacitracin), for two hours at 22° C. Plates were washed and incubated with p-Tyr HRP conjugated antibody. After washing, wells were incubated with 3,3',5,5'-tetramethly benzidine (TMB) peroxidase substrate. The reaction was terminated with 1.0 M $H_3PO_4$. Values for receptor autophosphorylation were determined by measuring absorbance at 451 nm.

Determination of the Effects of NDGA on Autophosphorylation of Isolate HER2/neu.

Autophosphorylation of HER2/neu in WGA preparations enriched in this RTK were determined in the absence of ligand. Samples (1-5 µl) were incubated in the presence of varying amounts of NDGA in kinase buffer for 15 minutes at 4° C. ATP (10 µM final concentration) was added to the reaction mixture for 45 minutes at 22° C. The autophosphorylation reaction was stopped by the addition of SDS-reducing buffer, and the samples were run on SDS-PAGE. Following transfer to nitrocellulose membrane, receptor autophosphorylation was determined by a western blot that employed a phosphospecific antibody against the pNeu (Tyr1248) diluted 1:1000 in Superblock. Following an overnight incubation, membranes were washed with 3 times with tris buffered saline with 0.5% Tween 20 (TBST), then incubated with HRP conjugated sheep anti-rabbit IgG diluted 1:10,000 in Superblock for 90 minutes at room temperature. After washing, blots were incubated with SuperSignal, and exposed to film. Values were determined by scanning densitometry.

Determination of Ligand-Stimulated IGF-IR Signaling in Breast Cancer Cells.

Assays were conducted with either MCF-7, MCNeuA, or SK-Br3 breast cancer cells. The MCNeuA cell line is a mammary carcinoma cell line we have recently established from a spontaneously arising tumor in a neu transgenic female mouse (Campbell MJ, Wollish WS, Lobo M, Esserman LJ: Epithelial and fibroblast cell lines derived from a spontaneous mammary carcinoma in a MMTV/neu transgenic mouse. In Vitro Cell Dev Biol Anim 38:326-333, 2002) and is thus driven by HER2/Neu overexpression. SK-Br3 human breast cancer cells express both the IGF-1R and the HER2/Neu receptor. For the initial screening, MCF-7 cells were grown in 96 well plates. For dose effects of NDGA on cellular IGF-1R signaling, MCF-7, MCNeuA, or SKBR3 cells were grown in 6-well plates. For all studies, when cells reached 80% confluence they were serum-starved for 18 hr. NDGA was dissolved in DMSO and diluted with culture medium before being added to cells for 1 hour at 37° C. The final concentration of DMSO during the incubation was 0.3%. Cells were then stimulated with 3 nM IGF-I for 10 minutes at 37° C. Reactions were terminated by rapidly aspirating medium and washing cells three times with ice cold PBS. Cells were harvested and solubilized in 50 mM HEPES, 150 mM NaCl, 1% Triton X-100, 1 mM PMSF, and 2 mM vanadate for 1 hour at 4° C. Protein was determined by BCA assay (Pierce, Rockford, Ill.)

IGF-1R autophosphorylation was determined by ELISA as described previously for the IR (Youngren JF, Goldfine ID, Pratley RE: Decreased muscle insulin receptor kinase correlates with insulin resistance in normoglycemic Pima Indians. Am J Physiol 273:E276-E283, 1997). Briefly, 20 µg lysate protein was added to duplicate wells in a 96-well plate coated with monoclonal antibody to the IGF-1R (αIR3, 2 µg/ml), and incubated 18 hours at 4° C. ELISA color development was as described for the substrate phosphorylation assay.

Inhibition of IGF-1-stimulated activation of serine kinase Akt was determined in the lysates prepared for the IGF-1R phosphotyrosine ELISA described above. 12 µg of sample was subjected to SDS-PAGE, transfer-ed to a nitrocellulose membrane, and phosphorylated HER2/neu quantified by blotting overnight at 4 C with a phospho-specific antibody to Akt (ser473) diluted 1:1000 in Superblock. Next, blots were washed with 3 times with TBST, then incubated with HRP conjugated sheep anti-rabbit IgG diluted 1:10,000 in Superblock for 90 minutes at room temperature. Phosphorylation of the apoptotic protein BAD was determined in the same manner by blotting with a phospho-specific antibody to BAD (ser136) (1:1,000).

Determination of NDGA Effects on Cellular HER2/Neu Autophosphorylation.

HER2/neu receptor autophosphorylation was determined in serum-starved MCNeuA or SKBR3 cells, which were collected in the basal state, due to the ligand-independent nature of HER2/neu activation. Following a one-hour incubation in serum-free media, soluble extracts of cells were prepared as above. HER2/neu autophosphorylation was determined by a western blot that employed a phosphospecific antibody, pNeu (Tyr1248) as described above.

Effects of NDGA on Proliferation of Breast Cancer Cells.

The inhibitory effects of NDGA on breast cancer cell growth were determined using a CyQUANT cell proliferation assay kit (Molecular Probes, Eugene, Oreg.). MCF-7 or MCNeuA cells were plated in 96 well plates ($5 \times 10^3$ cells/well) in DMEM supplemented with 10% FCS. One plate was prepared for each harvest day. Cells were allowed to adhere overnight and were then treated with various concentrations of NDGA or DMSO as a vehicle control. Microplate cultures were harvested on days 0, 1, 2, and 3 by inverting the microplate onto paper towels with gentle blotting to remove growth medium without disrupting adherent cells. Each plate was kept at −80° C. until the end of the experiment (day 3) when all of the plates were thawed and assayed together. After thawing, 200 µl of CyQUANT GR solution was added to each well and the plates were incubated in the dark for two to five minutes. Fluorescence was measured with a SpectraMax Gemini XS fluorescence microplate reader (Molecular Devices, Sunnyvale, Calif.) with 480-nm excitation and 520-nm emission. Proliferation index was calculated as the percent of nucleotide content versus control cells at day 0.

Effects of NDGA on IGF-1 Stimulated Proliferation of Breast Cancer Cells.

MCF-7 cells were harvested at an early passage number by washing three times with PBS and trypsinizing with 1 mL 0.05% trypsin. Cells were resuspended in 5 ml defined medium (1:1 Ham's F12: DMEM 4.5 g/L glucose: 1 mg/mL BSA: 10 ug/mL Transferrin; 15 mM HEPES pH 7.2; 2 mM L-glutamine; 100 units/mL Penicillin G; 100 mcg/mL Streptomycin SO4; 2.5 ug/mL Fungizone) containing 200 ug soybean trypsin inhibitor. Cells were plated in 96 well collagen coated plates (Sigma, St. Louis, Mo.) at a density of 5000 cells/well in 100 ul medium. Twenty hours later defined medium with or without IGF-I at varying concentrations was added. Four hours later NDGA diluted in defined medium was added. Plates were harvested on day 3, as described above, for determination of cell number by CyQUANT assay.

In Vivo Studies

All animal studies complied with protocols approved by of the Institutional Animal Care and Use Committee of the University of California, San Francisco. Our syngeneic model studies utilized the FVB/N-TgN(MMTVneu)202 mouse strain developed by Muller and colleagues (Guy CT, Webster MA, Schaller M, Parsons TJ, Cardiff RD, Muller WJ: Expression of the neu protooncogene in the mammary epithelium of transgenic mice induces metastatic disease. Proc Natl Acad Sci USA 89:10578-10582, 1992). This strain, denoted hereafter as neuTg, expresses the wild-type rat neu proto-oncogene (a homologue of human HER2) under the control of the mouse mammary tumor virus (MMTV) long terminal repeat (LTR) on an FVB mouse background. The MCNeuA mammary carcinoma cell line employed in these studies was derived from a spontaneously arising tumor in a neuTg female mouse (Campbell MJ, Wollish WS, Lobo M, Esserman LJ: Epithelial and fibroblast cell lines derived from a spontaneous mammary carcinoma in a MMTV/neu transgenic mouse. In Vitro Cell Dev Biol Anim 38:326-333, 2002). These cells are tumorigenic when transplanted back into neuTg mice. Female mice were injected subcutaneously with $10^5$ MCNeuA tumor cells on day 0. Treatment with NDGA began on day 9. One group of mice received 37.5 mg/kg NDGA prepared in 20% warm (37° C.) ethanol, administered intraperitoneally (i.p.) three times per week. The general preparation of NDGA into vehicle involved heating 100% ethanol and deionized distilled water to 37° C. The desired amount of NDGA was then dissolved in 100% ethanol and diluted with water drip by drip for a final solution of 20% ethanol/80% water. This solution was kept warm at 37° C. until given to mice by i.p. injection. A second group of mice received an oral dose of 100 mg/kg by gavage. NDGA was prepared for oral delivery by dissolving it in carboxymethylcellulose. Control mice received i.p. injections of ethanol/water vehicle only. Tumor growth was measured at the time of drug delivery on alternate treatment days with calipers and volume calculated using the equation:

$$(length \times width^2) * (\pi/6).$$

RTK Activation in Tumors

At the end of the study, approximately 16 hrs following a final i.p. dose of NDGA, tumors were excised from the mice in order to assess the autophosphorylation state of IGF-1 and HER2/neu receptors. Tumors were homogenized in 50 mM HEPES, pH 7.6, 150 mM NaCl, 1 mM PMSF, 2 μM leupeptin, 2 μM Pepstatin A, and 2 mM $Na_3VO_4$, and solubilized by the addition of 1% Triton x-100. Soluble lysates were prepared as described for cell culture studies. Tyrosine phosphorylation of IGF-1R was determined by ELISA as described for MCF-7 cells. Phosphorylation of HER2/neu was determined by western blot employing the phospho-specific antibody as in the cell culture studies. The degree of phosphorylation for each receptor was normalized to total receptor protein content in the tumor samples as determined by western blotting with antibodies against the human IGF-1R and the rodent HER2/neu.

Statistics

Statistics were calculated using MedCalc statistical software (MedCalc Software, Mariakerke, Belgium). Growth of breast cancer cells in culture and in vivo was analyzed by two-way analysis of variance for treatment, time, and interaction effects with post-hoc analysis by Student's t-test. Dose effects of NDGA on receptor phosphorylation were analyzed by one-way analysis of variance with post-hoc analysis by Student's t-test. Significance was set at $P<0.05$.

Results

Effects of NDGA on Isolated RTKs.

NDGA (FIG. 1) has previously been shown to directly inhibit ligand-stimulated PDGFR autophosphorylation (Domin J, Higgins T. Rozengurt E: Preferential inhibition of platelet-derived growth factor-stimulated DNA synthesis and protein tyrosine phosphorylation by nordihydroguaiaretic acid. J Biol Chem 269:8260-8267. 1994) and a homologous compound is an inhibitor of the IGF-1R (Blum G. Gazit A, Levitzki A: Substrate competitive inhibitors of IGF-1 receptor kinase. Biochemistry 39:15705-15712, 2000; Blum G. Gazit A, Levitzki A: Development of new insulin-like growth factor-1 receptor kinase inhibitors using catechol mimics. J Biol Chem 278:40442-40454, 2003).

The present invention shows that NDGA has a direct effect on both IGF-1R and HER2/neu receptors. More specifically, the present invention shows the ability of NDGA to inhibit autophosphorylation and/or substrate tyrosine kinase activity of both these receptors in vitro. The ability of NDGA to directly inhibit the kinase domain of the receptor was shown using a synthetic peptide consisting of the 379 terminal amino acids of the IGF-1R beta subunit. This peptide, which displays intrinsic autophosphorylation and substrate tyrosine kinase activity, was incubated with increasing concentrations of NDGA prior to the addition of 20 μM ATP. Under these conditions, NDGA inhibited activation of the IGF-1R kinase domain at a concentration at 1 μM and the results are shown in the Western blot image of FIG. 8.

The effects of NDGA against the intact IGF-1 and HER2/neu receptors were shown using wheat germ affinity chromatography to obtain fractions enriched in either the human IGF-1R or the rodent HER2/neu receptor extracted from cells overexpressing these proteins. In IGF-1R preparations, we determined the ability of NDGA to inhibit IGF-1 stimulated phosphorylation of the synthetic tyrosine kinase substrate, poly Glu4:Tyr1. Incubation of IGF-1R preparations with NDGA for 20 minutes prior to the addition of 10 nM IGF-1 produced dramatic reductions in tyrosine phosphorylation of the substrate (FIG. 3). This effect was observed at concentrations of NDGA as low as 0.3 μM.

Because HER2/neu is intrinsically active in cells in the absence of ligand binding, basal autophosphorylation is observed in isolated receptor preparations (FIG. 4). Incubation of HER2/neu preparations with 10 μM ATP produced a further increase in ligand-independent HER2/neu autophosphorylation. However, preincubation with NDGA for 20 minutes prior to the addition of ATP abolished this increase in HER2/neu autophosphorylation (FIG. 4).

Effects of NDGA on IGF-1R and HER2/neu Signaling in Cells.

Treatment of MCF-7 cells with increasing concentrations of NDGA for one hour prior to the addition of 3 nM IGF-1produced a dose-dependent decrease in IGF-1R autophosphorylation with an $IC_{50}$ of $31\pm12$ μM (FIG. 5A). Similar effects of NDGA on IGF-1R autophosphorylation were observed in SK-Br3 breast cancer cells (data not shown). In order to determine the impact of NDGA on downstream signaling of the IGF-1R, we studied the Akt/BAD pathway that regulates cellular apoptosis. Incubation of MCF-7 cells with 1 nM IGF-1 dramatically increased phosphorylation of Akt, and, to a lesser extent, BAD. These effects were reduced in a dose-dependent manner by concentrations of NDGA similar to those that inhibited IGF-1R autophosphorylation (FIG. 5B). These data demonstrate that NDGA treatment results in transition into a pro-apoptotic state for MCF-7 cells.

Because MCF-7 cells do not express HER2/neu, we employed MCNeuA cells, a breast cancer cell line derived from transgenic mice overexpressing the rodent form of this receptor. Exposure of these cells to increasing concentrations of NDGA produced a dose-dependent inhibition of HER2/neu autophosphorylation. Ligand-independent tyrosine phosphorylation of HER2/neu was inhibited by NDGA with an $IC_{50}$ of 15±4 µM (FIG. 6). Similar results were observed in SK-Br3 cells, which express relatively large amounts of the human HER2/neu receptor (data not shown).

Effects of NDGA on Growth of Breast Cancer Cells in Culture:

Given the ability of NDGA to inhibit the function of the IGF-1R and the HER2/neu receptor, we tested its effect on the proliferation of MCF-7 and MCNeuA breast cancer cells under normal culture conditions. When MCF-7 cells were grown in 10% fetal calf serum and then incubated with varying concentrations of NDGA for up to 3 days, the rate of proliferation was significantly reduced by NDGA concentrations as low as 15 µM (FIG. 7A). At 60 µM, cell number was dramatically reduced within 24 hours. As numerous growth factors are present in serum, we examined the ability of NDGA to specifically inhibit growth of these cells mediated by IGF-1 alone. In MCF-7 cells grown in media supplemented only with 10 nM IGF-1, NDGA inhibited proliferation with an $IC_{50}$ of approximately 10 µM (FIG. 7B). In the presence of 10% fetal calf serum. NDGA also inhibited growth of MCNeuA cells, for which growth is largely due to the ligand-independent activity of the overexpressed HER2/neu receptor, and SK-Br3 cells, which express relatively high levels of both IGF-1 and HER2/neu receptors with potencies similar to that observed for MCF-7 cells (data not shown).

Figure 8:
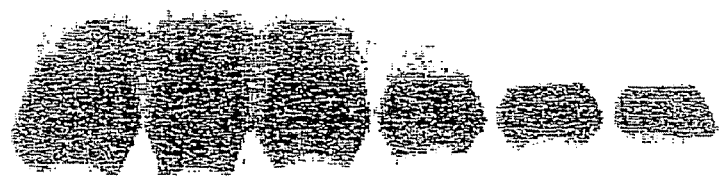
FIG. 8 is an image of a Western Blot obtained by incubating different concentrations of NDGA with a peptide corresponding to the kinase domain of IGF-1R.

Effects of NDGA on IGF-1R and HER2/neu Receptor Activation of Breast Tutors in Mice:

In order to assess the ability of NDGA to inhibit activation of the IGF-1R and HER2/neu receptor in vivo, we employed a syngeneic mouse model of breast cancer featuring a cell line that expresses both RTKs. In these studies, MCNeuA breast cancer cells were injected subcutaneously into female neuTg mice, the strain from which this cell line was originally obtained. NDGA was administered three times a week either as an i.p. dose of 37.5 mg/kc or as an oral dose of 100 mg/kg, prepared in carboxymethylcellulose. Administration of NDGA began nine days after implantation of tumor cells. Twenty nine days post-implantation, and 16 hours following the final administration of NDGA tumors were excised from intraperitonealy-treated and control mice at the end of the study and analyzed. We observed that autophosphorylation of both receptors was reduced in tumors from NDGA-treated mice compared to vehicle-treated controls (FIG. 8). NDGA treatment had no effect on the total cellular content of either the IGF-1 or HER2/neu receptor.

FIG. 8 shows that NDGA Directly Inhibits Autophosphorylation of IGF-1R Kinase Domain. A peptide corresponding to the kinase domain of IGF-1R was incubated with varying concentrations of NDGA prior to the addition of ATP. Inhibition of peptide tyrosine phosphorylation by NDGA was determined by western blots that employed an anti-phosphotyrosine antibody. A representative blot is shown.

Inhibition of signaling by both RTKs through treatment with NDGA in vivo was associated with a reduced tumor growth rate. There were no differences in tumor growth rates between animals receiving oral or i.p. administration of NDGA. Data combined from both treatment groups demonstrated that NDGA significantly reduced tumor growth from 21 days post-implantation through the remainder of the study (FIG. 9).

Figure 9:
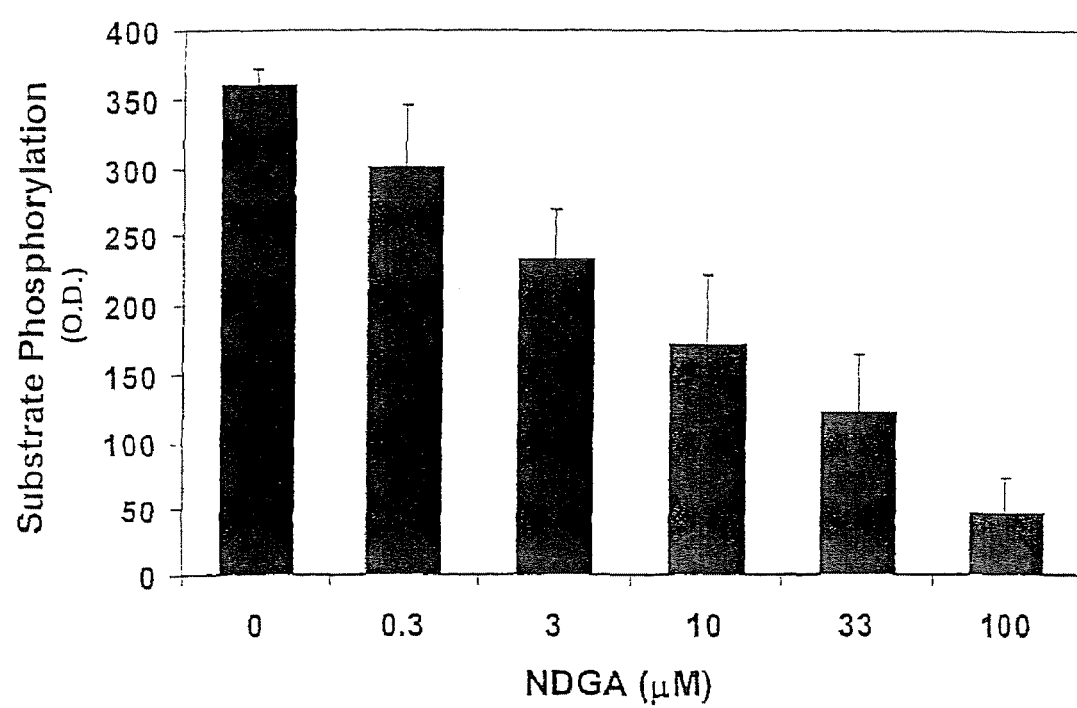
FIG. 9 is a bar graph showing the results of IGF-1R incubated with various concentrations of NDGA prior to addition of IGF-1 wherein results were determined by ELISA employing an anti-phosphotyrosine antibody to readout.

FIG. 9 shows that NDGA Directly Inhibits Tyrosine Kinase Activity of Isolated IGF-1R. IGF-1R were partially purified by affinity chromatography from cells overexpressing human IGF-1R. The IGF-1R was incubated with varying concentrations of NDGA prior to the addition of IGF-1. ATP-induced tyrosine phosphorylation of the immobilized substrate, poly Glu4:Tyr1 was determined by ELISA employing an anti-phosphotyrosine antibody to readout. IGF-1 stimulation of substrate phosphorylation was calculated as the O.D. value in the absence of added IGF-1 subtracted from the O.D. value in each experimental condition. Values represent mean±SEM of 3 experiments.

Figure 10:
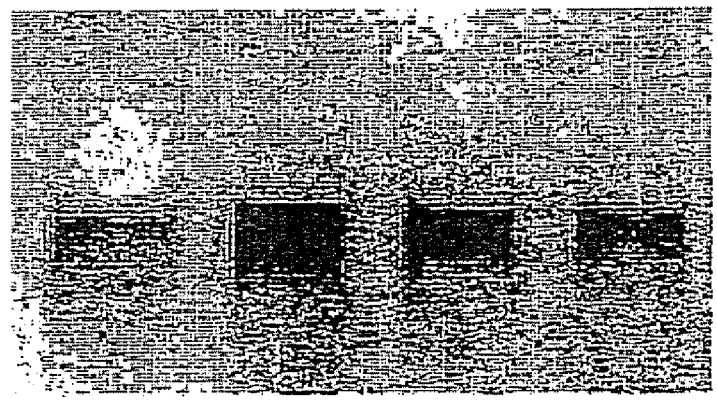
FIG. 10 is an image of a Western Blot wherein HER2/neu recepetors were incubated with ATP alone or with NDGA.

FIG. 10 shows that NDGA Directly Inhibits Autophosphorylation of Isolated HER2/neu. HER2/neu receptors were partially purified by affinity chromatography from cells overexpressing mouse HER2/neu. Incubation of HER2/neu receptors with NDGA prior to the addition of ATP reduced autophosphorylation as determined by western blot employing a phosphospecific antibody, pNeu(Tyr1248). A representative blot of 3 experiments is shown.

Figure 11A:
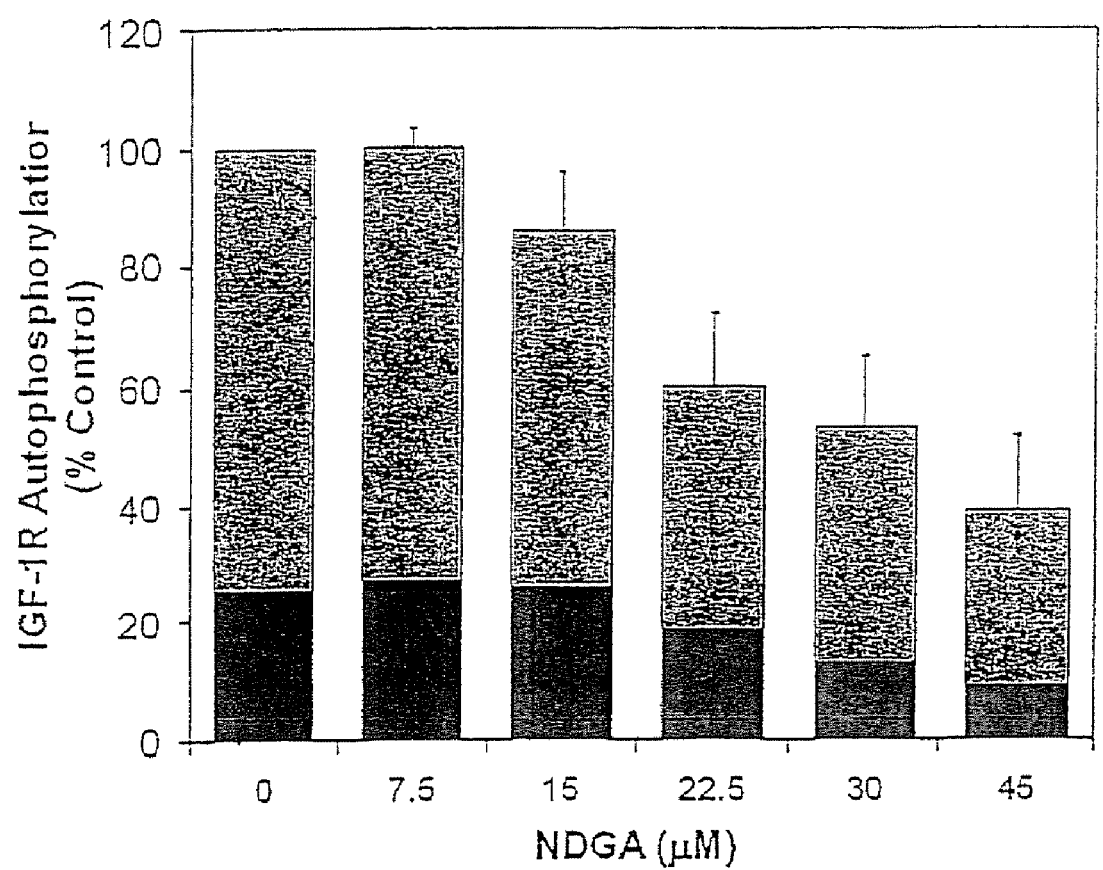
FIG. 11A is a bar graph and FIG. 11B is two images of Western Blots showing results where MCF-7 breast cancer cells were incubated with various concentrations of NDGA.
Figure 11B:
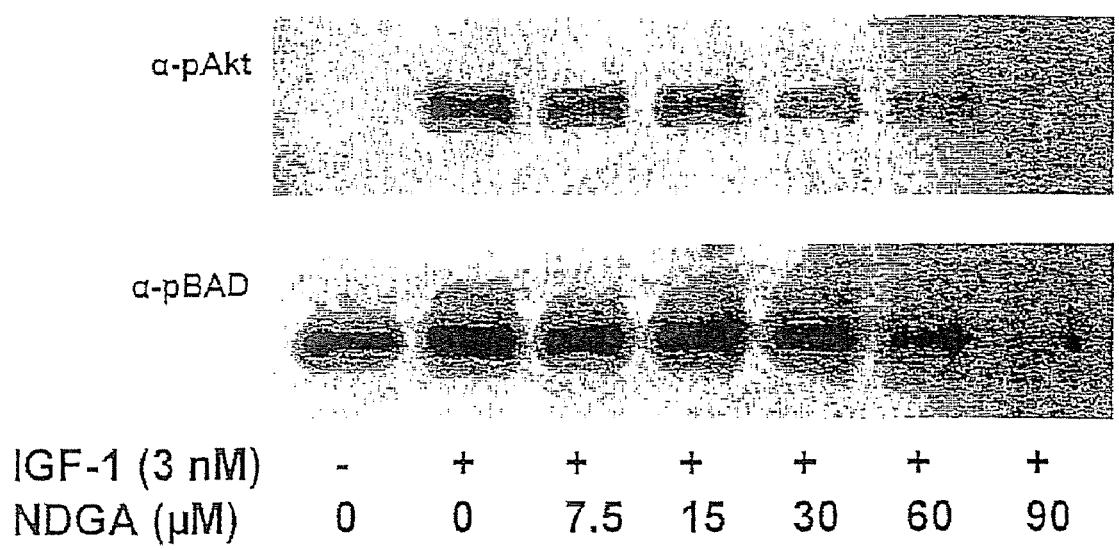

FIG. 11 shows that NDGA Inhibits the IGF-1R Signaling Pathway in MCF-7 Cells. MCF-7 breast cancer cells were incubated with varying concentrations of NDGA for 1 hr. Soluble extracts were then collected in the basal state or following a 10 minute incubation with 3 nM IGF-1. (A) Tyrosine phosphorylation of the IGF-1R was then determined by specific ELISA (■ basal state; 3 nM IGF-1). Values represent mean±SEM of 3 experiments, normalized to cells treated with vehicle alone. *Values significantly reduced vs. vehicle treated controls. (B) Serine phosphorylation of PKB and BAD determined by western blot. Representative blots of 3 experiments are shown.

Figure 12:
FIG. 12 is an image of a Western Blot showing results wherein MCNeuA breast cancer cells were incubated with varying concentrations of NDGA.

FIG. 12 shows that NDGA Inhibits HER2/neu Autophosphorylation in MCNeuA Cells. MCNeuA breast cancer cells were incubated with varying concentrations of NDGA for 1 hr. Tyrosine phosphorylation of HER2/neu receptors in soluble extracts was determined by western blot employing a phosphospecific antibody. A representative blot of four experiments is shown.

Figure 13A:
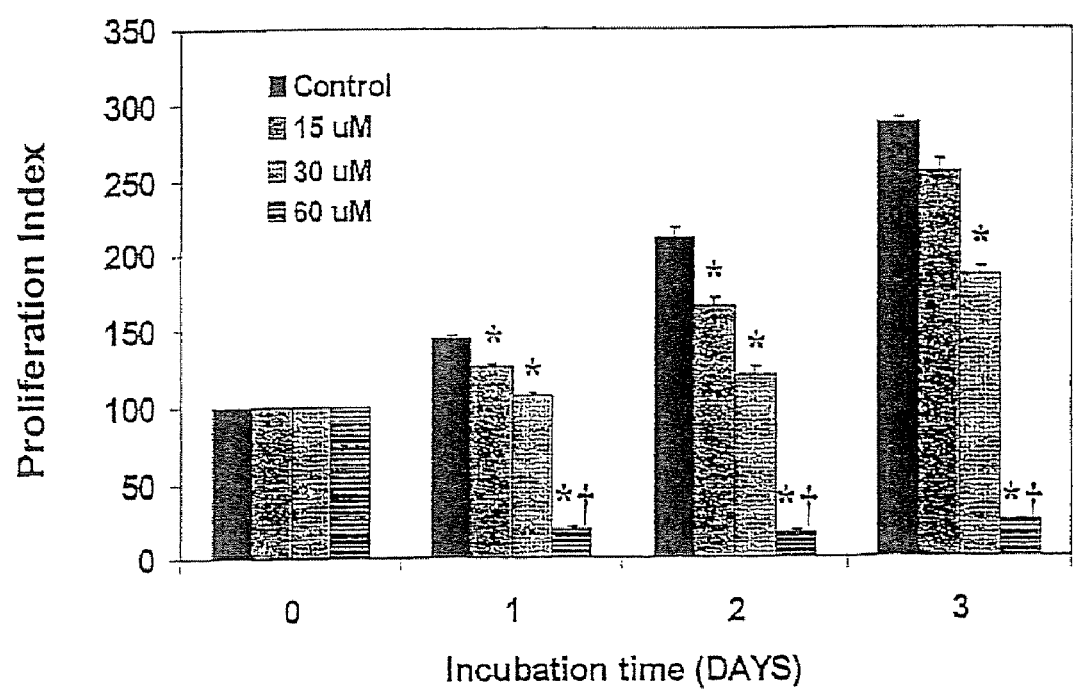
FIG. 13A is a bar graph showing results of incubating MCF-7 cells with varying concentrations of NDGA and FIG.
Figure 13B:
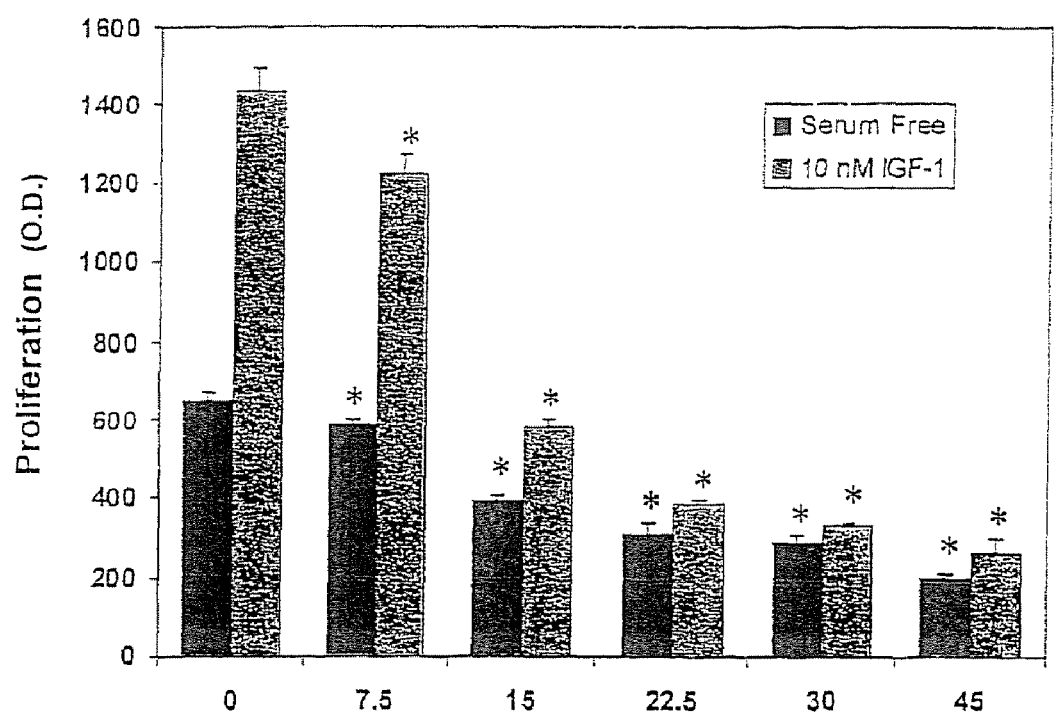

FIG. 13 shows that NDGA Inhibits Serum and IGF-1 Stimulated Proliferation of MCF-7 Breast Cancer Cell Lines. (A) MCF-7 cells were grown in media supplemented with 10% fetal calf serum. Beginning on day 0, cells were incubated with varying concentrations of NDGA. Cell number was estimated by determination of nucleotide content (CyQUANT assay) on days 0, 1, 2 and 3. Proliferation index was calculated as the percent difference in cell number vs. day 0. (B) MCF-7 cells were initially plated in basal media. Growth continued in basal media or media supplemented with 10 nM IGF-1. 24 hours after plating (day 0), cells were incubated with varying concentrations of NDGA or DMSO alone. Plates were harvested on day 3 for CyQuant assay. Values shown are O.D. values reflecting total nucleic acid content per well. All values represent mean±SEM of 3 experiments. *Proliferation significantly reduced vs. vehicle treated controls. †Cell number significantly reduced from day 0.

FIG. 14 shows that Chronic NDGA Administration Inhibits RTK Activation in Tumors In Vivo. Following 21 days of treatment, and 16 hrs after the final intraperitoneal administration of NDGA, MCNeuA tumors were excised and soluble protein extracts prepared. Tyrosine phosphorylation of IGF-1R (black bars) was determined by ELISA. Phosphorylation of HER2/neu (gray bars) was determined by western blot. Tumor content of both RTKs was not different across treatment groups as determined by western blot. Values represent mean phosphorylation level normalized to control values±SEM for 4-5 animals per group. *Receptor tyrosine phosphorylation significantly reduced vs. vehicle treated controls.

FIG. 15 shows that Growth Inhibition of MCNeuA Cells in vivo By NDGA Administered Orally and by Intraperitoneal Injection. MCNeuA cells were injected into NeuTG mice on day 0. Treatment with NDGA began on Day 9, with NDGA administered 3× week, either orally in carboxymethylcellulose (100 mg/kg) (▲) or injected intraperitoneally (37.5 mg/kg) (■). Values represent mean tumor volume±SEM for 4-5 animals per group. *Tumor volume significantly reduced for combined treatment groups vs. vehicle treated controls.

Example 2

Neuroblastoma

Materials and Methods

Cell culture aid reagents. Human SH-SY5Y, SHEP, and Kelly neuroblastoma cells were cultured in Dulbecco's modified Eagle medium (DMEM) with 10% calf serum and maintained in a humidified incubator with 10% $CO_2$ at 37° C. NDGA from Insmed Corporation (Richmond, Va.) was dissolved immediately before each experiment in DMSO to make a 1000× solution, which was then added to the cell culture medium. IGF-I was purchased from GroPep (Adelaide, SA, Australia). Anti-IGF-IR antibody (αIR-3) was purchased from Calbiochem (San Diego, Calif.). Anti-phosphotyrosine antibody was purchased from Santa Cruz Biotechnology (Santa Cruz, Calif.). Anti-Akt, anti-phospho-Akt, anti-Erk1/2, anti-phospho-Erk1/2, and anti-cleaved caspase-3 antibodies were purchased from Cell Signaling Technologies (Beverly, Mass.). Horseradish peroxidase conjugated goat anti-rabbit IgG was purchased from Zymed Laboratories (South San Francisco, Calif.). CyQuant was purchased from Molecular Probes (Eugene, Oreg.). Propidium iodide was purchased from Sigma (St. Louis, Mo.).

IGF-1R phlosphorylation ELISA. SH-SY5Y and SHEP cells were grown to 80% confluence in DMEM/10% calf serum, then serum-starved for 4 h. Cultures were then treated with DMSO or 60 uM NDGA and incubated for 1 h. Some cultures were then treated with 1 nM IGF-I for 10 min. The medium was removed, cultures rinsed 3× in cold PBS, and lysis buffer (120 mM HEPES, 300 mM NaCl, 2 mM sodium orthovanadate, and 1 mM phenylmethylsufonylfluoride (PMSF)) was added. Cultures were rocked in lysis buffer at 4° C. for 1 h. 96-well plates were coated with αIR-3 antibody in 50 mM $NaHCO_3$, pH 9.0, for 2 h at RT. Plates were rinsed 3× in tris-buffered saline +0.1% Tween (TBST), then blocked with SuperBlock (Pierce, Rockford, Ill.) for 30 min at RT. Each well of the ELISA plate received 30 μg of lysate protein from the cell cultures, followed by 24 h incubation at 4° C. Plates were rinsed 5× with TBST, and HRP-conjugated anti-phosphotyrosine antibody was added (1:2000, diluted in 120 mM HEPES, 300 mM NaCl, 2 mM sodium orthovanadate. and 1 mM PMSF. 1% bovine serum albumin, 1 mg/ml bacitracin, and 0.5% Tween-20) for 2 h at RT. Plates were again rinsed 5× in TBST, and TMB (Pierce) was added until blue color was sufficiently developed. Absorbance at 451 nm was quantified. Each lysate was run in triplicate, and the experiment was repeated 3 times.

CyQUANT assay for cell growth. Cells were plated on four 96-well tissue culture plates, in DMEM/10% calf serum at a density of 8000 cells/well and incubated for 24 h. In one set of experiments, the medium was switched to serum free DMEM supplemented with 1% bovine serum albumin (to provide osmotic support). IGF-I (10 nM) was added to some samples on a daily basis for up to 3 days. In a second set of experiments, the cells continued to be cultured in DMEM/10% calf serum for the duration of the experiment, with no additional IGF-I. For all experiments, DMSO or different concentrations of NDGA were added to the cultures at 0 h (the day after plating). The media from one plate was immediately removed, and the plate was frozen at −80° C. This plate served as the baseline for the experiment. Single plates were frozen at 24, 48, and 72 h following addition of drugs. DNA content of each well was quantified by staining with CyQUANT according to the manufacturer's instructions and measuring CyQUANT absorbance with a fluorimeter. Each condition was run in triplicate, and the experiment was repeated three times.

Detection of phospho-Akt and phospho-Erk. Cells were grown to 80% confluence, serum starved for 4 h, and treated with DMSO or different concentrations of NDGA for 1 h. Then, some cultures were treated with 10 nM IGF-I for 15 min. Cultures were immediately placed on ice, the medium was removed, and the cells were lysed in modified RIPA buffer (20 mM Tris, 150 mM NaCl, 1 mM EDTA, 1 mM EGTA, 1% Triton X-100, 0.1% sodium dodecyl sulfate, and 1% deoxycholate). Fifty μg of protein from each sample were separated via SDS-PAGE and transferred to nitrocellulose. Phospho- and total-Akt and -Erk were detected by immunoblotting.

Propidium iodide staining of apoptotic cells. SH-SY5Y cells were cultured in DMEM with 10% calf serum. Cultures were treated with DMSO or NDGA for 24 h. The supernatant was collected to save detached cells. Attached cells were removed from the plate via trypsinization, and pelleted by centrifugation in combination with the cells in the supernatant. The cell pellet was fixed by drop-wise addition of cold 70% ethanol while vortexing, gently, and stored at 4° C. The pellet was washed twice and resuspended in PBS and stained with 1 μg/ml propidium iodide. Propidium iodide fluorescence was measured in 30,000 cells per sample using a Becton-Dickinson (Franklin Lakes, N.J.) Facscalibur flow cytometer. The percentage of cells in each stage of the cell cycle, as well as the percentage of cells that were apoptotic (sub-G0) was determined by analyzing the data with ModFit software. The experiment was repeated three times.

Detection of Caspase-3 cleavage. Neuroblastoma cells were grown to 80% confluence and treated with DMSO or NDGA for 6 h. Alternatively, cells were serum starved for 4 h and cultured with or without 60 μM NDGA and with or without 10 nM IGF-I for 3 h. Lysates were collected as described above, and the 14/17 kD cleavage fragments of caspase-3 were detected via SDS-PAGE followed by immunoblotting with anti-cleaved caspase-3 antibody.

Measurement of cell motility. Neuroblastoma cells were plated on gold particle-coated coverslips (prepared as described in (30)) in serum-free media at a density of 25,000 cells per coverslip. The cells were incubated for 2 h to allow adhesion to the coverslip. Then, wells were treated with DMSO or 30 μM NDGA for 1 h. 1 nM IGF-I was then added to some wells. Incubation continued for 6 h, followed by fixation with 3.5% glutaraldehyde. Coverslips were mounted on glass slides, then viewed on a Lietz Orthoplan inverted microscope attached to a Sony videoprocessor. Digital images of the tracks etched into the gold by the cells from 3 separately treated coverslips per condition were collected at 200× magnification using Adobe Photoshop software. For each condition, the areas of 120 tracks made by individual cells were measured with NIH Image 1.61 software.

Treatment of xenografted nude mice with NDGA. Nude mice xenografted with human Kelly neuroblastoma cells were treated with NDGA to determine if NDGA can affect tumor growth in vivo. Briefly, $7 \times 10^6$ Kelly human neuroblastoma cells were resuspended in a 1:1 mixture of PBS and Matrigel (BD Clontech Inc.) and 100 μl of the mixture was injected subcutaneously into the flanks of 6-12 week-old BALB/c nude mice. After 1 cm tumors were established (~10-14 days post implantation), animals were injected subcutaneously with either vehicle (DMSO) or NDGA, (50 mg/kg, suspended in DMSO) daily for 10 days. Tumors were then harvested, weighed and measured. The formula width$^2$× length/2 was used to calculate tumor-volumes.

Results

IGF-1 stimulated IGF-1R phosphorylation in neuroblastoma cells is inhibited by NDGA. NDGA was previously shown to inhibit the autophosphorylation of the IGF-IR in partially purified preparations of the receptor, and in breast cancer cell lines. To test the effects of NDGA on IGF-IR activation in neuroblastoma cells, serum-starved SHEP and SH-SY5Y neuroblastoma cells were treated with either DMSO (vehicle control) or 60 µM NDGA for 1 h (FIGS. 16A and 16B). The cultures were then treated for 10 min with or without 1 nM IGF-I. Protein lysates were collected and the degree of IGF-IR phosphorylation in the lysate samples was quantified using ELISA. IGF-I induced an increase in IGF-IR tyrosine phosphorylation in both cell lines. This IGF-I stimulated receptor phosphorylation was inhibited by NDGA. SH-SY5Y (A) cells showed a higher response to IGF-I than SHEP cells (B), consistent with the increased basal levels of IGF-IR found in SH-SY5Y cells (Kim B, van Golen CM and Feldman EL. Insulin-like growth factor-I signaling in human neuroblastoma cells. Oncogene 2004;23:130-141).

FIGS. 16A and 16B show that NDGA inhibits activation of the IGF-IR by IGF-I. SH-SY5Y (A.) and SHEP (B.) neuroblastoma cells were serum starved and treated with DMSO or 60 µM NDGA for 1 h. Then, 1 nM IGF-I was added to half the cultures for 10 min. IGF-IR phosphorylation was detected by an ELISA (Materials and Methods). Results are means +/− SEM for measurements collected in all experiments expressed as a percentage of IGF-IR phosphorylation in unstimulated DMSO-treated cells. The experiment was repeated three times, with each condition run in triplicate within each experiment. *$p<0.01$ vs. DMSO+IGF-I.

NDGA inhibits neuroblastoma proliferation. The amount of cellular DNA present in neuroblastoma cultures was measured to quantify the cell proliferation or cell death that occurred during a three day treatment with NDGA. SH-SY5Y and Kelly neuroblastoma cells were cultured on four 96-well plates in serum-free media supplemented with 10 nM IGF-I for up to 72 h. At 0 h, the cultures were treated with 15-120 ρM NDGA, or DMSO as control. The cell content of each plate was measured by staining for total DNA, using CyQUANT dye. In both SH-SY5Y and Kelly cells, treatment with NDGA inhibited proliferation, and caused cell death at higher doses (FIGS. 17A and 17B).

FIGS. 17A and 17B show that NDGA inhibits neuroblastoma growth in serum-free medium supplemented with 10 nM IGF-I. SH-SY5Y (A.) and Kelly (B.) neuroblastoma cells were cultured in serum-free medium with 10 nM IGF-I and treated with DMSO or NDGA (15-120 µM). DNA content was measured at 0, 24, 48, and 72 h using CyQUANT staining (Materials and Methods). Means+/− SEM from three separate experiments are expressed as a percentage of absorbance at 0 h. $p<0.05$ vs. DMSO-treated control at the same time point.

To determine if NDGA would still have an inhibitory effect on neuroblastoma growth in serum, where other factors could contribute to neuroblastoma mitogenesis and survival in addition to IGFs, the experiment was repeated using SHEP and SH-SY5Y cells cultured in medium containing 10% serum (FIG. 18A and 18B). NDGA inhibited the proliferation of SH-SY5Y and SHEP cells cultured in serum up to 72 h. Higher doses of NDGA caused cell death, as the amount of DNA in these cultures is less than the amount at 0 h. These results demonstrate that NDGA inhibits the growth and survival of neuroblastoma cells supported by either serum or IGF-I.

Figure 2:
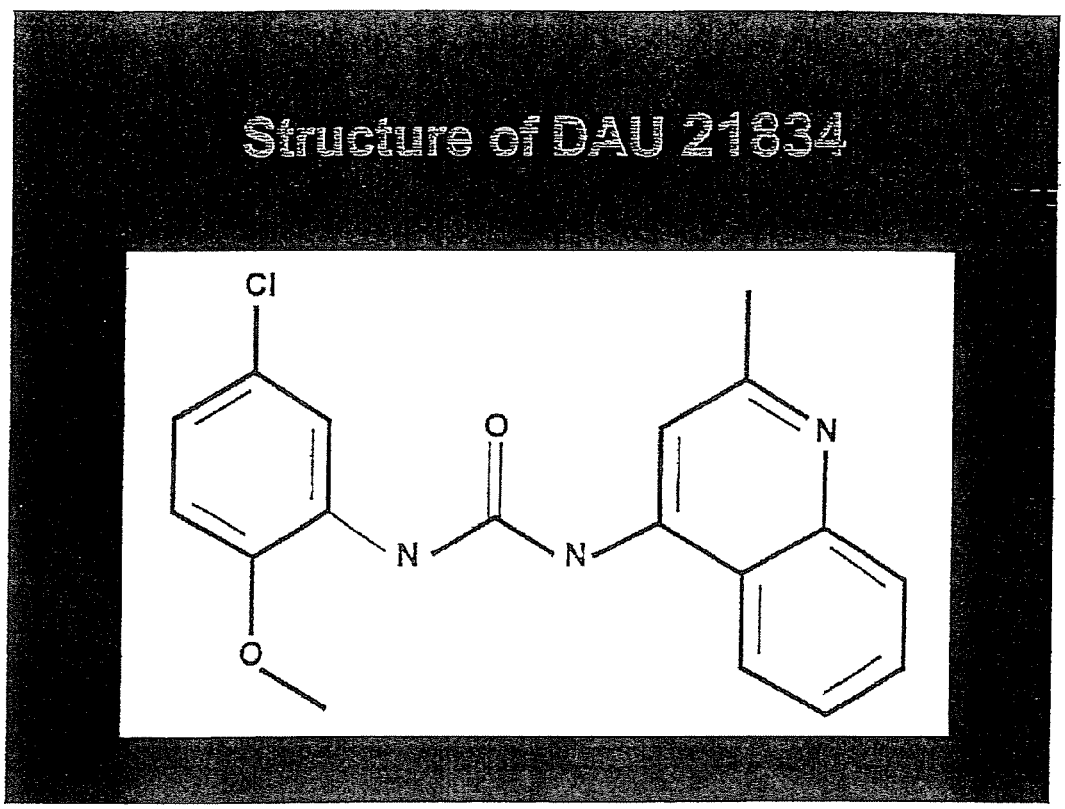
FIG. 2 shows the chemical structure of diarylurea 21834 (DAU).

FIGS. 18A and 18B show that NDGA inhibits neuroblastoma growth in serum. SH-SY5Y (A.) and SHEP (B.) neuroblastoma cells were cultured in serum and treated with DMSO or NDGA (30-120 µM). Samples were collected and processed for CyQUANT absorbance as in FIG. 2. Each bar represents the mean+/− SEM of three separate experiments, and each condition was run in triplicate. *$p<0.05$ vs. DMSO-treated control at the same time point.

NDGA prevents IGF-I activation of the MAPK pathway. Neuroblastoma mitogenesis is regulated by IGFs via the activation of the MAPK signaling pathway, leading to the phosphorylation and activation of ERK 1 and 2. The effects of NDGA treatment on IGF-stimulated ERK phosphorylation were investigated in SHEP and SH-SY5Y neuroblastoma cells. Serum starved cells were treated for 1 h with DMSO or increasing concentrations of NDGA, and then stimulated with 10 nM IGF-I for 15 min. Lysates were collected and proteins separated by SDS-PAGE as described in Materials and Methods. ERK phosphorylation was assessed by immunoblotting with anti-phospho ERK1/2 antibody. ERK phosphorylation was increased by IGF-I in SH-SY5Y cells (FIG. 19A). NDGA causes a dose-dependent inhibitory effect on IGF-stimulated phosphorylation of ERK. The total ERK content of each lane is shown for comparison. Similar results were obtained in SHEP cells.

Akt phosphorylation is inhibited by NDGA. IGFs also signal through the PI-3K pathway in neuroblastoma cells, leading to the activation of Akt. The effect of NDGA on IGF-stimulated Akt activation was assessed in serum-starved SH-SY5Y and SHEP cells, via SDS-PAGE and Western immunoblotting. Similar to the effects on ERK phosphorylation, NDGA caused a dose-dependent inhibition of IGF-stimulated Akt phosphorylation in SH-SY5Y and SHEP cells (FIG. 19B). Total Akt content of each lane is shown for control.

FIGS. 19A and 19B show that IGF-I-stimulated ERK and Akt activation are blocked by NDGA. SH-SY5Y cells were serum starved and treated with DMSO or 3, 30, or 60 µM NDGA for 1 h, then given 10 nM IGF-I for 15 min. Lysates were collected and ERK (A.) or Akt (B.) phosphorylation was detected via Western blot analysis. A. Upper panel shows ERK phosphorylation. Lower panel is total ERK to show equal loading of lanes. B. Upper panel shows phospho-Akt, while lower panel shows total Akt as a loading control. Representatives of three separate experiments are shown.

Caspase-3 is activated by NDGA. Akt activation supports neuroblastoma survival by suppressing apoptosis, in part by preventing the catalytic activation of caspase-3. Disruption of Akt signaling increases activation of caspase-3 driving neuroblastoma cells into apoptosis.

To determine if NDGA causes caspase-3 activation, SH-SY5Y neuroblastoma cells were cultured in serum and treated with NDGA for 6 h. Caspase-3 activation was assessed by SDS-PAGE and immunoblotting with anti-cleaved caspase-3 antibody, which detects the small cleavage fragments of caspase-3 that are released upon its activation. GAPDH expression was detected for loading control. NDGA causes dose-dependent caspase-3 activation (FIG. 20A). To determine if exogenous IGF-I was able to prevent this activation. SH-SY5Y cells were cultured in serum-free media containing 10 nM IGF-I and simultaneously treated with NDGA or DMSO as a control. Caspase-3 activation was still detectable when NDGA-treated cells were given IGF-I (10 nM) (FIG. 20B). Caspase-3 activation was not detected in serum-starved cells cultured in the absence of IGF-I, while NDGA treated SH-SY5Y cells cultured in the absence of IGF-I, which secrete their own IGF-I, showed strong caspase activation. This shows that NDGA is capable of both pushing the cells into an apoptotic state and suppressing IGF-mediated rescue.

NDGA causes neuroblastoma cells to undergo apoptosis. SH-SY5Y cells cultured in serum were treated with DMSO or NDGA (30-120 μM). After 24 h, the cells were harvested and subjected to flow cytometric cell cycle analysis as described in Materials and Methods. NDGA causes a dramatic, dose-dependent increase in the percentage of sub-$G_0$ cells, the fraction of cells undergoing apoptosis (FIG. 20C).

FIGS. 20A, 20B and 20C show that NDGA causes caspase activation and apoptosis in neuroblastoma cells. A. SH-SY5Y cells grown in serum containing-medium were treated with DMSO or 0.3-60 μM NDGA for 12 h. Activated caspase-3 fragments were detected using western blot analysis. Upper panel shows the 14/17 kD cleavage fragments of caspase-3, while the lower panel shows GAPDH expression as a loading control. A representative of three separate experiments is shown. B. Serum-starved SH-SY5Y cells were treated with DMSO or 60 μM NDGA for 12 h. Some cultures included 10 nM IGF-I for the entire treatment period. Lysates were collected and caspase-3 cleavage fragments were detected as above. C. SH-SY5Y cells were treated with DMSO or NDGA (30-120 μM) for 24 h, fixed, stained with propidium idodide, and subjected to flow cytometric analysis of cell cycle. Bars represent the mean+/− SEM percentage of cells in the sub-$G_0$ apoptotic phase from five separate experiments. *$p<0.05$ vs. DMSO.

IGF-stimulated cell motility is inihibited by NDGA. IGFs increase the motility of neuroblastoma cells, in part through PI-3K signaling. The ability of NDGA to impact neuroblastoma motility was assessed by measuring the motility of serum starved SHEP and SH-SY5Y cells treated with or without 1 nM IGF-I, over a 6 h period. Motility was quantified by plating the cells on coverslips coated with fine particles, and then measuring the areas cleared of particles by the cells after they moved during the 6 h incubation. IGF-I increased the motility of SH-SY5Y and SHEP cells, and 30 μM NDGA strongly suppressed this increase in motility (FIG. 21A).

NDGA inhibits tumor growth in a xenograft model of neuroblastoma. To determine if the anti-tumorigenic effects of NDGA would be observed in vivo, nude mice with established Kelly cell xenografts were treated with NDGA (50 mg/kg i.p. daily) or vehicle (n=4 per treatment group). After 10 d of treatment, all mice were sacrificed because the tumors in the vehicle treated mice had grown so large that our institutional animal care rules required the animals be sacrificed. NDGA, however, had inhibited tumor growth by 50% (FIG. 21B).

FIGS. 21A, 21B and 21C show that NDGA inhibits IGF-I stimulated motility and in vivo neuroblastoma tumor growth. A. SH-SY5Y and SHEP cells were plated on gold particle-coated coverslips in serum-free conditions. After adhering, the cells were treated with DMSO or 30 μM NDGA for 1 h. Half the cultures were then treated with 1 nM IGF-I, and incubation continued for 6 h. The track areas of cells that were etched into the gold particle coating were measured using NIH Image software. Each bar represents the mean+/− SEM of 120 individual track areas collected from three separate experiments. *$p<0.001$ vs. DMSO+1 nM IGF-I. B. Kelly neuroblastoma cells were implanted subcutaneously in nude mice as described in Materials and Methods. When palpable tumors formed (day 12), mice were treated with daily i.p. injections of DMSO (vehicle, solid line) or 50 mg/kg NDGA (dashed line). On day 22, the animals were sacrificed and tumor volume was measured with calipers. N=4 animals in each treatment group.

Discussion

The IGF signaling system has become a target of increasing interest in cancer therapy research. A variety of approaches to disrupting the system have been proposed and investigated, including use of anti-receptor antibodies, anti-sense nucleotides, and ligand mimicking compounds (Foulstone E, Prince S, Zaccheo O, et al. Insulin-like growth factor ligands, receptors, and binding proteins in cancer. J Pathology 2005:205:145-153). Decreasing IGF availability to tumors is also being considered. A fusion protein of the IGF binding proteins 3 and 6 is reported to sequester autocrine IGF-II and decrease rhabdomyosarcoma thymidine uptake (Dake BL, Boes M, Bach LA and Bar RS. Effect of an insulin-like growth factor binding protein fusion protein on thymidine incorporation in neuroblastoma and rhabdomyosarcoma cell lines. Endocrinology 2004;145:3369-3374). Small molecular inhibitors of the IGF-I receptor are another approach that is attracting much attention. A related pair of highly specific and potent inhibitors of the IGF-IR, NVP-ADW742 and NVP-AEW541, inhibit the growth of a wide variety of tumors in vitro, as well as fibrosarcoma growth in vivo (Mitsiades CS, Mitsiades NS, McMullan CJ, et al. Inhibition of the insulin-like growth factor receptor-I tryosine kinase activity as a therapeutic strategy for multiple myeloma, other hematologic malignancies, and solid tumors. Cancer Cell 2004;5:221-230; Garcia Echeverria C, Pearson MA, Marti A. et al. In vivo antitumor activity of NVP-AEW541-A novel, potent, and selective inhibitor of the IGF-IR kinase. Cancer Cell 2004;5: 231-239). Still, relatively few agents have been identified that have affects against the IGF-IR. Considering the promising pre-clinical results of anti-IGF treatment in numerous malignancies.

NDGA is a naturally occurring compound that has been extensively studied for its anti-lipoxygenase activity. It will inhibit the tyrosine phosphorylation of partially purified IGF-I and her2/neu receptors, as well as these same receptors endogenously expressed in breast cancer cells. While it is quite potent at inhibiting these receptors, NDGA does not show high selectivity for a single receptor, in contrast to NVP-ADW742 and NVP-AEW541. NDGA inhibits the activation of the PDGF receptor and PDGF-stimulated DNA synthesis (Domin J. Higgins T, and Rozengurt E. Preferential inhibition of platelet-derived growth factor-stimulated DNA synthesis and protein tyrosine phosphorylation by nordihydroguaiaretic acid. J Biol Chem 1994:269:8260-8267). Seufferlein, et al., found no affect of NDGA on EGF receptor phosphorylation, suggesting it has some selectivity (Seufferlein T. Seckl MJ, Schwarz E, et al. Mechanisms of nordihydroguaiaretic acid-induced growth inhibition and apoptosis in human cancer cells. Brit J Cancer 2002,86:1188-1196).

Due to NDGA's effects on the structurally similar insulin receptor, a diabetic phenotype is one logical toxicity to expect. Paradoxically, NDGA has an anti-diabetic effect on rats, decreasing serum glucose and triglycerides without affecting insulin levels. NDGA was previously considered for treatment of diabetes because of its inhibition of prostaglandin synthesis. Thus, NDGA's inhibition of insulin receptors may not result in a diabetes-like toxicity because of its concomitant effects on prostaglandin synthesis. NDGA analogs are being developed in an attempt to achieve better specificity, and some have been tested for efficacy against lung cancer (Moody TW, Leyton J, Martinez A, Hong S, Malkinson A and Mulshine JL. Lipoxygenase inhibitors prevent lung carcinogenesis and inhibit non-small cell lung cancer growth. Exp Lung Res 1998;24:617-628). Further characterization of these analogs may lead to the discovery of agents more specific for individual receptor tyrosine kinases.

NDGA has already been tested as a potential anti-cancer agent in several in vitro and in vivo studies, often with an underlying hypothesis that suppressing prostaglandin synthesis will suppress tumor growth without directly evaluating this mechanism of action. NDGA is effective in vitro against numerous tumor cell types, where it induces apoptosis and suppresses mitogenesis (Seufferlein T, Seckl MJ, Schwarz E, et al. Mechanisms of nordihydroguaiaretic acid-induced growth inhibition and apoptosis in human cancer cells. Brit J Cancer 2002:86:1188-1196: Tong W-G, Ding X-Z, Witt RC and Adrian TE. Lipoxygenase inhibitors attenuate growth of human pancreatic cancer xenografts and induce apoptosis through the mitochondrial pathway. Mol Cancer Therap 2002;1:929-935; Hoferova Z, Fedorocko P, Hofer M, Hofmanova J, Kozubik A and Eliasova V. Lipoxygenase inhibitors suppress proliferation of G5:113 fibrosarcoma cells in vitro but they have no anticancer activity in vivo. Neoplasm 2003;50:102-109; Vondracek J, Stika JV, Soucek K, et al. Inhibitors of arachidonic acid metabolism potentiate tumor necrosis factor-alpha-induced apoptosis in HL-60 cells. Eur J Pharmacol 2001:424:1-11). Cancers that are highly responsive to IGF, including lung (Moody TW, Leyton J, Martinez A, Hong S, Malkinson A and Mulshine JL. Lipoxygenase inhibitors prevent lung carcinogenesis and inhibit non-small cell lung cancer growth. Exp Lung Res 1998;24:617-628) and breast, respond to NDGA treatment in vivo.

Considering its potency in inhibiting IGF-IR phosphorylation, NDGA could be effective in suppressing the growth of neuroblastoma tumors, which are highly responsive to IGFs. Both paracrine and autocrine IGFs stimulate neuroblastoma mitogenesis. Neuroblastoma cell lines that secrete IGF-II are capable of serum-independent growth. Additionally, cell lines that express high levels of the IGF-IR are more aggressively tumorigenic. IGFs strongly activate the MAPK signaling pathway, which culminates in phosphorylation of ERK 1 and 2. Thus, interrupting IGF signaling at the level of the receptor can be used to prevent the growth of neuroblastoma tumors.

The present invention shows that NDGA at low doses (15-30 µM) completely blocks neuroblastoma growth over a period of several days in vitro, both in serum and serum-free conditions where added and autocrine IGFs support neuroblastoma growth. The growth of Kelly neuroblastoma tumor xenografts in nude mice is also suppressed by NDGA. A single daily dose of an NDGA formulation of the invention, was very well tolerated by the mice, and inhibited tumor growth by 50% . NDGA prevents IGF-I-mediated activation of both the IGF-IR and ERK 1 and 2 in neuroblastoma cells at the same doses that inhibit growth in vitro. NDGA was similarly effective at inhibiting IGF-IR signaling and the growth of breast cancer cells in vitro and in xenografts. The effects of NDGA on other molecular targets notwithstanding, the ability of NDGA to inhibit mitogenesis in these experiments is likely attributable at least in part to blocking IGF-IR activation.

IGFs are also potent stimulators of neuroblastoma survival, causing strong activation of Akt and Bcl-2 while suppressing caspase-3 activation. Results provided here show that NDGA causes neuroblastoma death as the dose is increased and is strongly apoptotic, causing caspase-3 activation and a large increase in sub-$G_0$ cells. IGF-I normally can prevent caspase activation in neuroblastoma cells, but IGF-I activation of Akt was inhibited in cells treated with NDGA. Additionally, IGF-I was only partially able to mitigate NDGA-induced caspase-3 activation. NDGA appears to prevent the survival-promoting effects of IGFs by interrupting signaling pathways. Similar results are seen in breast cancer cell lines treated with NDGA, where Akt activation is suppressed and BAD activation is increased. NDGA and other lipoxygenase inhibitors cause caspase-3 activation in pancreatic cancer cells; thus, a lipoxygenase-related mechanism is also possible in neuroblastoma.

IGF-I stimulates neuroblastoma cells to undergo organized actin polymerization and lamellipodium extension, resulting in increased cell motility. Increased cell motility, along with the ability to digest extracellular matrix, affords cancer cells greater ability to invade tissues and blood vessels, leading to metastasis and diffuse tissue dissemination. This is of particular concern with neuroblastoma, where tumor invasion of bone, a site of high IGF production, is associated with poor response to therapy. NDGA effectively inhibits IGF-I stimulated motility of neuroblastoma cells at a low dose.

The present invention shows that NDGA effectively suppresses neuroblastoma growth in vitro and in vivo, and inhibits the motility and promotes the apoptosis of neuroblastoma cells in culture. These effects are attributable, at least in part, to the prevention of IGF-IR activation by IGFs, an important event in the regulation of neuroblastoma growth, survival, and motility. The present invention also shows that NDGA administration to animals is well-tolerated and effective. The NDGA formulation of the invention can be co-administered with anti-myc agents and/or radiation, so as to be even more effective in treatments that affect other aspects of neuroblastoma tumorigenesis. NDGA, in combination with other agents that affect IGF action, such as IGF binding proteins or anti-PI-3K agents, can provide increased tumor kill with decreased general toxicities.

Example 3

Materials and Methods

Materials

NDGA and IGF-I were a gift from Insmed Inc. (Glen Allen, Va.). Antibodies against the IGF-IR (C-20), HER2 (C-18), and phosphospecific antibodies recognizing phosphotyrosine (PY20), and pNeu (Tyr1248), and HRP-conjugated anti-phosphotyrosine antibody (PY20HRP) were all obtained from Santa Cruz Biotechnology (Santa Cruz, Calif.). Alpha IR3, a monoclonal antibody against the IGF-1R, was obtained from CalBiochem (San Diego, Calif.). Phosphospecific antibodies pIGF-IR (Y1131) and pAkt(ser473) were obtained from Cell Signaling (Beverly, Mass.). All other reagents were from Sigma (St. Louis, Mo.), except as indicated below. Gefitinib (Iressa) was a gift of Mark Moasser, University of California San Francisco. Herceptin was purchased from a commercial pharmacy.

Cell Culture

MCF-7 cells stably transfected with the full length HER2 cDNA (MCF-7/HER2-18) or control vector (MCF-7/neo) were generously provided by Dr. Christopher Benz (Buck Institute for Age Research, Novato, Calif.) and were maintained at 37 oC, 5% CO2 in DMEM+10% FCS (DMEM-10) supplemented with 200 µg/ml Geneticine.

Preparation of Cell Lysates

For dose effects of RTK inhibitors (NDGA or gefitinib) on cellular IGF-1R and HER2 signaling, cells were grown in 6-well plates to ~80% confluency, then serum-starved for 18 hr. RTK inhibitors were dissolved in DMSO and diluted with culture medium before being added to cells for 1.5 hour at 37° C. The final concentration of DMSO during the incubation was 0.3%. For some studies, cells were also stimulated with 3 nM IGF-I for 10 minutes at 37° C. Reactions were terminated by rapidly aspirating medium and washing cells three times with ice cold PBS. Cells were harvested and solubilized in 50 mM HEPES, 150 mM NaCl, 1% Triton X-100, 1 mM PMSF, and 2 mM vanadate for 1 hour at 4° C. Protein concentrations were determined by BCA assay (Pierce, Rockford, Ill.). Enzyme linked immunosorbent assays (ELISA) for phosphorylated IGF-1R and HER2 IGF-1R phosphorylation was determined by ELISA as described previously for the insulin receptor [Youngren JF, Goldfine ID and Pratley RE: Decreased muscle insulin receptor kinase con-elates with insulin resistance in normoglycemic Pima Indians. Am J Physiol 273: E276-83, 1997]. Briefly, 10 µg lysate protein were added to triplicate wells in a 96-well plate coated with monoclonal antibody to the IGF-IR (IR3; 2 µg/ml), and incubated for 18 hours at 4° C. Plates were washed five times and then HRP-conjugated anti-phosphotyrosine antibody (0.3 µg/ml), diluted in Solution B (50 mM HEPES, pH 7.6, 150 mM NaCl, 0.05% Tween-20, 1 mM PMSF, 2 mM vanadate and 1 mg/ml bacitracin), was added for two hours at 22° C. Plates were washed five times prior to color development with TMB substrate, which was terminated with 1.0 M H3PO4. Values for receptor phosphorylation were determined by measuring absorbance at 450 nm.

HER2 phosphorylation was also determined by ELISA as above, using 2 µg of lysate protein per well and 2 µg/ml Herceptin as the capturing antibody.

Western Blot Analysis

Total protein extracts (10 µg), prepared as described above from cells cultured in the presence or absence of IGF-1 and/or RTK inhibitors, were subjeccted to SDS-PAGE and subsequently transferred to nitrocellulose membranes. Membranes were incubated overnight at 4 oC with primary antibody diluted in Superblock (Pierce) containing 0.1% Tween 20 (Bio-Rad). The membranes were washed 3 times with TBS-T, then incubated with HRP-conjugated secondary antibody diluted in Superblock/Tween20 for 90 min at room temperature. Membranes were washed again and bound antibodies detected by enhanced chemiluminescence (Pierce). Primary antibodies against the following proteins were used at the indicated dilutions: IGF-1R used at 0.2 µg/ml, HER2 used at 0.2 µg/ml, p-IGF-1R (Y1131) used at 1:1000, pNeu (Tyr1248) used at 0.2 µg/ml, and pAkt(ser473) used at 1:1000. Secondary HRP-conjugated antibodies were directed against the appropriate species of origin of the primary antibody.

Cell Growth Assays

The inhibitory effects of RTK inhibitors (NDGA and gefitinib) on breast cancer cell growth were determined using a CyQuant cell proliferation assay kit (Molecular Probes, Eugene, OR). MCF-7/neo or MCF-7/HER2-18 cells were plated in 96 well plates (4×103 cells/well) in 100 µl/well of DMEM-10 medium. Cells were allowed to adhere overnight and were then treated with various concentrations of NDGA, gefitinib, or DMSO as a vehicle control in 100 µl/well of serum free DMEM (SF-DMEM), making the final serum concentration 5%. Media with inhibitors was refreshed on day 3 and the cultures were harvested on day 6. The plates were inverted onto paper towels with gentle blotting to remove growth medium without disrupting adherent cells. Each plate was kept at −80° C. until assayed for cell growth. After thawing the plate at room temperature, 200 µl of CyQuant GR solution was added to each well and the plates were incubated in the dark for five minutes. Fluorescence was measured with a SpectraMax Gemini XS fluorescence microplate reader (Molecular Devices) with 480-nm excitation and 520-nm emission.

The growth inhibitory effects of tamoxifen, in the presence or absence of NDGA, were assessed in MCF-7/HER2-18 cells using a CyQuant assay as described above with a few modifications to the protocol. Cells were estrogen-starved for three days in DMEM containing 10% charcoal-dexthin-stripped FCS (CDSS) prior to their plating in 96 well plates. Cells were plated in 100 µl of the same media, allowed to adhere overnight, and then were switched to DMEM+10% CDSS supplemented with 100 pM estrogen. Tamoxifen (100 nM final concentration) and/or NDGA (10-20 µM final concentration) was added in 100 µl of SF-DMEM to yield a final concentration of 5% CDSS in DMEM. The media and inhibitors were refreshed on day 3, the cultures were harvested on day 6, and a CyQuant assay was performed as described above.

Results

HER2 Receptor, but not the IGF-1R, is Overexpressed in Tamoxifen Resistant MCF-7/HER2-18 Cells Various studies have demonstrated reduced IGF-1R expression in antiestrogen-resistant cell lines [Brockdorff BL, Heiberg I and Lykkesfeldt AE: Resistance to different antiestrogens is caused by different multi-factorial changes and is associated with reduced expression of IGF receptor Ialpha. Endocr Relat Cancer 10: 579-90, 2003; Frogne T, Jepsen JS, Larsen SS, Fog CK, Brockdorff BL and Lykkesfeldt AE: Antiestrogen-resistant human breast cancer cells require activated protein kinase B/Akt for growth. Endocr Relat Cancer 12: 599-614, 2005: McCotter D, van den Berg HW, Boylan M and McKibben B: Changes in insulin-like growth factor-I receptor expression and binding protein secretion associated with tamoxifen resistance and estrogen independence in human breast cancer cells in vitro. Cancer Lett 99: 239-45, 1996; van den Berg HW, Claffie D, Boylan M, McKillen J. Lynch M and McKibben B: Expression of receptors for epidermal growth factor and insulin-like growth factor I by ZR-75-1 human breast cancer cell variants is inversely related: the effect of steroid hormones on insulin like growth factor I receptor expression. Br J Cancer 73: 477-81, 1996]. We examined the levels of the IGF-1R and HER2 proteins in parental MCF-7/neo and MCF-7/HER2-18 cells using Western blot analyses. Compared to the MCF-7/neo cells, the level of IGF-1R was decreased in MCF-7/HER2-18 cells (FIG. 22), consistent with the reports described above.

In contrast, the HER2 protein was abundant in the MCF-7/HER2-18 cells but undetectable in MCF-7/neo cells (FIG. 22). This observation is in agreement with the original report that MCF-7/HER2-18 cells overexpress the HER2 protein compared to parental MCF-7 cells [Benz CC, Scott GK, Sarup JC, Johnson RM, Tripathy D, Coronado E, Shepard HM and Osborne CK: Estrogen-dependent, tamoxifen-resistant tumorigenic growth of MCF-7 cells transfected with HER2/neu. Breast Cancer Res Treat 24: 85-95, 1993].

NDGA, but not Gefitinib, Equally Inhibits the Growth of Both Parental and Tamoxifen Resistant MCF-7/HER2-18 Cells Gefitinib, an EGFR inhibitor, has been shown to inhibit the growth of HER2-overexpressing breast cancer cell lines, including MCF-7/HER2-18[Anderson NG, Ahmad T, Chan K, Dobson R and Bundred NJ: ZD1839 (Iressa), a novel epidermal growth factor receptor (EGFR) tyrosine kinase inhibitor, potently inhibits the growth of EGFR-positive cancer cell lines with or without erbB2 overexpression. Int J Cancer 94: 774-82, 2001: Moasser MM, Basso A, Averbuch SD and Rosen N: The tyrosine kinase inhibitor ZD1839 ("Iressa") inhibits HER2-driven signaling and suppresses the growth of HER2-overexpressing tumor cells. Cancer Res 61: 7184-8, 2001; Moulder SL, Yakes FM, Muthuswamy SK, Bianco R, Simpson JF and Arteaga CL: Epidermal growth factor receptor (HER1) tyrosine kinase inhibitor ZD1839 (Iressa) inhibits HER2/neu (erbB2)-overexpressing breast cancer cells in vitro and in vivo. Cancer Res 61: 8887-95, 2001]. NDGA inhibits both HER2 and IGF-1R activities and has been shown to inhibit the growth of HER2-negative (MCF-7) as well as HER2-positive (SKBr3) breast cancer cells [Youngren JF, Gable K, Penaranda C, Maddux BA, Zavodovskaya M, Lobo M, Campbell M, Kerner J and Goldfine ID: Nordihydroguaiaretic acid (NDGA) inhibits the IGF-1 and cerbB2/HER2/neu receptors and suppresses growth in breast cancer cells. Breast Cancer Res Treat 94: 37-46, 2005]. We compared the effects of both tyrosine kinase inhibitors on the growth of parental MCF-7/neo and MCF-7/HER2-18 cells. Gefitinib (FIG. 23A) was more effective at inhibiting the growth of HER2-overexpressing MCF-7/HER2-18 cells when compared to MCF-7/neo cells. In contrast, NDGA was equally effective in both cells lines, with a one half maximal effect occurring at 12.5 μM (FIG. 23B).

NDGA Inhibits both the IGF-1R and HER2 Receptor and Downstream Signaling in Tamoxifen Resistant MCF-7/HER2-18 Cells The tamoxifen resistant MCF-7/HER2-18 cell line expresses both IGF-1R and HER2, two receptor tyrosine kinases (RTK) that play a role in breast cancer. We have previously shown that NDGA inhibits the kinase activities of IGF-1R in MCF-7 cells and HER2 in SKBR-3 cells [Youngren JF, Gable K, Penaranda C, Maddux BA, Zavodovskaya M, Lobo M, Campbell M, Kerner J and Goldfine ID: Nordihydroguaiaretic acid (NDGA) inhibits the IGF-1 and cerbB2/HER2/neu receptors and suppresses growth in breast cancer cells. Breast Cancer Res Treat 94: 37-46, 2005]. We next compared the effects of NDGA with gefitinib on the activities of these receptor kinases in MCF-7/HER2-18 cells.

Employing a sensitive ELISA [Youngren JF, Goldfine ID and Pratley RE: Decreased muscle insulin receptor kinase correlates with insulin resistance in normoglycemic Pima Indians. Am J Physiol 273: E276-83, 1997] we observed that gefitinib had only a weak inhibitory effect on IGF-1 stimulated phosphorylation of the IGF-1R (FIG. 24A). In contrast, gefitinib significantly inhibited HER2 phosphorylation with a half maximal effect occurring at less than 5 μM (FIG. 24A). Whereas gefitinib suppressed HER2 but not IGF-1R activity, NDGA strongly inhibited both kinases as measured by phosphotyrosine specific ELISAs (FIG. 24B) and by Western blot (FIG. 24B, inset).

The serine kinase AKT/PKB is activated by receptor tyrosine kinases, including IGF-1R and HER2, and mediates cell growth [Ahmad S, Singh N and Glazer RI: Role of AKT1 in 17 beta-estradiol- and insulin-like growth factor I (IGF-I)-dependent proliferation and prevention of apoptosis in MCF-7 breast carcinoma cells. Biochem Pharmacol 58: 425-30, 1999: Martin MB, Franke TF, Stoica GE, Chambon P, Katzenellenbogen BS, Stoica BA, McLemore MS, Olivo SE and Stoica A: A role for Akt in mediating the estrogenic functions of epidermal growth factor and insulin-like growth factor I. Endocrinology 141: 4503-11, 2000; Mitsiades CS, Mitsiades N and Koutsilieris M: The Akt pathway: molecular targets for anticancer drug development. Curr Cancer Drug Targets 4: 235-56, 2004: Stoica GE, Franke TF, Wellstein A, Czubayko F, List HJ, Reiter R, Morgan E, Martin MB and Stoica A: Estradiol rapidly activates Akt via the ErbB2 signaling pathway. Mol Endocrinol 17: 818-30, 2003]. We measured the effects of NDGA on the phosphorylated state of this protein in MCF-7/HER2-18 cells. In the absence of IGF-1, AKT/PKB was phosphorylated and the level of phospho-AKT/PKB was decreased by treatment with NDGA (FIG. 25). Addition of 3 nM IGF-1 increased the amount of phospho-AKT/PKB and NDGA also inhibited this IGF-1 stimulated phosphorylation of AKT/PKB. NDGA did not alter the content of the AKT/PKB protein in MCF-7/HER2-18 cells (data not shown).

NDGA Attenuates Tamoxifen Resistance in HER2 Overexpressing MCF-7 Cells

Several reports have demonstrated cross-talk between IGF-1R and HER2 signaling pathways [Gee JM, Robertson JF, Gutteridge E, Ellis IO, Pinder SE, Rubini M and Nicholson RI: Epidermal growth factor receptor/HER2/insulin-like growth factor receptor signalling and oestrogen receptor activity in clinical breast cancer. Endocr Relat Cancer 12 Suppl 1: S99-S111, 2005; Lu Y, Zi X, Zhao Y and Pollak M: Overexpression of ErbB2 receptor inhibits IGF-Iinduced Shc-MAPK signaling pathway in breast cancer cells. Biochem Biophys Res Commun 313: 709-15, 2004; Nahta R, Yuan LX, Zhang B, Kobayashi R and Esteva FJ: Insulin-like growth factor-I receptor/human epidermal growth factor receptor 2 heterodimerization contributes to trastuzumab resistance of breast cancer cells. Cancer Res 65: 11118-28, 2005] as well as between ER signaling and these RTKs [Lee AV, Weng CN, Jackson JG and Yee D: Activation of estrogen receptor-mediated gene transcription by IGF-I in human breast cancer cells. J Endocrinol 152: 39-47, 1997: Martin MB and Stoica A: Insulin-like growth factor-I and estrogen interactions in breast cancer. J Nutr 132: 3799S-3801S, 2002; Yee D and Lee AV: Crosstalk between the insulin-like growth factors and estrogens in breast cancer. J Mammary Gland Biol Neoplasia 5: 107-15, 2000]. Given this cross-talk, we next examined whether NDGA (which inhibits both HER2 and IGF-1R activities) could overcome tamoxifen resistance in MCF-7/HER2-18 cells.

Figure 26:
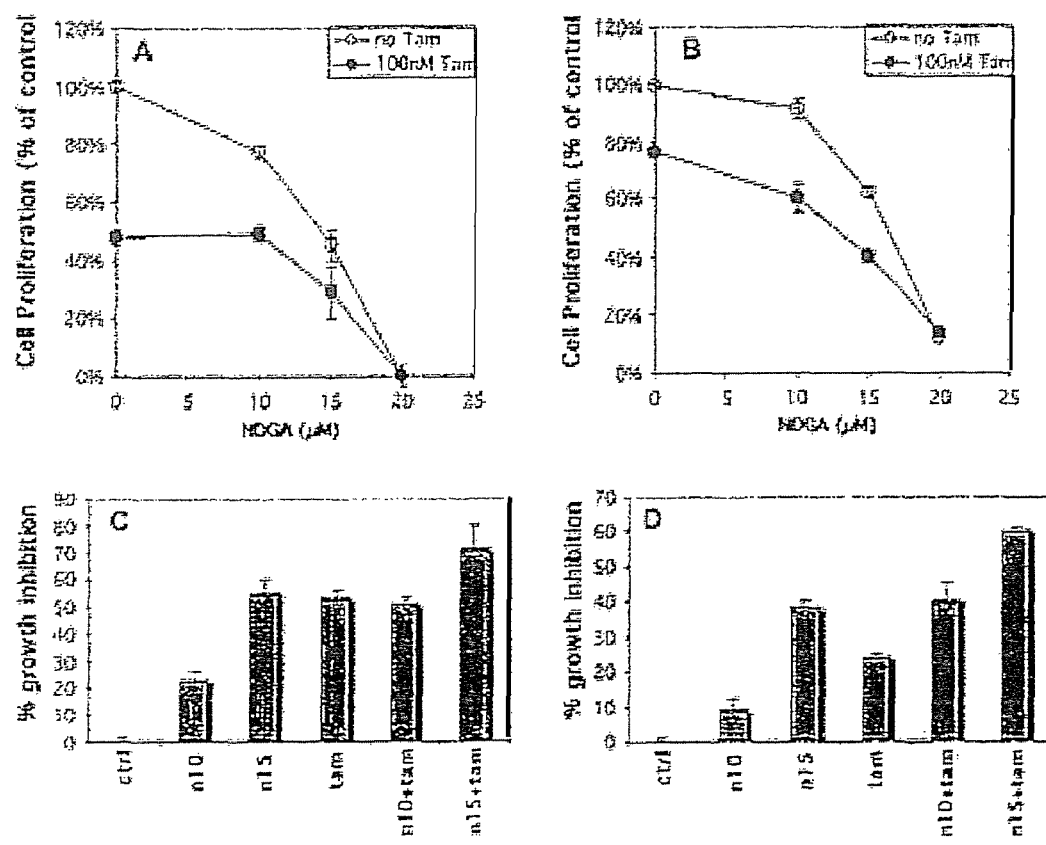

Tamoxifen at 100 nM inhibited the growth of MCF-7/neo cells by over 50% (FIG. 26A). In contrast, tamoxifen at 100 nM had less of an effect on MCF-7/HER2-18 cells (24% growth inhibition) (FIG. 26B), consistent with other reports demonstrating tamoxifen resistance of MCF-7/HER2-18 cells [Benz CC, Scott GK, Sarup JC, Johnson RM, Tripathy D, Coronado E, Shepard HM and Osborne CK: Estrogen-dependent, tamoxifen-resistant tumorigenic growth of MCF-7 cells transfected with HER2/neu. Breast Cancer Res Treat 24: 85-95, 1993].

Both NDGA and tamoxifen had antiproliferative effects on the tamoxifen sensitive MCF-7/neo cells (FIG. 26A). NDGA at 10 and 15 μM inhibited growth by 23% and 55%, respectively. However, when combined, NDGA treatment did not enhance the growth inhibitory effects of tamoxifen in these cells (FIG. 26C). In contrast to MCF-7/neo cells, NDGA treatment significantly enhanced the antiproliferative effects of tamoxifen in these anti-estrogen resistant cells (FIG. 26D). NDGA alone, at 10 and 15 µM, inhibited the growth of MCF-7/HER2-18 cells by 9 and 38%, respectively. While tamoxifen alone induced a 24% reduction in growth, the combination of tamoxifen with 10 or 15 µM NDGA resulted in 40 and 60% growth inhibition, respectively, indicating additive effects of NDGA and tamoxifen.

Discussion

Interference with growth factor signals that drive cell proliferation and survival is an attractive strategy for cancer treatment. Initial explorations have concentrated on types of cancers in which growth factor signaling is elevated and plays a dominant role in driving cell proliferation. A well known example is breast cancer with overexpression of the HER2 receptor which responds to interventions that block HER2 action, such as gefitinib [Benz CC, Scott GK, Sarup JC, Johnson RM, Tripathy D, Coronado E, Shepard HM and Osborne CK: Estrogen-dependent, tamoxifen-resistant tumorigenic growth of MCF-7 cells transfected with HER2/neu. Breast Cancer Res Treat 24: 85-95, 1993; Agrawal A, Gutteridge E, Gee JM, Nicholson RI and Robertson JF: Overview of tyrosine kinase inhibitors in clinical breast cancer. Endocr Relat Cancer 12 Suppl 1: S135-44, 2005; Arteaga CL, Moulder SL and Yakes FM: HER (erbB) tyrosine kinase inhibitors in the treatment of breast cancer. Semin Oncol 29: 4-10, 2002; Arteaga CL and Truica CI: Challenges in the development of anti-epidermal growth factor receptor therapies in breast cancer. Semin Oncol 31: 3-8, 2004; Herbst RS and Kies MS: Gefitinib: current and future status in cancer therapy. Clin Adv Hematol Oncol 1: 466-72, 2003: Johnston SR: Clinical trials of intracellular signal transductions inhibitors for breast cancer—a strategy to overcome endocrine resistance. Endocr Relat Cancer 12 Suppl 1: S145-57, 2005: Kaklamani V and O'Regan RM: New targeted therapies in breast cancer. Semin Oncol 31: 20-5. 2004; Konecny GE, Wilson CA and Slamon DJ: Is there a role for epidermal growth factor receptor inhibitors in breast cancer prevention? J Natl Cancer Inst 95: 1813-5, 2003: Penne K, Bohlin C, Schneider S and Allen D: Gefitinib (Iressa, ZD1839) and tyrosine kinase inhibitors: the wave of the future in cancer therapy. Cancer Nurs 28: 481-6, 2005; Von Pawel J: Gefitinib (Iressa, ZD1839): a novel targeted approach for the treatment of solid tumors. Bull Cancer 91: E70-6, 2004; Wakeling A E: Inhibitors of growth factor signalling. Endocr Relat Cancer 12 Suppl 1: S183-7, 2005] or Herceptin [Baselga J, Carbonell X, Castaneda-Soto NJ, Clemens M, Green M, Harvey V, Morales S, Barton C and Ghahramani P: Phase II study of efficacy, safety, and pharmacokinetics of trastuzumab monotherapy administered on a 3-weekly schedule. J Clin Oncol 23: 2162-71, 2005; Marty M, Cognetti F, Maraninchi D, Snyder R, Mauriac L, Tubiana-Hulin M, Chan S, Grimes D, Anton A, Lluch A, Kennedy J. O'Byrne K, Conte P, Green M, Ward C, Mayne K and Extra JM: Randomized phase II trial of the efficacy and safety of trastuzumab combined with docetaxel in patients with human epidermal growth factor receptor 2-positive metastatic breast cancer administered as first-line treatment: the M77001 study group. J Clin Oncol 23: 4265-74, 2005; Slamon DJ, Leyland-Jones B, Shak S, Fuchs H, Paton V, Bajamonde A, Fleming T, Eiermann W, Wolter J, Pegram M, Baselga J and Norton L: Use of chemotherapy plus a monoclonal antibody against HER2 for metastatic breast cancer that overexpresses HER2. N Engl J Med 344: 783-92, 2001; Vogel CL, Cobleigh MA, Tripathy D, Gutheil JC, Harris LN, Fehrenbacher L, Slamon DJ, Murphy M, Novotny WF, Burchmore M, Shak S, Stewart SJ and Press M: Efficacy and safety of trastuzumab as a single agent in first-line treatment of HER2-overexpressing metastatic breast cancer. J Clin Oncol 20: 719-26, 2002]. Herein we have examined the action of NDGA, an agent that blocks signaling through HER2 receptors, as well as IGF-1 receptors [Youngren JF, Gable K, Penaranda C, Maddux BA, Zavodovskaya M, Lobo M, Campbell M, Kerner J and Goldfine ID: Nordihydroguaiaretic acid (NDGA) inhibits the IGF-1 and cerbB2/HER2/neu receptors and suppresses growth in breast cancer cells. Breast Cancer Res Treat 94: 37-46, 2005], and compared it with that of gefitinib which is directed exclusively at EGFR/HER2 receptors. Both of these drugs work at the level of preventing receptor auto-phosphorylation, a factor that was monitored in our studies.

We studied the actions of these drugs on MCF-7/neo cells, an estrogen receptor positive human breast cancer cell line that is sensitive to the antiestrogen tamoxifen, and MCF-7/HER2-18 cells that overexpress the HER2 receptor and demonstrate a reduced sensitivity to tamoxifen. MCF-7/neo cells express IGF-1 receptors but not HER2, whereas the MCF-7/HER2-18 cell line expresses both IGF-1R and HER2.

Our studies show that gefitinib, as expected from its mode of action, inhibits the growth of MCF-7/HER2-18 cells, but has less potency on MCF-7/neo cells. These observations are consistent with the notion that inhibition of HER2 receptors is likely to be most effective on cells whose proliferation is driven by enhanced activity of this receptor pathway. In contrast to the selective efficacy of gefitinib, we found that NDGA is equally effective in inhibiting cell proliferation of both MCF-7/neo cells and MCF-7/HER2-18 cells. Inhibition of MCF-7/HER2-18 cells by NDGA is accompanied by an increase in apoptosis (data not shown) as well as a decrease in downstream signaling (Akt phosphorylation). The kinetics of inhibition of cell proliferation of MCF-7/HER2-18 cells match those of NDGA inhibition of IGF-1 receptor phosphorylation with half-maximal effects in the range of 10-20 µM. Inhibition of HER2 receptor phosphorylation was also evident, with half-maximal effects in the range of 30 µM. Breast cancers are either estrogen-dependent or -independent. A subset of breast cancers, despite the presence of estrogen receptors, do not respond to endocrine therapy and it has been reported that HER2 expression is associated with a reduced response rate to hormone therapy of metastatic breast cancer [Wright C, Angus B, Nicholson S, Sainsbury JR, Cairns J, Gullick WJ, Kelly P, Harris AL and Horne CH: Expression of c-erbB-2 oncoprotein: a prognostic indicator in human breast cancer. Cancer Res 49: 2087-90, 1989]. Transfection of ER-positive cells with a HER2 cDNA, resulting in overexpression of this RTK, also results in resistance to tamoxifen treatment [Benz CC, Scott GK, Sarup JC, Johnson RM, Tripathy D, Coronado E, Shepard HM and Osborne CK: Estrogen-dependent, tamoxifen-resistant tumorigenic growth of MCF-7 cells transfected with HER2/neu. Breast Cancer Res Treat 24: 85-95. 1993]. The mechanism of this resistance includes signaling from the HER2 receptor to ER alpha which results in phosphorylation and enhanced action of the hormone independent transcriptional activation function one (AF1) of the receptor. Additionally HER2 signaling leads to phosphorylation and enhanced action of the major coactivator for ERalpha driven gene expression, the amplified in breast cancer 1 (AIB1) coactivator [Shou J, Massarweh S, Osborne CK, Wakeling AE, Ali S, Weiss H and Schiff R: Mechanisms of tamoxifen resistance: increased estrogen receptor-HER2/neu cross-talk in ER/HER2-positive breast cancer. J Natl Cancer Inst 96: 926-35, 2004]. In addition to these effects downstream of HER2, a feed forward loop in which the liganded ERalpha stimulates the HER2 pathway is activated. The result is that tamoxifen mimics estrogen and drives proliferation.

In view of the disruption of tamoxifen action in HER2-overexpressing cells, studies have examined the effects of blocking HER2 signaling in tamoxifen resistant breast cancer cells. It has been shown that gefitinib can overcome tamoxifen resistance, or prevent its development, both in vitro and in a mouse xenograft model [Shou J, Massarweh S, Osborne CK, Wakeling AE, Ali S, Weiss H and Schiff R: Mechanisms of tamoxifen resistance: increased estrogen receptor-HER2/neu cross-talk in ER/HER2-positive breast cancer. J Natl Cancer Inst 96: 926-35, 2004: Gee JM, Harper ME, Hutcheson IR, Madden TA, Barrow D, Knowlden JM, McClelland RA, Jordan N, Wakeling AE and Nicholson RI: The antiepidermal growth factor receptor agent gefitinib (ZD1839/Iressa) improves antihormone response and prevents development of resistance in breast cancer in vitro. Endocrinology 144: 5105-17, 2003; Kurokawa H and Arteaga CL: Inhibition of erbB receptor (HER) tyrosine kinases as a strategy to abrogate antiestrogen resistance in human breast cancer. Clin Cancer Res 7: 4436s-4442s; discussion 4411s-4412s, 2001]. However, continuous treatment eventually leads to acquired resistance to gefitinib which is associated with increased signaling via the IGF-1R [Jones HE, Goddard L, Gee JM, Hiscox S, Rubini M, Barrow D, Knowlden JM, Williams S, Wakeling AE and Nicholson RI: Insulin-like growth factor-I receptor signalling and acquired resistance to gefitinib (ZD1839: Iressa) in human breast and prostate cancer cells. Endocr Relat Cancer 11: 793-814, 2004].

In addition to interactions between ER and HER2 signaling pathways, cross-talk between IGF-1R and HER2 in breast cancer cells has been reported [Gee JM, Robertson JF, Gutteridge E, Ellis IO, Pinder SE, Rubini M and Nicholson RI: Epidermal growth factor receptor/HER2/insulin-like growth factor receptor signalling and oestrogen receptor activity in clinical breast cancer. Endocr Relat Cancer 12 Suppl 1: S99-S111, 2005: Lu Y, Zi X, Zhao Y and Pollak M: Overexpression of ErbB2 receptor inhibits IGF-Iinduced Shc-MAPK signaling pathway in breast cancer cells. Biochem Biophys Res Commun 313: 709-15, 2004; Nahta R, Yuan LX, Zhang B, Kobayashi R and Esteva FJ: Insulin-like growth factor-I receptor/human epidermal growth factor receptor 2 heterodimerization contributes to trastuzumab resistance of breast cancer cells. Cancer Res 65: 11118-28, 2005]. We also have observed of cross-talk between IGF-1R and HER2 in MCF-7/HER2-18 cells (unpublished data). Given that IGF-1R signaling plays a role in the development of gefitinib resistance in tamoxifen resistant cells, and that there is cross-talk between ER, IGF-1R, and HER2 signaling pathways, we examined the interaction of NDGA (which inhibits both IGF-1R and HER2) with tamoxifen on the growth of tamoxifen resistant MCF-7/HER2-18 cells. NDGA alone inhibited the proliferation of both tamoxifen sensitive MCF-7/neo and tamoxifen resistant MCF-7/HER2-18 cells. Notably, NDGA combined with tamoxifen demonstrated additive growth inhibitory effects on MCF-7/HER2-18 cells. The development of acquired resistance to anti-hormonal therapies such as tamoxifen is a major therapeutic problem in breast cancer. These results suggest that NDGA might be clinically useful, in conjunction with anti-hormonal agents, in the treatment of hormone-resistant breast cancer, or possibly in preventing the development of acquired resistance to these agents.

In summary, we demonstrated that NDGA inhibits the kinase activities of the IGF-1 receptor and the HER2 receptor and blocks cellular proliferation of both MCF-7/neo and MCF-7/HER2-18 cells. NDGA also attenuated tamoxifen resistance in the HER2-overexpressing MCF-7/HER2-18 cell line. These data raise the possibility that NDGA, and similar agents that target multiple growth factor pathways, will have a broad spectrum of action on breast cancers with a variety of perturbations in their signaling pathways.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a human breast cancer patient, wherein breast cancer cells in the cancer patient express Her2/neu receptor, comprising the steps of:
   administering to the patient a therapeutically effective amount of a formulation comprising: (1) a pharmaceutically acceptable carrier; (2) nordihydroguaiaretic acid (NDGA) or pharmaceutically acceptable salts thereof; and (3) doxorubicin, wherein the NDGA and doxorubicin act synergistically to inhibit growth of the breast cancer cells, and wherein doxorubicin and NDGA are administered in amounts below a therapeutically effective amount of either doxorubicin or NDGA when doxorubicin or NDGA are administered alone.

2. A method of treating a human breast cancer patient, wherein breast cancer cells in the cancer patient do not express Her2/neu receptor, comprising the steps of:
   administering to the patient a therapeutically effective amount of a formulation comprising: (1) a pharmaceutically acceptable carrier; (2) nordihydroguaiaretic acid (NDGA) or pharmaceutically acceptable salts thereof; and (3) doxorubicin, wherein the NDGA and doxorubicin act synergistically to inhibit growth of the breast cancer cells, and wherein doxorubicin and NDGA are administered in amounts below a therapeutically effective amount of either doxorubicin or NDGA when doxorubicin or NDGA are administered alone.

3. A method of treating breast cancer in a human patient, comprising the steps of:
   contacting breast cancer cells of the patient with a formulation comprising a pharmaceutically acceptable carrier, a therapeutically effective amount of nordihydroguaiaretic acid (NDGA) and doxorubicin, wherein the NDGA and doxorubicin act synergistically to inhibit growth of the breast cancer cells; and
   allowing the formulation to contact the cells for a sufficient period of time so as to result in death of the breast cancer cells, and wherein doxorubicin and NDGA are administered in amounts below a therapeutically effective amount of either doxorubicin or NDGA when doxorubicin or NDGA are administered alone.

4. The method of claim 3, wherein the amount of doxorubicin administered is less than 60 mg/m$^2$ once in 21 days, or less than 30 mg/m$^2$ daily for 3 days every four weeks.

5. The method of claim 3, wherein the amount of NDGA is less than 100 mg/kg orally three times a week, or 37.5 mg/kg intraperitoneally three times a week.

6. The method of claim 1, wherein the amount of doxorubicin administered is less than 60 mg/m$^2$ once in 21 days, or less than 30 mg/m$^2$ daily for 3 days every four weeks.

7. The method of claim 1, wherein the amount of NDGA is less than 100 mg/kg orally three times a week, or 37.5 mg/kg intraperitoneally three times a week.

8. The method of claim 2, wherein the amount of doxorubicin administered is less than 60 mg/m$^2$ once in 21 days, or less than 30 mg/m$^2$ daily for 3 days every four weeks.

9. The method of claim 2, wherein the amount of NDGA is less than 100 mg/kg orally three times a week, or 37.5 mg/kg intraperitoneally three times a week.

10. A method of treating a human breast cancer patient, wherein breast cancer cells in the cancer patient express Her2/neu receptor, comprising the steps of:
    administering to the patient a therapeutically effective amount of a formulation comprising: (1) a pharmaceutically acceptable carrier; (2) nordihydroguaiaretic acid (NDGA) or pharmaceutically acceptable salts thereof; and (3) doxorubicin, wherein the NDGA and doxorubicin act synergistically to inhibit growth of the breast cancer cells, and wherein the amount of doxorubicin administered is less than 60 mg/m$^2$ once in 21 days, or less than 30 mg/m$^2$ daily for 3 days every four weeks and the amount of NDGA is less than 100 mg/kg orally three times a week, or 37.5 mg/kg intraperitoneally three times a week.

11. A method of treating a human breast cancer patient, wherein breast cancer cells in the cancer patient do not express Her2/neu receptor, comprising the steps of:
    administering to the patient a therapeutically effective amount of a formulation comprising: (1) a pharmaceutically acceptable carrier; (2) nordihydroguaiaretic acid (NDGA) or pharmaceutically acceptable salts thereof; and (3) doxorubicin, wherein the NDGA and doxorubicin act synergistically to inhibit growth of the breast cancer cells, and wherein the amount of doxorubicin administered is less than 60 mg/m$^2$ once in 21 days, or less than 30 mg/m$^2$ daily for 3 days every four weeks and the amount of NDGA is less than 100 mg/kg orally three times a week, or 37.5 mg/kg intraperitoneally three times a week.

12. A method of treating breast cancer in a human patient, comprising the steps of:
    contacting breast cancer cells of the patient with a formulation comprising a pharmaceutically acceptable carrier, a therapeutically effective amount of nordihydroguaiaretic acid (NDGA) and doxorubicin, wherein the NDGA and doxorubicin act synergistically to inhibit growth of the breast cancer cells, and wherein the amount of doxorubicin administered is less than 60 mg/m$^2$ once in 21 days or less than 30 mg/m$^2$ daily for 3 days every four weeks, and the amount of NDGA is less than 100 mg/kg orally three times a week or 37.5 mg/kg intraperitoneally three times a week; and
    allowing the formulation to contact the cells for a sufficient period of time so as to result in death of the breast cancer cells.

* * * * *